(12) United States Patent
Das Gupta et al.

(10) Patent No.: US 10,086,037 B2
(45) Date of Patent: *Oct. 2, 2018

(54) COMPOSITIONS AND METHODS TO PREVENT CANCER WITH CUPREDOXINS

(76) Inventors: Tapas Das Gupta, River Forest, IL (US); Ananda Chakrabarty, Villa Park, IL (US); Craig Beattie, Chicago, IL (US); Tohru Yamada, Lombard, IL (US)

( * ) Notice: Subject to any disclaimer, the term of this patent is extended or adjusted under 35 U.S.C. 154(b) by 266 days.

This patent is subject to a terminal disclaimer.

(21) Appl. No.: 13/561,225

(22) Filed: Jul. 30, 2012

(65) Prior Publication Data

US 2013/0084247 A1    Apr. 4, 2013

Related U.S. Application Data

(63) Continuation of application No. 12/028,683, filed on Feb. 8, 2008, now Pat. No. 8,232,244.

(60) Provisional application No. 60/900,098, filed on Feb. 8, 2007.

(51) Int. Cl.

| | | |
|---|---|---|
| A61K 38/00 | (2006.01) | |
| A61K 38/16 | (2006.01) | |
| A61K 49/00 | (2006.01) | |
| A61K 49/04 | (2006.01) | |
| A61K 49/08 | (2006.01) | |
| A61K 49/14 | (2006.01) | |
| C07K 14/21 | (2006.01) | |
| C07K 14/415 | (2006.01) | |
| A61M 5/00 | (2006.01) | |
| C07K 14/00 | (2006.01) | |
| C07K 14/22 | (2006.01) | |
| C07K 14/225 | (2006.01) | |
| C07K 14/235 | (2006.01) | |
| C07K 14/28 | (2006.01) | |
| C07K 14/32 | (2006.01) | |
| C12Q 1/02 | (2006.01) | |
| C12Q 1/04 | (2006.01) | |
| A61K 47/54 | (2017.01) | |
| A61K 47/64 | (2017.01) | |
| B82Y 5/00 | (2011.01) | |

(52) U.S. Cl.
CPC .......... *A61K 38/164* (2013.01); *A61K 47/549* (2017.08); *A61K 47/64* (2017.08); *A61K 49/0002* (2013.01); *A61K 49/04* (2013.01); *A61K 49/085* (2013.01); *A61K 49/14* (2013.01); *A61M 5/00* (2013.01); *C07K 14/00* (2013.01); *C07K 14/21* (2013.01); *C07K 14/22* (2013.01); *C07K 14/225* (2013.01); *C07K 14/235* (2013.01); *C07K 14/28* (2013.01); *C07K 14/32* (2013.01); *C07K 14/415* (2013.01); *C12Q 1/025* (2013.01); *C12Q 1/04* (2013.01); *A61K 38/00* (2013.01); *B82Y 5/00* (2013.01)

(58) Field of Classification Search
None
See application file for complete search history.

(56) References Cited

U.S. PATENT DOCUMENTS

| | | | |
|---|---|---|---|
| 5,281,704 A | 1/1994 | Love et al. | |
| 5,412,148 A | 5/1995 | Keana | |
| 5,417,959 A | 5/1995 | Wallace | |
| 5,567,411 A | 10/1996 | Keana et al. | |
| 5,679,810 A | 10/1997 | Love et al. | |
| 5,760,191 A | 6/1998 | Snow et al. | |
| 5,801,228 A | 9/1998 | Hollister et al. | |
| 5,804,161 A | 9/1998 | Long et al. | |
| 5,853,763 A | 12/1998 | Tice et al. | |
| 6,383,500 B1 | 5/2002 | Wooley et al. | |
| 7,301,010 B2 * | 11/2007 | Chakrabarty et al. | 530/350 |
| 7,338,766 B2 * | 3/2008 | Chakrabarty et al. | 435/6.15 |
| 7,556,810 B2 * | 7/2009 | Mehta et al. | 424/185.1 |
| 7,618,939 B2 * | 11/2009 | Gupta et al. | 514/1.1 |
| 7,691,383 B2 * | 4/2010 | Chakrabarty et al. | 424/185.1 |
| 7,807,183 B2 * | 10/2010 | Hong et al. | 424/249.1 |
| 7,888,468 B2 * | 2/2011 | Chakrabarty et al. | 530/350 |
| 8,017,749 B2 * | 9/2011 | Das Gupta et al. | 536/23.1 |
| 8,232,244 B2 * | 7/2012 | Das Gupta | C12Q 1/04 514/19.3 |
| 2002/0164703 A1 | 11/2002 | Pawlowski et al. | |
| 2006/0040269 A1 | 2/2006 | Chakrabarty et al. | |
| 2006/0149037 A1 * | 7/2006 | Chakrabarty et al. | 530/350 |
| 2006/0251639 A1 | 11/2006 | Chakrabarty et al. | |
| 2006/0251669 A1 | 11/2006 | Chakrabarty et al. | |

(Continued)

FOREIGN PATENT DOCUMENTS

| | | |
|---|---|---|
| WO | WO9719086 | 5/1997 |
| WO | WO9730992 | 8/1997 |

(Continued)

OTHER PUBLICATIONS

Ni et al., Cancer Letters 261:1-11 (2008).
(Continued)

*Primary Examiner* — Anand U Desai
(74) *Attorney, Agent, or Firm* — Benesch, Friedlander, Coplan & Aronoff LLP

(57) ABSTRACT

The present invention discloses methods and materials for delivering a cargo compound into a cancer cell. Delivery of the cargo compound is accomplished by the use of protein transduction domains derived from cupredoxins. The cargo compound may be a nucleic acid and specifically a DNA, RNA or anti-sense. The invention further discloses methods for treating cancer and diagnosing cancer.

11 Claims, 15 Drawing Sheets

Specification includes a Sequence Listing.

(56) References Cited

U.S. PATENT DOCUMENTS

| | | | |
|---|---|---|---|
| 2006/0292136 | A1 | 12/2006 | Chakrabarty et al. |
| 2008/0027002 | A1 | 1/2008 | Liik et al. |
| 2008/0103087 | A1 | 5/2008 | Mehta et al. |
| 2008/0139471 | A1 | 6/2008 | Das Gupta et al. |
| 2008/0182782 | A1 | 7/2008 | Chakrabarty et al. |
| 2008/0226560 | A1 | 9/2008 | Das Gupta et al. |
| 2009/0202441 | A1 | 8/2009 | Taylor et al. |
| 2009/0208476 | A1 | 8/2009 | Das Gupta et al. |
| 2009/0226405 | A1 | 9/2009 | Das Gupta et al. |
| 2009/0286719 | A1 | 11/2009 | Das Gupta et al. |
| 2010/0087377 | A1 | 4/2010 | Das Gupta et al. |
| 2010/0209355 | A1 | 8/2010 | Chakrabarty et al. |
| 2010/0267608 | A1 | 10/2010 | Das Gupta et al. |

FOREIGN PATENT DOCUMENTS

| | | |
|---|---|---|
| WO | WO9822461 | 5/1998 |
| WO | WO9825929 | 6/1998 |
| WO | WO9854966 | 10/1998 |
| WO | WO9901124 | 1/1999 |
| WO | WO9902224 | 1/1999 |
| WO | WO9902514 | 1/1999 |
| WO | WO9907692 | 2/1999 |
| WO | WO9927890 | 6/1999 |
| WO | WO99023324 | 6/1999 |
| WO | WO9954318 | 10/1999 |
| WO | WO9954319 | 10/1999 |
| WO | WO99543320 | 10/1999 |
| WO | WO9767252 | 12/1999 |
| WO | WO9967253 | 12/1999 |
| WO | WO0000485 | 6/2000 |
| WO | 200044888 | 8/2000 |
| WO | 2003097085 A1 | 11/2003 |
| WO | 2005018662 A1 | 3/2005 |
| WO | 2006088508 A2 | 8/2006 |
| WO | 200803380 A2 | 3/2008 |
| WO | 2008033987 A2 | 3/2008 |
| WO | 2008098216 A2 | 8/2008 |

OTHER PUBLICATIONS

Chaudhari et al., Biochemistry, American Chemical Society 46:7 1799-1810 (2007).
Yamada et al., PNAS 99(22):14098-14103 (2002).
Yamada et al., Infect Immun. 70:7054-7062.
Yamada et al., Cell. Microbial. 7:1418-1431 (2005).
Yamada et al., Cell. Cycle 3:1182-1187 (2004).
Punj et al., Oncogene. 23:2367-2378 (2004).
Chaloin et al., Bioconjugate Chem. 12:691-700.
Hallbrink et al., Biochem. Biophys. Acta 1515:101-109 (2001).
Lindgren et al., Trends Pharmacol., Sci. 21:99-103 (2000).
Schwarze et al., Science 285-1569-1572 (1999).
Liu et al., Nat. Med. 6:1380-1387 (2000).
Ghadiri & Fernholz, J. Am. Chem. Soc., 112:9633-9635 (1990).
Zaborina et al., Microbiology 146:2521-2530 (2000).
Futaki et al., J. Biol. Chem. 276(8):5836-40 (2001).
Labrie et al., Clin. Invest. Med. 13(5):275-8 (1990).
Schafmeister et al., J. Am. Chem. Soc. 122:5891-5892 (2000).
Walenski et al., Science 305:1466-1470 (2004).
Papo et al., Cancer Res. 64(16):5779-86 (2004).
Miller et al., BiochemPharmacol. 36(1):169-76 (1987).
Lee et al., J. Pept. Res. 63(2):69-84 (2004).
Monk et al., BioDrugs 19(4):261-78 (2005).
Defreest et al., J. Pept. Res. 63(5):409-19 (2004).
Toth et al., (Developmental Cell 1:82-92 (2001)).
Gough & Clothia, Structure 12:917-925 (2004).
De Rienzo et al., Protein Science 9:1439-1454 (2000).
Suzuki et al., J. Biol. Chem. 277:2437-2443 (2002).
Murphy et al., J. Mol. Biol. 315:859-871 (2002).
Redinbo et al., J. Bioenerg. Biomembr. 26:49-66 (1994).
Walter, R.L. et al., J. Mol. Biol. 263:730-51 (1996).
Van Dreissche et al., Protein Science 8:947-957 (1999).
Bond et al., J. Mol. Biol. 306:47-67 (2001).
McManus et al., J. Biol. Chem.267:6531-6540 (1992).
Koch et al., J. Am. Chem. Cov. 127:158-166 (2005).
Hart et al., Protein Science 5:2175-2183 (1996).
Guss et al., J. Mol. Biol. 262:686-705 (1996).
Cuzick, Breast 12:405-411 (2003).
Huang et al., Am. J. Epidemiol 151:703-714 (2000).
Thiberville et al., Cancer Res. 55:5133-5139 (1995).
Mai et al., J. Natl. Cancer Inst. 89:857-862 (1997).
Tsao et al., CA Clin. Cancer J. Clin. 54:150-180 (2004).
Sofer & Futerman, J. Biol. Chem. 277:2437-2443 (2002).
Kurihara et al., J. Clin. Invest. 106(6):763-771 (2000).
Carter, Biochem. J. 237:1-7 (1986).
Zoller and Smith, Methods Enzymol. 154:329-350 (1987).
Wells et al., Gene 34:315-323 (1987).
Konishi et al., J. Med. Sci. 48(3):79-89 (1999).
Gail et al., J. Natl. Cancer Inst. 81:1879-1886 (1989).
Suzuki et al., Biol. Chem. 277:2437-2743 (2002).
Ho et al., Cancer Res. 61:474-477 (2001).
Yamada et al., PNAS 101:4770-4775 (2005).
Kukimoto et al., FEBS Lett. 394:87-90 (1996).

* cited by examiner

SEQUENCE LISTING

<160> NUMBER OF SEQ ID NOS: 54

<210> SEQ ID NO 1
<211> LENGTH: 128
<212> TYPE: PRT
<213> ORGANISM: Pseudomonas aeruginosa

<400> SEQUENCE: 1

-continued

```
Ala Glu Cys Ser Val Asp Ile Gln Gly Asn Asp Gln Met Gln Phe Asn
1               5                   10                  15

Thr Asn Ala Ile Thr Val Asp Lys Ser Cys Lys Gln Phe Thr Val Asn
            20                  25                  30

Leu Ser His Pro Gly Asn Leu Pro Lys Asn Val Met Gly His Asn Trp
        35                  40                  45

Val Leu Ser Thr Ala Ala Asp Met Gln Gly Val Val Thr Asp Gly Met
    50                  55                  60

Ala Ser Gly Leu Asp Lys Asp Tyr Leu Lys Pro Asp Asp Ser Arg Val
65                  70                  75                  80

Ile Ala His Thr Lys Leu Ile Gly Ser Gly Glu Lys Asp Ser Val Thr
                85                  90                  95

Phe Asp Val Ser Lys Leu Lys Glu Gly Glu Gln Tyr Met Phe Phe Cys
            100                 105                 110

Thr Phe Pro Gly His Ser Ala Leu Met Lys Gly Thr Leu Thr Leu Lys
            115                 120                 125
```

<210> SEQ ID NO 2
<211> LENGTH: 28
<212> TYPE: PRT
<213> ORGANISM: Pseudomonas aeruginosa

<400> SEQUENCE: 2

```
Leu Ser Thr Ala Ala Asp Met Gln Gly Val Val Thr Asp Gly Met Ala
1               5                   10                  15

Ser Gly Leu Asp Lys Asp Tyr Leu Lys Pro Asp Asp
            20                  25
```

<210> SEQ ID NO 3
<211> LENGTH: 105
<212> TYPE: PRT
<213> ORGANISM: Phormidium laminosum

<400> SEQUENCE: 3

```
Glu Thr Phe Thr Val Lys Met Gly Ala Asp Ser Gly Leu Leu Gln Phe
1               5                   10                  15

Glu Pro Ala Asn Val Thr Val His Pro Gly Asp Thr Val Lys Trp Val
            20                  25                  30

Asn Asn Lys Leu Pro Pro His Asn Ile Leu Phe Asp Asp Lys Gln Val
        35                  40                  45

Pro Gly Ala Ser Lys Glu Leu Ala Asp Lys Leu Ser His Ser Gln Leu
    50                  55                  60

Met Phe Ser Pro Gly Glu Ser Tyr Glu Ile Thr Phe Ser Ser Asp Phe
65                  70                  75                  80

Pro Ala Gly Thr Tyr Thr Tyr Tyr Cys Ala Pro His Arg Gly Ala Gly
                85                  90                  95

Met Val Gly Lys Ile Thr Val Glu Gly
            100                 105
```

<210> SEQ ID NO 4
<211> LENGTH: 155
<212> TYPE: PRT
<213> ORGANISM: Thiobacillus ferrooxidans

<400> SEQUENCE: 4

```
Gly Thr Leu Asp Thr Thr Trp Lys Glu Ala Thr Leu Pro Gln Val Lys
1               5                   10                  15

Ala Met Leu Glu Lys Asp Thr Gly Lys Val Ser Gly Asp Thr Val Thr
```

```
            20                  25                  30
Tyr Ser Gly Lys Thr Val His Val Ala Ala Val Leu Pro Gly
        35                  40                  45

Phe Pro Phe Pro Ser Phe Glu Val His Asp Lys Lys Asn Pro Thr Leu
 50                  55                  60

Glu Ile Pro Ala Gly Ala Thr Val Asp Val Thr Phe Ile Asn Thr Asn
 65                  70                  75                  80

Lys Gly Phe Gly His Ser Phe Asp Ile Thr Lys Lys Gly Pro Pro Tyr
                     85                  90                  95

Ala Val Met Pro Val Ile Asp Pro Ile Val Ala Gly Thr Gly Phe Ser
                100                 105                 110

Pro Val Pro Lys Asp Gly Lys Phe Gly Tyr Thr Asp Phe Thr Trp His
                115                 120                 125

Pro Thr Ala Gly Thr Tyr Tyr Tyr Val Cys Gln Ile Pro Gly His Ala
            130                 135                 140

Ala Thr Gly Met Phe Gly Lys Ile Val Val Lys
145                 150                 155

<210> SEQ ID NO 5
<211> LENGTH: 124
<212> TYPE: PRT
<213> ORGANISM: Achromobacter cycloclastes

<400> SEQUENCE: 5

Ala Asp Phe Glu Val His Met Leu Asn Lys Gly Lys Asp Gly Ala Met
  1               5                  10                  15

Val Phe Glu Pro Ala Ser Leu Lys Val Ala Pro Gly Asp Thr Val Thr
                 20                  25                  30

Phe Ile Pro Thr Asp Lys Gly His Asn Val Glu Thr Ile Lys Gly Met
             35                  40                  45

Ile Pro Asp Gly Ala Glu Ala Phe Lys Ser Lys Ile Asn Glu Asn Tyr
         50                  55                  60

Lys Val Thr Phe Thr Ala Pro Gly Val Tyr Gly Val Lys Cys Thr Pro
 65                  70                  75                  80

His Tyr Gly Met Gly Met Val Gly Val Val Gln Val Gly Asp Ala Pro
                 85                  90                  95

Ala Asn Leu Glu Ala Val Lys Gly Ala Lys Asn Pro Lys Lys Ala Gln
            100                 105                 110

Glu Arg Leu Asp Ala Ala Leu Ala Ala Leu Gly Asn
        115                 120

<210> SEQ ID NO 6
<211> LENGTH: 128
<212> TYPE: PRT
<213> ORGANISM: Alcaligenes faecalis

<400> SEQUENCE: 6

Ala Cys Asp Val Ser Ile Glu Gly Asn Asp Ser Met Gln Phe Asn Thr
  1               5                  10                  15

Lys Ser Ile Val Val Asp Lys Thr Cys Lys Glu Phe Thr Ile Asn Leu
                 20                  25                  30

Lys His Thr Gly Lys Leu Pro Lys Ala Ala Met Gly His Asn Val Val
             35                  40                  45

Val Ser Lys Lys Ser Asp Glu Ser Ala Val Ala Thr Asp Gly Met Lys
         50                  55                  60

Ala Gly Leu Asn Asn Asp Tyr Val Lys Ala Gly Asp Glu Arg Val Ile
```

```
                65                  70                  75                  80
Ala His Thr Ser Val Ile Gly Gly Glu Thr Asp Ser Val Thr Phe
                    85                  90                  95

Asp Val Ser Lys Leu Lys Glu Gly Glu Asp Tyr Ala Phe Phe Cys Ser
                100                 105                 110

Phe Pro Gly His Trp Ser Ile Met Lys Gly Thr Ile Glu Leu Gly Ser
            115                 120                 125

<210> SEQ ID NO 7
<211> LENGTH: 129
<212> TYPE: PRT
<213> ORGANISM: Achromobacter xylosoxidans
<220> FEATURE:
<223> OTHER INFORMATION: Achromobacter xylosoxidans ssp. denitrificans I

<400> SEQUENCE: 7

Ala Gln Cys Glu Ala Thr Ile Glu Ser Asn Asp Ala Met Gln Tyr Asn
1               5                   10                  15

Leu Lys Glu Met Val Val Asp Lys Ser Cys Lys Gln Phe Thr Val His
            20                  25                  30

Leu Lys His Val Gly Lys Met Ala Lys Val Ala Met Gly His Asn Trp
        35                  40                  45

Val Leu Thr Lys Glu Ala Asp Lys Gln Gly Val Ala Thr Asp Gly Met
    50                  55                  60

Asn Ala Gly Leu Ala Gln Asp Tyr Val Lys Ala Gly Asp Thr Arg Val
65                  70                  75                  80

Ile Ala His Thr Lys Val Ile Gly Gly Gly Glu Ser Asp Ser Val Thr
                85                  90                  95

Phe Asp Val Ser Lys Leu Thr Pro Gly Glu Ala Tyr Ala Tyr Phe Cys
            100                 105                 110

Ser Phe Pro Gly His Trp Ala Met Met Lys Gly Thr Leu Lys Leu Ser
        115                 120                 125

Asn

<210> SEQ ID NO 8
<211> LENGTH: 129
<212> TYPE: PRT
<213> ORGANISM: Bordetella bronchiseptica

<400> SEQUENCE: 8

Ala Glu Cys Ser Val Asp Ile Ala Gly Thr Asp Gln Met Gln Phe Asp
1               5                   10                  15

Lys Lys Ala Ile Glu Val Ser Lys Ser Cys Lys Gln Phe Thr Val Asn
            20                  25                  30

Leu Lys His Thr Gly Lys Leu Pro Arg Asn Val Met Gly His Asn Trp
        35                  40                  45

Val Leu Thr Lys Thr Ala Asp Met Gln Ala Val Glu Lys Asp Gly Ile
    50                  55                  60

Ala Ala Gly Leu Asp Asn Gln Tyr Leu Lys Ala Gly Asp Thr Arg Val
65                  70                  75                  80

Leu Ala His Thr Lys Val Leu Gly Gly Gly Glu Ser Asp Ser Val Thr
                85                  90                  95

Phe Asp Val Ala Lys Leu Ala Ala Gly Asp Asp Tyr Thr Phe Phe Cys
            100                 105                 110

Ser Phe Pro Gly His Gly Ala Leu Met Lys Gly Thr Leu Lys Leu Val
        115                 120                 125
```

Asp

<210> SEQ ID NO 9
<211> LENGTH: 129
<212> TYPE: PRT
<213> ORGANISM: Methylomonas sp.
<220> FEATURE:
<223> OTHER INFORMATION: Methylomonas sp. J

<400> SEQUENCE: 9

```
Ala Ser Cys Glu Thr Thr Val Thr Ser Gly Asp Thr Met Thr Tyr Ser
1               5                   10                  15
Thr Arg Ser Ile Ser Val Pro Ala Ser Cys Ala Glu Phe Thr Val Asn
            20                  25                  30
Phe Glu His Lys Gly His Met Pro Lys Thr Gly Met Gly His Asn Trp
        35                  40                  45
Val Leu Ala Lys Ser Ala Asp Val Gly Asp Val Ala Lys Glu Gly Ala
    50                  55                  60
His Ala Gly Ala Asp Asn Asn Phe Val Thr Pro Gly Asp Lys Arg Val
65                  70                  75                  80
Ile Ala Phe Thr Pro Ile Ile Gly Gly Gly Glu Lys Thr Ser Val Lys
                85                  90                  95
Phe Lys Val Ser Ala Leu Ser Lys Asp Glu Ala Tyr Thr Tyr Phe Cys
            100                 105                 110
Ser Tyr Pro Gly His Phe Ser Met Met Arg Gly Thr Leu Lys Leu Glu
        115                 120                 125
Glu
```

<210> SEQ ID NO 10
<211> LENGTH: 166
<212> TYPE: PRT
<213> ORGANISM: Neisseria meningitidis
<220> FEATURE:
<223> OTHER INFORMATION: Neisseria meningitidis Z2491

<400> SEQUENCE: 10

```
Cys Ser Gln Glu Pro Ala Ala Pro Ala Ala Glu Ala Thr Pro Ala Ala
1               5                   10                  15
Glu Ala Pro Ala Ser Glu Ala Pro Ala Ala Glu Ala Ala Pro Ala Asp
            20                  25                  30
Ala Ala Glu Ala Pro Ala Ala Gly Asn Cys Ala Ala Thr Val Glu Ser
        35                  40                  45
Asn Asp Asn Met Gln Phe Asn Thr Lys Asp Ile Gln Val Ser Lys Ala
    50                  55                  60
Cys Lys Glu Phe Thr Ile Thr Leu Lys His Thr Gly Thr Gln Pro Lys
65                  70                  75                  80
Thr Ser Met Gly His Asn Ile Val Ile Gly Lys Thr Glu Asp Met Asp
                85                  90                  95
Gly Ile Phe Lys Asp Gly Val Gly Ala Ala Asp Thr Asp Tyr Val Lys
            100                 105                 110
Pro Asp Asp Ala Arg Val Val Ala His Thr Lys Leu Ile Gly Gly Gly
        115                 120                 125
Glu Glu Ser Ser Leu Thr Leu Asp Pro Ala Lys Leu Ala Asp Gly Glu
    130                 135                 140
Tyr Lys Phe Ala Cys Thr Phe Pro Gly His Gly Ala Leu Met Asn Gly
145                 150                 155                 160
Lys Val Thr Leu Val Asp
```

<210> SEQ ID NO 11
<211> LENGTH: 128
<212> TYPE: PRT
<213> ORGANISM: Pseudomonas fluorescens

<400> SEQUENCE: 11

Ala Glu Cys Lys Thr Thr Ile Asp Ser Thr Asp Gln Met Ser Phe Asn
1               5                   10                  15

Thr Lys Ala Ile Glu Ile Asp Lys Ala Cys Lys Thr Phe Thr Val Glu
            20                  25                  30

Leu Thr His Ser Gly Ser Leu Pro Lys Asn Val Met Gly His Asn Leu
        35                  40                  45

Val Ile Ser Lys Gln Ala Asp Met Gln Pro Ile Ala Thr Asp Gly Leu
50                  55                  60

Ser Ala Gly Ile Asp Lys Asn Tyr Leu Lys Glu Gly Asp Thr Arg Val
65                  70                  75                  80

Ile Ala His Thr Lys Val Ile Gly Ala Gly Glu Lys Asp Ser Leu Thr
                85                  90                  95

Ile Asp Val Ser Lys Leu Asn Ala Ala Glu Lys Tyr Gly Phe Phe Cys
            100                 105                 110

Ser Phe Pro Gly His Ile Ser Met Met Lys Gly Thr Val Thr Leu Lys
        115                 120                 125

<210> SEQ ID NO 12
<211> LENGTH: 128
<212> TYPE: PRT
<213> ORGANISM: Pseudomonas chlororaphis

<400> SEQUENCE: 12

Ala Glu Cys Lys Val Asp Val Asp Ser Thr Asp Gln Met Ser Phe Asn
1               5                   10                  15

Thr Lys Glu Ile Thr Ile Asp Lys Ser Cys Lys Thr Phe Thr Val Asn
            20                  25                  30

Leu Thr His Ser Gly Ser Leu Pro Lys Asn Val Met Gly His Asn Trp
        35                  40                  45

Val Leu Ser Lys Ser Ala Asp Met Ala Gly Ile Ala Thr Asp Gly Met
50                  55                  60

Ala Ala Gly Ile Asp Lys Asp Tyr Leu Lys Pro Gly Asp Ser Arg Val
65                  70                  75                  80

Ile Ala His Thr Lys Ile Ile Gly Ser Gly Lys Asp Ser Val Thr
                85                  90                  95

Phe Asp Val Ser Lys Leu Thr Ala Gly Glu Ser Tyr Glu Phe Phe Cys
            100                 105                 110

Ser Phe Pro Gly His Asn Ser Met Met Lys Gly Ala Val Val Leu Lys
        115                 120                 125

<210> SEQ ID NO 13
<211> LENGTH: 129
<212> TYPE: PRT
<213> ORGANISM: Xylella fastidiosa
<220> FEATURE:
<223> OTHER INFORMATION: Xylella fastidiosa 9a5c

<400> SEQUENCE: 13

Lys Thr Cys Ala Val Thr Ile Ser Ala Asn Asp Gln Met Lys Phe Asp
1 5 10 15

```
Gln Asn Thr Ile Lys Ile Ala Ala Glu Cys Thr His Val Asn Leu Thr
             20                  25                  30

Leu Thr His Thr Gly Lys Lys Ser Ala Arg Val Met Gly His Asn Trp
         35                  40                  45

Val Leu Thr Lys Thr Thr Asp Met Gln Ala Val Ala Leu Ala Gly Leu
 50                  55                  60

His Ala Thr Leu Ala Asp Asn Tyr Val Pro Lys Ala Asp Pro Arg Val
 65                  70                  75                  80

Ile Ala His Thr Ala Ile Ile Gly Gly Gly Arg Thr Ser Ile Thr
                 85                  90                  95

Phe Pro Thr Asn Thr Leu Ser Lys Asn Val Ser Tyr Thr Phe Phe Cys
                 100                 105                 110

Ser Phe Pro Gly His Trp Ala Leu Met Lys Gly Thr Leu Asn Phe Gly
         115                 120                 125

Gly

<210> SEQ ID NO 14
<211> LENGTH: 138
<212> TYPE: PRT
<213> ORGANISM: Cucumis sativus

<400> SEQUENCE: 14

Met Gln Ser Thr Val His Ile Val Gly Asp Asn Thr Gly Trp Ser Val
 1               5                  10                  15

Pro Ser Ser Pro Asn Phe Tyr Ser Gln Trp Ala Ala Gly Lys Thr Phe
             20                  25                  30

Arg Val Gly Asp Ser Leu Gln Phe Asn Phe Pro Ala Asn Ala His Asn
         35                  40                  45

Val His Glu Met Glu Thr Lys Gln Ser Phe Asp Ala Cys Asn Phe Val
 50                  55                  60

Asn Ser Asp Asn Asp Val Glu Arg Thr Ser Pro Val Ile Glu Arg Leu
 65                  70                  75                  80

Asp Glu Leu Gly Met His Tyr Phe Val Cys Thr Val Gly Thr His Cys
                 85                  90                  95

Ser Asn Gly Gln Lys Leu Ser Ile Asn Val Val Ala Ala Asn Ala Thr
                 100                 105                 110

Val Ser Met Pro Pro Ser Ser Pro Ser Pro Ser Val Met Pro
         115                 120                 125

Pro Pro Val Met Pro Pro Ser Pro Ser
 130                 135

<210> SEQ ID NO 15
<211> LENGTH: 162
<212> TYPE: PRT
<213> ORGANISM: Chloroflexus aurantiacus

<400> SEQUENCE: 15

Met Lys Ile Thr Leu Arg Met Val Leu Ala Val Leu Thr Ala Met
 1               5                  10                  15

Ala Met Val Leu Ala Ala Cys Gly Gly Gly Ser Gly Gly Ser
             20                  25                  30

Thr Gly Gly Gly Ser Gly Ser Gly Pro Val Thr Ile Glu Ile Gly Ser
         35                  40                  45

Lys Gly Glu Glu Leu Ala Phe Asp Lys Thr Glu Leu Thr Val Ser Ala
 50                  55                  60

Gly Gln Thr Val Thr Ile Arg Phe Lys Asn Asn Ser Ala Val Gln Gln
```

```
            65                  70                  75                  80
His Asn Trp Ile Leu Val Lys Gly Gly Glu Ala Glu Ala Ala Asn Ile
                85                  90                  95

Ala Asn Ala Gly Leu Ser Ala Gly Pro Ala Ala Asn Tyr Leu Pro Ala
            100                 105                 110

Asp Lys Ser Asn Ile Ile Ala Glu Ser Pro Leu Ala Asn Gly Asn Glu
            115                 120                 125

Thr Val Glu Val Thr Phe Thr Ala Pro Ala Ala Gly Thr Tyr Leu Tyr
            130                 135                 140

Ile Cys Thr Val Pro Gly His Tyr Pro Leu Met Gln Gly Lys Leu Val
145                 150                 155                 160

Val Asn

<210> SEQ ID NO 16
<211> LENGTH: 140
<212> TYPE: PRT
<213> ORGANISM: Chloroflexus aurantiacus

<400> SEQUENCE: 16

Ala Ala Asn Ala Pro Gly Gly Ser Asn Val Val Asn Glu Thr Pro Ala
1               5                   10                  15

Gln Thr Val Glu Val Arg Ala Ala Pro Asp Ala Leu Ala Phe Ala Gln
            20                  25                  30

Thr Ser Leu Ser Leu Pro Ala Asn Thr Val Val Arg Leu Asp Phe Val
            35                  40                  45

Asn Gln Asn Asn Leu Gly Val Gln His Asn Trp Val Leu Val Asn Gly
        50                  55                  60

Gly Asp Asp Val Ala Ala Val Asn Thr Ala Ala Gln Asn Asn Ala
65                  70                  75                  80

Asp Ala Leu Phe Val Pro Pro Asp Thr Pro Asn Ala Leu Ala Trp
            85                  90                  95

Thr Ala Met Leu Asn Ala Gly Glu Ser Gly Ser Val Thr Phe Arg Thr
            100                 105                 110

Pro Ala Pro Gly Thr Tyr Leu Tyr Ile Cys Thr Phe Pro Gly His Tyr
            115                 120                 125

Leu Ala Gly Met Lys Gly Thr Leu Thr Val Thr Pro
            130                 135                 140

<210> SEQ ID NO 17
<211> LENGTH: 96
<212> TYPE: PRT
<213> ORGANISM: Cucumis sativus

<400> SEQUENCE: 17

Ala Val Tyr Val Val Gly Gly Ser Gly Gly Trp Thr Phe Asn Thr Glu
1               5                   10                  15

Ser Trp Pro Lys Gly Lys Arg Phe Arg Ala Gly Asp Ile Leu Leu Phe
            20                  25                  30

Asn Tyr Asn Pro Ser Met His Asn Val Val Val Val Asn Gln Gly Gly
            35                  40                  45

Phe Ser Thr Cys Asn Thr Pro Ala Gly Ala Lys Val Tyr Thr Ser Gly
        50                  55                  60

Arg Asp Gln Ile Lys Leu Pro Lys Gly Gln Ser Tyr Phe Ile Cys Asn
65                  70                  75                  80

Phe Pro Gly His Cys Gln Ser Gly Met Lys Ile Ala Val Asn Ala Leu
            85                  90                  95
```

<210> SEQ ID NO 18
<211> LENGTH: 166
<212> TYPE: PRT
<213> ORGANISM: Neisseria gonorrhoeae
<220> FEATURE:
<223> OTHER INFORMATION: Neisseria gonorrhoeae F62

<400> SEQUENCE: 18

Cys Ser Gln Glu Pro Ala Ala Pro Ala Glu Ala Thr Pro Ala Gly
1               5                   10                  15

Glu Ala Pro Ala Ser Glu Ala Pro Ala Glu Ala Ala Pro Ala Asp
                20                  25                  30

Ala Ala Glu Ala Pro Ala Ala Gly Asn Cys Ala Ala Thr Val Glu Ser
            35                  40                  45

Asn Asp Asn Met Gln Phe Asn Thr Lys Asp Ile Gln Val Ser Lys Ala
        50                  55                  60

Cys Lys Glu Phe Thr Ile Thr Leu Lys His Thr Gly Thr Gln Pro Lys
65                  70                  75                  80

Ala Ser Met Gly His Asn Leu Val Ile Ala Lys Ala Glu Asp Met Asp
                85                  90                  95

Gly Val Phe Lys Asp Gly Val Gly Ala Ala Asp Thr Asp Tyr Val Lys
                100                 105                 110

Pro Asp Asp Ala Arg Val Val Ala His Thr Lys Leu Ile Gly Gly Gly
                115                 120                 125

Glu Glu Ser Ser Leu Thr Leu Asp Pro Ala Lys Leu Ala Asp Gly Asp
            130                 135                 140

Tyr Lys Phe Ala Cys Thr Phe Pro Gly His Gly Ala Leu Met Asn Gly
145                 150                 155                 160

Lys Val Thr Leu Val Asp
                165

<210> SEQ ID NO 19
<211> LENGTH: 150
<212> TYPE: PRT
<213> ORGANISM: Vibrio parahaemolyticus

<400> SEQUENCE: 19

Met Ser Leu Arg Ile Leu Ala Ala Thr Leu Ala Leu Ala Gly Leu Ser
1               5                   10                  15

Phe Gly Ala Gln Ala Ser Ala Glu Cys Glu Val Ser Ile Asp Ala Asn
                20                  25                  30

Asp Met Met Gln Phe Ser Thr Lys Thr Leu Ser Val Pro Ala Thr Cys
            35                  40                  45

Lys Glu Val Thr Leu Thr Leu Asn His Thr Gly Lys Met Pro Ala Gln
        50                  55                  60

Ser Met Gly His Asn Val Val Ile Ala Asp Thr Ala Asn Ile Gln Ala
65                  70                  75                  80

Val Gly Thr Asp Gly Met Ser Ala Gly Ala Asp Asn Ser Tyr Val Lys
                85                  90                  95

Pro Asp Asp Glu Arg Val Tyr Ala His Thr Lys Val Val Gly Gly Gly
                100                 105                 110

Glu Ser Thr Ser Ile Thr Phe Ser Thr Glu Lys Met Thr Ala Gly Gly
            115                 120                 125

Asp Tyr Ser Phe Phe Cys Ser Phe Pro Gly His Trp Ala Ile Met Gln
            130                 135                 140

Gly Lys Phe Glu Phe Lys
145                 150

<210> SEQ ID NO 20
<211> LENGTH: 33
<212> TYPE: PRT
<213> ORGANISM: Chloroflexus aurantiacus

<400> SEQUENCE: 20

His Asn Trp Val Leu Val Asn Gly Gly Asp Asp Val Ala Ala Val
1               5                   10                  15

Asn Thr Ala Ala Gln Asn Asn Ala Asp Ala Leu Phe Val Pro Pro Pro
            20                  25                  30

Asp

<210> SEQ ID NO 21
<211> LENGTH: 27
<212> TYPE: PRT
<213> ORGANISM: Pseudomonas syringae

<400> SEQUENCE: 21

Ser Lys Lys Ala Asp Ala Ser Ala Ile Thr Thr Asp Gly Met Ser Val
1               5                   10                  15

Gly Ile Asp Lys Asp Tyr Val Lys Pro Asp Asp
            20                  25

<210> SEQ ID NO 22
<211> LENGTH: 27
<212> TYPE: PRT
<213> ORGANISM: Neisseria meningitidis

<400> SEQUENCE: 22

Ile Gly Lys Thr Glu Asp Met Asp Gly Ile Phe Lys Asp Gly Val Gly
1               5                   10                  15

Ala Ala Asp Thr Asp Tyr Val Lys Pro Asp Asp
            20                  25

<210> SEQ ID NO 23
<211> LENGTH: 27
<212> TYPE: PRT
<213> ORGANISM: Vibrio parahaemolyticus

<400> SEQUENCE: 23

Ala Asp Thr Ala Asn Ile Gln Ala Val Gly Thr Asp Gly Met Ser Ala
1               5                   10                  15

Gly Ala Asp Asn Ser Tyr Val Lys Pro Asp Asp
            20                  25

<210> SEQ ID NO 24
<211> LENGTH: 27
<212> TYPE: PRT
<213> ORGANISM: Bordetella bronchiseptica

<400> SEQUENCE: 24

Thr Lys Thr Ala Asp Met Gln Ala Val Glu Lys Asp Gly Ile Ala Ala
1               5                   10                  15

Gly Leu Asp Asn Gln Tyr Leu Lys Ala Gly Asp
            20                  25

<210> SEQ ID NO 25
<211> LENGTH: 18
<212> TYPE: PRT

<213> ORGANISM: Pseudomonas aeruginosa

<400> SEQUENCE: 25

Leu Ser Thr Ala Ala Asp Met Gln Gly Val Val Thr Asp Gly Met Ala
1               5                   10                  15

Ser Gly

<210> SEQ ID NO 26
<211> LENGTH: 53
<212> TYPE: PRT
<213> ORGANISM: Pseudomonas aeruginosa

<400> SEQUENCE: 26

Pro Gly Asn Leu Pro Lys Asn Val Met Gly His Asn Trp Val Leu Ser
1               5                   10                  15

Thr Ala Ala Asp Met Gln Gly Val Val Thr Asp Gly Met Ala Ser Gly
            20                  25                  30

Leu Asp Lys Asp Tyr Leu Lys Pro Asp Asp Ser Arg Val Ile Ala His
        35                  40                  45

Thr Lys Leu Ile Gly
    50

<210> SEQ ID NO 27
<211> LENGTH: 42
<212> TYPE: PRT
<213> ORGANISM: Pseudomonas aeruginosa

<400> SEQUENCE: 27

Pro Gly Asn Leu Pro Lys Asn Val Met Gly His Asn Trp Val Leu Ser
1               5                   10                  15

Thr Ala Ala Asp Met Gln Gly Val Val Thr Asp Gly Met Ala Ser Gly
            20                  25                  30

Leu Asp Lys Asp Tyr Leu Lys Pro Asp Asp
        35                  40

<210> SEQ ID NO 28
<211> LENGTH: 54
<212> TYPE: PRT
<213> ORGANISM: Pseudomonas aeruginosa

<400> SEQUENCE: 28

Pro Gly Asn Leu Pro Lys Asn Val Met Gly His Asn Trp Val Leu Ser
1               5                   10                  15

Thr Ala Ala Asp Met Gln Gly Val Val Thr Asp Gly Met Ala Ser Gly
            20                  25                  30

Leu Asp Lys Asp Tyr Leu Lys Pro Asp Asp Ser Arg Val Ile Ala His
        35                  40                  45

Thr Lys Leu Ile Gly Ser
    50

<210> SEQ ID NO 29
<211> LENGTH: 93
<212> TYPE: PRT
<213> ORGANISM: Pseudomonas aeruginosa

<400> SEQUENCE: 29

Pro Gly Asn Leu Pro Lys Asn Val Met Gly His Asn Trp Val Leu Ser
1               5                   10                  15

Thr Ala Ala Asp Met Gln Gly Val Val Thr Asp Gly Met Ala Ser Gly
            20                  25                  30

```
Leu Asp Lys Asp Tyr Leu Lys Pro Asp Asp Ser Arg Val Ile Ala His
            35                  40                  45

Thr Lys Leu Ile Gly Ser Gly Glu Lys Asp Ser Val Thr Phe Asp Val
    50                  55                  60

Ser Lys Leu Lys Glu Gly Glu Gln Tyr Met Phe Phe Cys Thr Phe Pro
65                  70                  75                  80

Gly His Ser Ala Leu Met Lys Gly Thr Leu Thr Leu Lys
                85                  90
```

<210> SEQ ID NO 30
<211> LENGTH: 18
<212> TYPE: PRT
<213> ORGANISM: Pseudomonas aeruginosa

<400> SEQUENCE: 30

```
Ala Ala Asp Met Gln Gly Val Val Thr Asp Gly Met Ala Ser Gly Leu
1               5                   10                  15

Asp Lys
```

<210> SEQ ID NO 31
<211> LENGTH: 12
<212> TYPE: PRT
<213> ORGANISM: Pseudomonas aeruginosa

<400> SEQUENCE: 31

```
Ala Ala Asp Met Gln Gly Val Val Thr Asp Gly Met
1               5                   10
```

<210> SEQ ID NO 32
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(7)
<223> OTHER INFORMATION: Any amino acid
<220> FEATURE:
<221> NAME/KEY: MOD_RES
<222> LOCATION: (9)..(10)
<223> OTHER INFORMATION: Any amino acid
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (14)..(15)
<223> OTHER INFORMATION: Any amino acid

<400> SEQUENCE: 32

```
Asp Gly Xaa Xaa Xaa Xaa Xaa Asp Xaa Xaa Tyr Xaa Lys Xaa Xaa Asp
1               5                   10                  15
```

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(6)
<223> OTHER INFORMATION: Any amino acid

```
<220> FEATURE:
<221> NAME/KEY: MOD_RES
<222> LOCATION: (8)..(9)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (13)..(14)
<223> OTHER INFORMATION: Any amino acid

<400> SEQUENCE: 33

Asp Gly Xaa Xaa Xaa Xaa Asp Xaa Xaa Tyr Xaa Lys Xaa Xaa Asp
1               5                   10                  15

<210> SEQ ID NO 34
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Pro Gly Asn Leu Pro Lys Asn Val Met Gly His Asn Trp Val Leu Ser
1               5                   10                  15

Thr Ala Ala Asp Met Gln Gly Val Val Thr Asp Gly Met Ala Ser Gly
            20                  25                  30

Leu Asp Lys Asp Tyr Leu Lys Pro Asp Asp Ser Arg Val Ile Ala His
        35                  40                  45

Thr Lys Leu Ile Gly Ser Gly Glu Lys Asp Ser Val Thr Phe Asp Val
    50                  55                  60

Ser Lys Leu Lys Glu Gly Glu Gln Tyr Met Phe Phe Cys Thr Phe Pro
65                  70                  75                  80

Gly His Ser Ala Leu Met Lys Gly Thr Leu Thr Leu Lys
                85                  90

<210> SEQ ID NO 35
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cgggatcccc ggcaacctgc cgaagaacgt catgggc                              37

<210> SEQ ID NO 36
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cggaattcgc atcacttcag ggtcaggg                                        28

<210> SEQ ID NO 37
<211> LENGTH: 15
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 37

Pro Gly Asn Leu Pro Lys Asn Val Met Gly His Asn Trp Val Leu
1               5                   10                  15

<210> SEQ ID NO 38
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Pro Gly Asn Leu Pro Lys Asn Val Met Gly His Asn Trp Val Leu Ser
1               5                   10                  15

Thr Ala Ala Asp Met Gln Gly Val Val Thr Asp Gly Met Ala Ser Gly
            20                  25                  30

Leu Asp Lys Asp Tyr Leu Lys Pro Asp Asp
        35                  40

<210> SEQ ID NO 39
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ccaagctgat cggctcgtga gagaaggact cggtgacc                               38

<210> SEQ ID NO 40
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ggccacaact gggtactgtg aaccgccgcc gacatgcag                              39

<210> SEQ ID NO 41
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ctgcatgtcg gcggcggttc acagtaccca gttgtggcc                              39

<210> SEQ ID NO 42
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
cctgaagccc gacgactgac gtgtcatcgc ccacacc                                37

<210> SEQ ID NO 43
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
ggtgtgggcg atgacacgtc agtcgtcggg cttcagg                              37

<210> SEQ ID NO 44
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
ccaagctgat cggctcgtga gagaaggact cggtgacc                             38

<210> SEQ ID NO 45
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ggtcaccgag tccttctctc acgagccgat cagcttgg                             38

<210> SEQ ID NO 46
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
cgggatcctg agcaccgccg ccgacatgca ggg                                  33

<210> SEQ ID NO 47
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
cgggatcccc ggcctggaca aggattacct gaagcccg                             38

<210> SEQ ID NO 48
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
cggaattcgc atcacttcag ggtcaggg                                        28

<210> SEQ ID NO 49
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
gacggcatgg cttcctgact ggacaaggat tacc                                34

<210> SEQ ID NO 50
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
ggtaatcctt gtccagtcag gaagccatgc cgtc                                34

<210> SEQ ID NO 51
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
cgggatcccc atggtgagca agggcg                                         26

<210> SEQ ID NO 52
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
cggaattcct tgtacagctc gtccatgccg                                     30

<210> SEQ ID NO 53
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ccgctcgagc ctgagcaccg ccgccatgca ggg                                 33

<210> SEQ ID NO 54
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ttttcctttt gcggccgctc agtcgtcggg cttcaggtaa tcc                      43

COMPOSITIONS AND METHODS TO PREVENT CANCER WITH CUPREDOXINS

RELATED APPLICATIONS

This patent application is a continuation of U.S. patent application Ser. No. 12/028,683, filed Feb. 8, 2008, now U.S. Pat. No. 8,232,224, issued on Jul. 31, 2012, which claims benefit under 35 U.S.C. § 119(e) from U.S. Provisional Patent Application Ser. No. 60/900,098, filed Feb. 8, 2007. The entire contents of each of the foregoing patent applications are incorporated herein by reference in their entireties.

STATEMENT OF GOVERNMENTAL INTEREST

The entire content of these prior applications is fully incorporated herein by reference. The subject matter of this application has been supported by research grants from the National Institutes of Health (NIH), Bethesda, Md., U.S.A., (Grant Numbers AI 16790-21, ES 04050-16, AI 45441, CA09432 and N01-CM97567. The government may have certain rights in this invention.

The instant application contains a Sequence Listing which has been submitted electronically in ASCII format and is hereby incorporated by reference in its entirety. Said ASCII copy, created on Dec. 3, 2015, is named 14PR-135588CON-_SL.txt and is 34,865 bytes in size.

FIELD OF THE INVENTION

The present invention relates to compositions comprising variants, derivatives and structural equivalents of cupredoxins that inhibit the development of premalignant lesions in mammalian cells, tissues and animals. The invention also relates to the use of cupredoxins, and variants, derivatives and structurally equivalents of cupredoxins, as chemopreventive agents in mammals to inhibit the development of premalignant lesions, and ultimately cancer.

BACKGROUND

Cancer chemoprevention is the use of natural, synthetic or biologic chemical agents to reverse, suppress, or prevent carcinogenic progression to invasive cancer. Recent clinical trials in preventing cancer in high-risk populations suggest that chemopreventive therapy is a realistic treatment for high-risk patients. Chemopreventive therapy is based on the concepts of multifocal field carcinogenesis and multistep carcinogenesis. In field carcinogenesis, generalized carcinogen exposure throughout the tissue field results in diffuse epithelial injury in tissue and clonal proliferation of the mutated cells. These genetic mutations throughout the field increase the likelihood that one or more premalignant or malignant lesions may develop in the field. Multistep carcinogenesis in the stepwise accumulation of these genetic and phenotypic alterations. Arresting one or more steps in the multistep cancinogenesis may impede or prevent the development of cancer. See generally Tsao et al., CA Cancer J Clin 54:150-180 (2004).

Azurin, and other cupredoxins, are cytotoxic specifically towards cancer cells. Azurin induces apoptosis in J774 lung cancer cells. Yamada et al., PNAS 99(22):14098-14103 (2002). On entry into J774 lung cancer cells, azurin localizes in the cytosol and nuclear fractions, and forms a complex with tumor suppressor protein p53, thereby stabilizing it and enhancing its intracellular level. Id. The induction of azurin-mediated apoptosis is not limited to J774 cells. Azurin can also enter cancer cells such as human melanoma UISO-Mel-2 or human breast cancer MCF-7 cells. Yamada et al., Infect Immun. 70:7054-7062 (2002); Punj et al., Oncogene. 23:2367-2378 (2004). In both cases, azurin allowed the elevation of the intracellular p53 levels, leading to enhanced Bax formation and induction of apoptosis in such cells. Most interestingly, intraperitoneal injection of azurin in nude mice harboring xenografted Mel-2 or MCF-7 human cancers led to statistically significant regression of such cancers. Id.

The mouse mammary gland organ culture (MMOC) assay may be used to evaluate the inhibitory effects of potential chemopreventive agents on both hormone-induced structural differentiation of mammary glands and on the development of DMBA-induced preneoplastic hyperplastic alveolar nodule-like lesions in the gland. Mammary glands from young, virgin animals, when incubated for 6 days in the presence of insulin (I)+prolactin (P)+aldosterone (A), can differentiate into fully-grown glands. These glands morphologically resemble the glands obtained from pregnant mice. Aldosterone can be replaced by estrogen (E)+progesterone (Pg) Inclusion of hydrocortisone (H) to the medium stimulates the functional differentiation of the mammary glands. Mehta and Banerjee, Acta Endocrinol. 80:501 (1975); Mehta and Moon, Breast Cancer: Treatment and Prognosis 300, 300 (Basil A Stoll ed., Blackwell Press 1986). Thus, the hormone-induced structural and functional differentiation, observed in this culture system, mimics the responses to hormones observed during various physiological stages of the animal.

Mice exhibit a distinct preneoplastic stage prior to cancer formation in MMOC. Such preneoplastic lesions in C3H mice are induced by murine mammary tumor virus or in BALB/c mice by DMBA. Exposure of the glands to 2 µg/ml DMBA between days 3 and 4 of growth phases followed by regression of the glands for 2-3 weeks in the medium containing only insulin, results in the formation of mammary alveolar lesions (MAL). Hawthorne et al., Pharmaceutical Biology 40:70-74 (2002); Mehta et al., Methods in Cell Science 19:19-24 (1997). Furthermore, transplantation of epithelial cells, prepared from glands containing the DMBA-induced mammary lesions, into syngeneic host resulted in the development of mammary adenocarcinoma. Telang et al., PNAS 76:5886-5890 (1979). Pathologically, these tumors were similar to those observed in vivo when mice of the same strain are administered DMBA. Id.

DMBA-induced mammary lesion formation in MMOC can be inhibited by a variety of classes of chemopreventive agents such as retinoids. These agents include chemopreventive agents derived from the natural products such as brassinin and resveretrol, thiols, antioxidants, inhibitors of ornithine decarboxylase such as OFMO and deguelin, inhibitors of prostaglandin synthesis, Ca regulators, etc. Jang et al., Science 275:218-220 (1997); Mehta, Eur. J. Cancer 36:1275-1282 (2000); Metha et al., J. Natl. Cancer Inst. 89:212-219 (1997). These studies clearly demonstrate that this organ culture system offers a unique model to determine the effectiveness of compounds against mammary carcinogenesis. The results can be expected to closely correlate to the inhibition obtained by in vivo administration of such compounds.

The MMOC may also be induced to form mammary ductal lesions (MDL). The MDL can be induced if estrogen and progesterone instead of aldosterone and hydrocortisone are included in the medium. The alveolar structures in the presence of ovarian steroids are very small but the intraductal lesions are observed in histopathological sections. Mehta et al., J. Natl. Cancer Inst. 93:1103-1106 (2001). The antiestrogens, which selectively work on ovarian hormone dependent ER+ breast cancers such as tamoxifen, inhibited MDL formation and not MAL. Thus, this modified culture model in addition to conventional MAL induction protocol now can be used to evaluate effects of chemopreventive agents on both MAL and MOL.

What is needed is a chemopreventive agent that inhibits the development of premalignant lesions. Such a chemopreventive agent should be able to either prevent the initial development of premalignant lesions, induce cell death in premalignant lesions that form, and/or prevent the development of premalignant lesions into malignant lesions. Such chemopreventive agents would have great utility in treating, in particular, patients who are at a high risk of developing cancer, due to either the presence of high-risk features, the presence of pre-malignant lesions, or the previous of cancer or premalignant lesions.

The entry of a protein into a mammalian cell is often dictated by a small segment of the protein, which is commonly referred to as a "protein transduction domain" or PTD. This segment can be used as a signal attached to a foreign protein to facilitate transport of such a protein into a mammalian cell. For example, amphipathic peptides are used to facilitate uptake of DNA-cleaving metalloporphyrins as potential antitumor drugs in human fibroblasts HS68 or murine lymphocytic leukemia L1210 cells (Chaloin, L. et al. Bioconjugate Chem. 12:691-700, (2001)). Peptides, called cell-penetrating peptides, such as penetratin, transportan, Tat (amino acids 47-57 or 48-60) and the model amphipathic peptide MAP, have been used as delivery vehicles for transporting pharmacologically important substances, such as antisense oligonucleotides, proteins and peptides (Hallbrink, M. et al. Biochim. Biophys. Acta 1515: 101-109 (2001); Lindgren, M., et al. Trends Pharmacol. Sci. 21:99-103 (2000)).

Such peptides, particularly the DNA-binding homeodomain of Antennapedia, a *Drosophila* transcription factor, or the 21 residue peptide carrier Pep-1, are internalized by many types of cells in culture, such as human HS68 or murine NIH-3T3 fibroblasts, at either 37° C. or 4° C. The lack of effect of the temperature shift suggests a penetration mechanism different from that of classical endocytosis (Morris, M. C. et al. Nature Biotechnol. 19:1173-1176 (2001)), which requires chiral receptor proteins. One of the most widely used peptides to transport pharmacologically-active compounds in mammalian cells is the eleven amino acid arginine-rich protein transduction domain (PTD) of the human immunodeficiency virus type 1 (HIV-1) transactivator protein Tat (Schwarze, S. R. et al. Science 285:1569-1572 (1999), Schwarze, S. R. et al. Trends Cell Biol. 10:290-295 (2000)). Intraperitoneal injection of the 120 kDa beta-galactosidase/Tat fusion protein results in the transcellular transduction of the fusion protein into virtually all tissues in mice, including the passage of the blood-brain barrier. This short peptide domain of HIV-1 Tat has been shown to mediate cell internalization of large molecules or particles, including magnetic nanoparticles, phage vectors, liposomes and plasmid DNA. Unlike the other cell-penetrating peptides discussed above, internalization of cargo proteins by full length Tat or its 11 amino acid transduction domain is significantly impaired at 4° C. (Liu, Y. et al. Nat. Med. 6:1380-1387 (2000), Suzuki, T. et al. J. Biol. Chem. 277:2437-2443 (2002)) and requires interactions with receptors such as the heparan sulfate chains of the cell membrane heparan sulfate proteoglycans.

Most of the PTDs identified to date have been derived from viral and mammalian sources. Other sources of PTDs would be desirable for the design of various experimental sequences, and for animal and human therapies and prophylactic procedures. One alternative source of PTDs is bacterial cells. Although bacterial proteins such as cholera toxin are known to enter mammalian cell cytosol (Sofer, A. and Futerman, A. H. J. Biol. Chem. 270:12117-12122 (1995)), the cytotoxicity of such proteins has limited the use of bacterial proteins, or PTDs derived from them, for transporting pharmacologically important cargos in mammalian cells.

SUMMARY OF THE EMBODIMENTS

The present invention relates to compositions comprising peptides that may be variants, derivatives and structural equivalents of cupredoxins that inhibit the development of premalignant lesions in mammalian cells, tissues and animals. Specifically, these compositions may comprise azurin from *Pseudomonas aeruginosa*, the 50-77 residue region of azurin (p28) SEQ ID NO: 2, and the 50-67 residue region of azurin (p18) SEQ ID NO: 25. The present invention further relates to compositions that may comprise cupredoxin(s), and/or variants, derivatives or structural equivalents of cupredoxins, that retain the ability to inhibit the development of premalignant lesions in mammalian cells, tissues or animals. These compositions may be isolated peptides or pharmaceutical compositions, among others. The compositions of the invention may be used in methods to prevent the development of cancer in mammalian patients.

One aspect of the invention are isolated peptides that may be a variant, derivative or structural equivalent of a cupredoxin; and may inhibit the development of premalignant lesions in mammalian tissue. The cupredoxin may be azurin, pseudoazurin, plastocyanin, rusticyanin, Laz, auracyanin, stellacyanin and cucumber basic protein, and specifically may be azurin. The cupredoxin may be from an organism such as *Pseudomonas aeruginosa, Alcaligenes faecalis, Ulva pertussis, Achromobacter xylosoxidan, Bordetella bronchiseptica, Methylomonas* sp., *Neisseria meningitidis, Neisseria gonorrhea, Pseudomonas fluorescens, Pseudomonas chloroaphis, Xylella fastidiosa* and *Vibrio parahaemolyticus*, and specifically may be *Pseudomonas aeruginosa*. In some embodiments, the peptide may be part of SEQ ID NOS: 1, 3-19, or has at least 80% amino acid sequence identity to SEQ ID NOS: 1, 3-19.

In some embodiments, the isolated peptide may be a truncation of a cupredoxin. The isolated peptide may be more than about 10 residues and not more than about 100 residues. The isolated peptide may comprise, or alternatively consist of, *Pseudomonas aeruginosa* azurin residues 50-77 SEQ ID NO: 2, *Pseudomonas aeruginosa* azurin residues 50-67 SEQ ID NO: 25, *Pseudomonas aeruginosa* azurin residues 36-88 SEQ ID NO. 26, or SEQ ID NOS: 20-24.

Another aspect of the invention is a pharmaceutical composition that may comprise at least one, or two, cupredoxins or isolated peptides of the invention in a pharmaceutically acceptable carrier. The pharmaceutical composition may be formulated for intravenous administration. In some embodiments, the cupredoxin in the pharmaceutical composition may be from an organism such as *Pseudomonas aeruginosa, Ulva pertussis, Alcaligenes faecalis, Achromobacter xylosoxidan, Bordetella bronchiseptica, Methylomonas* sp., *Neisseria meningitidis, Neisseria gonorrhea, Pseudomonas fluorescens, Pseudomonas chloroaphis, Xylella fastidiosa* and *Vibrio parahaemolyticus*, and specifically may be from *Pseudomonas aeruginosa*. The cupredoxin may be SEQ ID NOS: 1, 3-19.

Another aspect of the invention is a method to treat a mammalian patient by administering to the patient a therapeutically effective amount of the pharmaceutical composition of the invention. The patient may be human, and may be at a higher risk to develop cancer than the general population. In some embodiments, the cancer may be melanoma, breast, pancreas, glioblastoma, astrocytoma, lung, colorectal, neck and head, bladder, prostate, skin, or cervical cancer. In some embodiments, the patient may have at least one high risk feature, premalignant lesions or have been cured of cancer or premalignant lesions.

The pharmaceutical composition may be administered by intravenous injection, intramuscular injection, subcutaneous injection, inhalation, topical administration, transdermal patch, suppository, vitreous injection or oral, and specifically may be administered by intravenous injection. The pharmaceutical composition may be co-administered with at least one other chemopreventive drug, and specifically at about the same time as another chemopreventive drug.

Another aspect of the invention is a kit comprising the pharmaceutical composition of the invention in a vial. The kit may be designed for intravenous administration.

Another aspect of the invention is a method to study the development of cancer comprising contacting mammalian cells with a cupredoxin or peptide of the invention and measuring the development of premalignant and malignant cells. In some embodiments, the cells may be human and/or mammary cells. In some embodiments, the cells are induced to develop premalignant lesions.

Another aspect of the invention is an expression vector, which encodes a peptide of the invention.

Another aspect of the invention is a complex comprising a cargo compound and an amino acid sequence, where the amino acid sequence has at least about 90% sequence identity with a cupredoxin, or a fragment thereof, the amino acid sequence, or fragment thereof, is linked to the cargo compound, and the amino acid sequence facilitates entry of the cargo compound into a mammalian cancer cell. In some embodiments, the amino acid sequence of this complex has at least about 90% amino acid sequence identity to less than a full length wild-type cupredoxin or H.8 outer membrane protein. In other embodiments, the cargo compound is protein, lipoprotein, polypeptide, peptide, polysaccharide, nucleic acid, dye, microparticle, nanoparticle, toxin and drug. In particular embodiments, the cargo is a protein or polypeptide which is linked amino acid sequence to form a fusion protein. In other particular embodiments, the cargo compound is a toxin, more particularly, the *Pseudomonas aeruginosa* exotoxin A. In other embodiments, the cargo is a detectable substance, more specifically one detectable by fluorimetry, microscopy, X-ray CT, MRI or ultrasound. Finally, the invention also encompasses the complex in a pharmaceutically suitable carrier.

Another aspect of the present invention is directed to a method for delivering a cargo compound into a cell. In one embodiment, this method comprises contacting a cell or cells with the above complex. In other embodiments, the cell or cells originate from a patient suffering from cancer, and are reintroduced into the patient. In other embodiments, the cells is a cancer cell, more specifically an osteosarcoma cell, lung carcinoma cell, colon carcinoma cell, lymphoma cell, leukemia cell, soft tissue sarcoma cell, breast carcinoma cell, liver carcinoma cell, bladder carcinoma cell or prostate carcinoma cell. In other embodiments, the complex is administered to a patient in a therapeutically effective amount. In other embodiments, the complex is administered intravenously, topically, subcutaneously, intramuscularly or into a tumor. In other embodiments, the complex is co-administered with another cancer treatment. In yet other embodiments, RNAi approaches, drug resistance, hematopoietic gene transfer, homologous recombination, ribozyme technology, antisense technology, tumor immunotherapy and tumor suppressors, translational research, cancer therapy, gene delivery systems (viral and non-viral), anti-gene therapy (antisense, siRNA & ribozymes), apoptosis; mechanisms and therapies, vaccine development, immunology and immunotherapy, and DNA synthesis and repair are used in the context of delivering DNA and/or RNA as cargo compounds in the complexes of the present invention. In a particular embodiment, the cargo compound is an antisense molecule.

Another aspect of the invention is a method to diagnose cancer. In some embodiments, the complex with a cargo that is a detectable substance is administered to a patient with cancer and the location of the cargo is detected. In particular embodiments, the cargo compound is an X-ray contrast agent and is detected by X-ray CT, the cargo compound is a magnetic resonance imaging contrast agent and is detected by MRI, and the cargo is an ultrasound contrast agent and is detectable by ultrasound. In other embodiments, the a cell or cells are contacted with a complex with a detectable substance and the location of the cargo is detected.

Another aspect of the invention is a kit that contains any of the above complexes. In some embodiments, the kit further comprises a pharmaceutically acceptable adjuvant or excipient. In other embodiments, the kit further comprises a vehicle for administration of the reagent.

These and other aspects, advantages, and features of the invention will become apparent from the following figures and detailed description of the specific embodiments.

BRIEF DESCRIPTION OF THE SEQUENCES

SEQ ID NO: 1. Amino acid sequence of azurin from *Pseudomonas aeruginosa* (Ala Glu Cys Ser Val Asp Ile Gln Gly Asn Asp Gln Met Gln Phe Asn Thr Asn Ala Ile Thr Val Asp Lys Ser Cys Lys Gln Phe Thr Val Asn Leu Ser His Pro Gly Asn Leu Pro Lys Asn Val Met Gly His Asn Trp Val Leu Ser Thr Ala Ala Asp Met Gln Gly Val Val Thr Asp Gly Met Ala Ser Gly Leu Asp Lys Asp Tyr Leu Lys Pro Asp Asp Ser Arg Val Ile Ala His Thr Lys Leu Ile Gly Ser Gly Glu Lys Asp Ser Val Thr Phe Asp Val Ser Lys Leu Lys Glu Gly Glu Gln Tyr Met Phe Phe Cys Thr Phe Pro Gly His Ser Ala Leu Met Lys Gly Thr Leu Thr Leu Lys).

SEQ ID NO: 2. Amino acid sequence of p28, *Pseudomonas aeruginosa* azurin residues 50-77 (Leu Ser Thr Ala Ala Asp Met Gln Gly Val Val Thr Asp Gly Met Ala Ser Gly Leu Asp Lys Asp Tyr Leu Lys Pro Asp Asp).

SEQ ID NO: 3. Amino acid sequence of plastocyanin from *Phormidium laminosum* (Glu Thr Phe Thr Val Lys Met Gly Ala Asp Ser Gly Leu Leu Gln Phe Glu Pro Ala Asn Val Thr Val His Pro Gly Asp Thr Val Lys Trp Val Asn Asn Lys Leu Pro Pro His Asn Ile Leu Phe Asp Asp Lys Gln Val Pro Gly Ala Ser Lys Glu Leu Ala Asp Lys Leu Ser His Ser Gln Leu Met Phe Ser Pro Gly Glu Ser Tyr Glu Ile Thr Phe Ser Ser Asp Phe Pro Ala Gly Thr Tyr Thr Tyr Tyr Cys Ala Pro His Arg Gly Ala Gly Met Val Gly Lys Ile Thr Val Glu Gly).

SEQ ID NO: 4. Amino acid sequence of rusticyanin from *Thiobacillus ferrooxidans* (Gly Thr Leu Asp Thr Thr Trp Lys Glu Ala Thr Leu Pro Gln Val Lys Ala Met Leu Glu Lys Asp Thr Gly Lys Val Ser Gly Asp Thr Val Thr Tyr Ser Gly Lys Thr Val His Val Val Ala Ala Ala Val Leu Pro Gly Phe Pro Phe Pro Ser Phe Glu Val His Asp Lys Lys Asn Pro Thr Leu Glu Ile Pro Ala Gly Ala Thr Val Asp Val Thr Phe Ile Asn Thr Asn Lys Gly Phe Gly His Ser Phe Asp Ile Thr Lys Lys Gly Pro Pro Tyr Ala Val Met Pro Val Ile Asp Pro Ile Val Ala Gly Thr Gly Phe Ser Pro Val Pro Lys Asp Gly Lys Phe Gly Tyr Thr Asp Phe Thr Trp His Pro Thr Ala Gly Thr Tyr Tyr Tyr Val Cys Gln Ile Pro Gly His Ala Ala Thr Gly Met Phe Gly Lys Ile Val Val Lys).

SEQ ID NO: 5. Amino acid sequence of pseudoazurin from *Achromobacter cycloclastes* (Ala Asp Phe Glu Val His Met Leu Asn Lys Gly Lys Asp Gly Ala Met Val Phe Glu Pro Ala Ser Leu Lys Val Ala Pro Gly Asp Thr Val Thr Phe Ile Pro Thr Asp Lys Gly His Asn Val Glu Thr Ile Lys Gly Met Ile Pro Asp Gly Ala Glu Ala Phe Lys Ser Lys Ile Asn Glu Asn Tyr Lys Val Thr Phe Thr Ala Pro Gly Val Tyr Gly Val Lys Cys Thr Pro His Tyr Gly Met Gly Met Val Gly Val Val Gln Val Gly Asp Ala Pro Ala Asn Leu Glu Ala Val Lys Gly Ala Lys Asn Pro Lys Lys Ala Gln Glu Arg Leu Asp Ala Ala Leu Ala Ala Leu Gly Asn).

SEQ ID NO: 6. Amino acid sequence of azurin from *Alcaligenes faecalis* (Ala Cys Asp Val Ser Ile Glu Gly Asn Asp Ser Met Gln Phe Asn Thr Lys Ser Ile Val Val Asp Lys Thr Cys Lys Glu Phe Thr Ile Asn Leu Lys His Thr Gly Lys Leu Pro Lys Ala Ala Met Gly His Asn Val Val Val Ser Lys Lys Ser Asp Glu Ser Ala Val Ala Thr Asp Gly Met Lys Ala Gly Leu Asn Asn Asp Tyr Val Lys Ala Gly Asp Glu Arg Val Ile Ala His Thr Ser Val Ile Gly Gly Gly Glu Thr Asp Ser Val Thr Phe Asp Val Ser Lys Leu Lys Glu Gly Glu Asp Tyr Ala Phe Phe Cys Ser Phe Pro Gly His Trp Ser Ile Met Lys Gly Thr Ile Glu Leu Gly Ser).

SEQ ID NO: 7. Amino acid sequence of azurin from *Achromobacter xylosoxidans* ssp. *denitrificans* I (Ala Gln Cys Glu Ala Thr Ile Glu Ser Asn Asp Ala Met Gln Tyr Asn Leu Lys Glu Met Val Val Asp Lys Ser Cys Lys Gln Phe Thr Val His Leu Lys His Val Gly Lys Met Ala Lys Val Ala Met Gly His Asn Trp Val Leu Thr Lys Glu Ala Asp Lys Gln Gly Val Ala Thr Asp Gly Met Asn Ala Gly Leu Ala Gln Asp Tyr Val Lys Ala Gly Asp Thr Arg Val Ile Ala His Thr Lys Val Ile Gly Gly Gly Glu Ser Asp Ser Val Thr Phe Asp Val Ser Lys Leu Thr Pro Gly Glu Ala Tyr Ala Tyr Phe Cys Ser Phe Pro Gly His Trp Ala Met Met Lys Gly Thr Leu Lys Leu Ser Asn).

SEQ ID NO: 8. Amino acid sequence of azurin from *Bordetella bronchiseptica* (Ala Glu Cys Ser Val Asp Ile Ala Gly Thr Asp Gln Met Gln Phe Asp Lys Lys Ala Ile Glu Val Ser Lys Ser Cys Lys Gln Phe Thr Val Asn Leu Lys His Thr Gly Lys Leu Pro Arg Asn Val Met Gly His Asn Trp Val Leu Thr Lys Thr Ala Asp Met Gln Ala Val Glu Lys Asp Gly Ile Ala Ala Gly Leu Asp Asn Gln Tyr Leu Lys Ala Gly Asp Thr Arg Val Leu Ala His Thr Lys Val Leu Gly Gly Gly Glu Ser Asp Ser Val Thr Phe Asp Val Ala Lys Leu Ala Ala Gly Asp Asp Tyr Thr Phe Phe Cys Ser Phe Pro Gly His Gly Ala Leu Met Lys Gly Thr Leu Lys Leu Val Asp).

SEQ ID NO: 9. Amino acid sequence of azurin from *Methylomonas* sp. J (Ala Ser Cys Glu Thr Thr Val Thr Ser Gly Asp Thr Met Thr Tyr Ser Thr Arg Ser Ile Ser Val Pro Ala Ser Cys Ala Glu Phe Thr Val Asn Phe Glu His Lys Gly His Met Pro Lys Thr Gly Met Gly His Asn Trp Val Leu Ala Lys Ser Ala Asp Val Gly Asp Val Ala Lys Glu Gly Ala His Ala Gly Ala Asp Asn Asn Phe Val Thr Pro Gly Asp Lys Arg Val Ile Ala Phe Thr Pro Ile Ile Gly Gly Gly Glu Lys Thr Ser Val Lys Phe Lys Val Ser Ala Leu Ser Lys Asp Glu Ala Tyr Thr Tyr Phe Cys Ser Tyr Pro Gly His Phe Ser Met Met Arg Gly Thr Leu Lys Leu Glu Glu).

SEQ ID NO: 10. Amino acid sequence of azurin from *Neisseria meningitidis* Z2491 (Cys Ser Gln Glu Pro Ala Ala Pro Ala Ala Glu Ala Thr Pro Ala Ala Glu Ala Pro Ala Ser Glu Ala Pro Ala Ala Glu Ala Ala Pro Ala Asp Ala Ala Glu Ala Pro Ala Ala Gly Asn Cys Ala Ala Thr Val Glu Ser Asn Asp Asn Met Gln Phe Asn Thr Lys Asp Ile Gln Val Ser Lys Ala Cys Lys Glu Phe Thr Ile Thr Leu Lys His Thr Gly Thr Gln Pro Lys Thr Ser Met Gly His Asn Ile Val Ile Gly Lys Thr Glu Asp Met Asp Gly Ile Phe Lys Asp Gly Val Gly Ala Ala Asp Thr Asp Tyr Val Lys Pro Asp Asp Ala Arg Val Val Ala His Thr Lys Leu Ile Gly Gly Gly Glu Glu Ser Ser Leu Thr Leu Asp Pro Ala Lys Leu Ala Asp Gly Glu Tyr Lys Phe Ala Cys Thr Phe Pro Gly His Gly Ala Leu Met Asn Gly Lys Val Thr Leu Val Asp).

SEQ ID NO: 11. Amino acid sequence of azurin from *Pseudomonas fluorescen* (Ala Glu Cys Lys Thr Thr Ile Asp Ser Thr Asp Gln Met Ser Phe Asn Thr Lys Ala Ile Glu Ile Asp Lys Ala Cys Lys Thr Phe Thr Val Glu Leu Thr His Ser Gly Ser Leu Pro Lys Asn Val Met Gly His Asn Leu Val Ile Ser Lys Gln Ala Asp Met Gln Pro Ile Ala Thr Asp Gly Leu Ser Ala Gly Ile Asp Lys Asn Tyr Leu Lys Glu Gly Asp Thr Arg Val Ile Ala His Thr Lys Val Ile Gly Ala Gly Glu Lys Asp Ser Leu Thr Ile Asp Val Ser Lys Leu Asn Ala Ala Glu Lys Tyr Gly Phe Phe Cys Ser Phe Pro Gly His Ile Ser Met Met Lys Gly Thr Val Thr Leu Lys).

SEQ ID NO: 12. Amino acid sequence of azurin from *Pseudomonas chlororaphis* (Ala Glu Cys Lys Val Asp Val Asp Ser Thr Asp Gln Met Ser Phe Asn Thr Lys Glu Ile Thr Ile Asp Lys Ser Cys Lys Thr Phe Thr Val Asn Leu Thr His Ser Gly Ser Leu Pro Lys Asn Val Met Gly His Asn Trp Val Leu Ser Lys Ser Ala Asp Met Ala Gly Ile Ala Thr Asp Gly Met Ala Ala Gly Ile Asp Lys Asp Tyr Leu Lys Pro Gly Asp Ser Arg Val Ile Ala His Thr Lys Ile Ile Gly Ser Gly Glu Lys Asp Ser Val Thr Phe Asp Val Ser Lys Leu Thr Ala Gly Glu Ser Tyr Glu Phe Phe Cys Ser Phe Pro Gly His Asn Ser Met Met Lys Gly Ala Val Val Leu Lys).

SEQ ID NO: 13. Amino acid sequence of azurin from *Xylella fastidiosa* 9a5c (Lys Thr Cys Ala Val Thr Ile Ser Ala Asn Asp Gln Met Lys Phe Asp Gln Asn Thr Ile Lys Ile Ala Ala Glu Cys Thr His Val Asn Leu Thr Leu Thr His Thr Gly Lys Lys Ser Ala Arg Val Met Gly His Asn Trp Val Leu Thr Lys Thr Thr Asp Met Gln Ala Val Ala Leu Ala Gly Leu His Ala Thr Leu Ala Asp Asn Tyr Val Pro Lys Ala Asp Pro Arg Val Ile Ala His Thr Ala Ile Ile Gly Gly Gly Glu Arg Thr Ser Ile Thr Phe Pro Thr Asn Thr Leu Ser Lys Asn Val Ser Tyr Thr Phe Phe Cys Ser Phe Pro Gly His Trp Ala Leu Met Lys Gly Thr Leu Asn Phe Gly Gly).

SEQ ID NO: 14. Amino acid sequence of stellacyanin from *Cucumis sativus* (Met Gln Ser Thr Val His Ile Val Gly Asp Asn Thr Gly Trp Ser Val Pro Ser Ser Pro Asn Phe Tyr Ser Gln Trp Ala Ala Gly Lys Thr Phe Arg Val Gly Asp Ser Leu Gln Phe Asn Phe Pro Ala Asn Ala His Asn Val His Glu Met Glu Thr Lys Gln Ser Phe Asp Ala Cys Asn Phe Val Asn Ser Asp Asn Asp Val Glu Arg Thr Ser Pro Val Ile Glu Arg Leu Asp Glu Leu Gly Met His Tyr Phe Val Cys Thr Val Gly Thr His Cys Ser Asn Gly Gln Lys Leu Ser Ile Asn Val Val Ala Ala Asn Ala Thr Val Ser Met Pro Pro Ser Ser Ser Pro Pro Ser Ser Val Met Pro Pro Val Met Pro Pro Ser Pro Ser).

SEQ ID NO: 15. Amino acid sequence of auracyanin A from *Chloroflexus aurantiacus* (Met Lys Ile Thr Leu Arg Met Met Val Leu Ala Val Leu Thr Ala Met Ala Met Val Leu Ala Ala Cys Gly Gly Gly Gly Ser Ser Gly Gly Ser Thr Gly Gly Gly Ser Gly Ser Gly Pro Val Thr Ile Glu Ile Gly Ser Lys Gly Glu Glu Leu Ala Phe Asp Lys Thr Glu Leu Thr Val Ser Ala Gly Gln Thr Val Thr Ile Arg Phe Lys Asn Asn Ser Ala Val Gln His Ile His Asn Trp Ile Leu Val Lys Gly Gly Glu Ala Glu Ala Ala Asn Ile Ala Asn Ala Gly Leu Ser Ala Gly Pro Ala Ala Asn Tyr Leu Pro Ala Asp Lys Ser Asn Ile Ile Ala Glu Ser Pro Leu Ala Asn Gly Asn Glu Thr Val Glu Val Thr Phe Thr Ala Pro Ala Ala Gly Thr Tyr Leu Tyr Ile Cys Thr Val Pro Gly His Tyr Pro Leu Met Gln Gly Lys Leu Val Val Asn).

SEQ ID NO: 16. Amino acid sequence of auracyanin B from *Chloroflexus aurantiacus* (Ala Ala Asn Ala Pro Gly Gly Ser Asn Val Val Asn Glu Thr Pro Ala Gln Thr Val Glu Val Arg Ala Ala Pro Asp Ala Leu Ala Phe Ala Gln Thr Ser Leu Ser Leu Pro Ala Asn Thr Val Val Arg Leu Asp Phe Val Asn Gln Asn Asn Leu Gly Val Gln His Asn Trp Val Leu Val Asn Gly Gly Asp Asp Val Ala Ala Ala Val Asn Thr Ala Ala Gln Asn Asn Ala Asp Ala Leu Phe Val Pro Pro Pro Asp Thr Pro Asn Ala Leu Ala Trp Thr Ala Met Leu Asn Ala Gly Glu Ser Gly Ser Val Thr Phe Arg Thr Pro Ala Pro Gly Thr Tyr Leu Tyr Ile Cys Thr Phe Pro Gly His Tyr Leu Ala Gly Met Lys Gly Thr Leu Thr Val Thr Pro).

SEQ ID NO: 17. Amino acid sequence of cucumber basic protein from *Cucumis sativus* (Ala Val Tyr Val Val Gly Gly Ser Gly Gly Trp Thr Phe Asn Thr Glu Ser Trp Pro Lys Gly Lys Arg Phe Arg Ala Gly Asp Ile Leu Leu Phe Asn Tyr Asn Pro Ser Met His Asn Val Val Val Val Asn Gln Gly Gly Phe Ser Thr Cys Asn Thr Pro Ala Gly Ala Lys Val Tyr Thr Ser Gly Arg Asp Gln Ile Lys Leu Pro Lys Gly Gln Ser Tyr Phe Ile Cys Asn Phe Pro Gly His Cys Gln Ser Gly Met Lys Ile Ala Val Asn Ala Leu).

SEQ ID NO: 18. Amino acid sequence of Laz from *Neisseria gonorrhoeae* F62 (Cys Ser Gln Glu Pro Ala Ala Pro Ala Ala Glu Ala Thr Pro Ala Gly Glu Ala Pro Ala Ser Glu Ala Pro Ala Ala Glu Ala Ala Pro Ala Asp Ala Ala Glu Ala Pro Ala Ala Gly Asn Cys Ala Ala Thr Val Glu Ser Asn Asp Asn Met Gln Phe Asn Thr Lys Asp Ile Gln Val Ser Lys Ala Cys Lys Glu Phe Thr Ile Thr Leu Lys His Thr Gly Thr Gln Pro Lys Ala Ser Met Gly His Asn Leu Val Ile Ala Lys Ala Glu Asp Met Asp Gly Val Phe Lys Asp Gly Val Gly Ala Ala Asp Thr Asp Tyr Val Lys Pro Asp Asp Ala Arg Val Val Ala His Thr Lys Leu Ile Gly Gly Gly Glu Glu Ser Ser Leu Thr Leu Asp Pro Ala Lys Leu Ala Asp Gly Asp Tyr Lys Phe Ala Cys Thr Phe Pro Gly His Gly Ala Leu Met Asn Gly Lys Val Thr Leu Val Asp).

SEQ ID NO: 19. Amino acid sequence of the azurin from *Vibrio parahaemolyticus* (Met Ser Leu Arg Ile Leu Ala Ala Thr Leu Ala Leu Ala Gly Leu Ser Phe Gly Ala Gln Ala Ser Ala Glu Cys Glu Val Ser Ile Asp Ala Asn Asp Met Met Gln Phe Ser Thr Lys Thr Leu Ser Val Pro Ala Thr Cys Lys Glu Val Thr Leu Thr Leu Asn His Thr Gly Lys Met Pro Ala Gln Ser Met Gly His Asn Val Val Ile Ala Asp Thr Ala Asn Ile Gln Ala Val Gly Thr Asp Gly Met Ser Ala Gly Ala Asp Asn Ser Tyr Val Lys Pro Asp Asp Glu Arg Val Tyr Ala His Thr Lys Val Val Gly Gly Gly Glu Ser Thr Ser Ile Thr Phe Ser Thr Glu Lys Met Thr Ala Gly Gly Asp Tyr Ser Phe Phe Cys Ser Phe Pro Gly His Trp Ala Ile Met Gln Gly Lys Phe Glu Phe Lys).

SEQ ID NO: 20. Amino acid sequence of amino acids 57 to 89 of auracyanin B of *Chloroflexus aurantiacus* (His Asn Trp Val Leu Val Asn Gly Gly Asp Asp Val Ala Ala Ala Val Asn Thr Ala Ala Gln Asn Asn Ala Asp Ala Leu Phe Val Pro Pro Pro Asp).

SEQ ID NO: 21. Amino acid sequence of amino acids 51-77 of *Pseudomonas syringae* azurin (Ser Lys Lys Ala Asp Ala Ser Ala Ile Thr Thr Asp Gly Met Ser Val Gly Ile Asp Lys Asp Tyr Val Lys Pro Asp Asp).

SEQ ID NO: 22. Amino acid sequence of amino acids 89-115 of *Neisseria meningitidis* Laz (Ile Gly Lys Thr Glu Asp Met Asp Gly Ile Phe Lys Asp Gly Val Gly Ala Ala Asp Thr Asp Tyr Val Lys Pro Asp Asp).

SEQ ID NO: 23. Amino acid sequence of amino acids 52-78 of *Vibrio parahaemolyticus* azurin (Ala Asp Thr Ala Asn Ile Gln Ala Val Gly Thr Asp Gly Met Ser Ala Gly Ala Asp Asn Ser Tyr Val Lys Pro Asp Asp).

SEQ ID NO: 24. Amino acid sequence of amino acids 51-77 of *Bordetella bronchiseptica* azurin (Thr Lys Thr Ala Asp Met Gln Ala Val Glu Lys Asp Gly Ile Ala Ala Gly Leu Asp Asn Gln Tyr Leu Lys Ala Gly Asp).

SEQ ID NO: 25. Amino acid sequence of p18, *Pseudomonas aeruginosa* azurin residues 50-67 (Leu Ser Thr Ala Ala Asp Met Gln Gly Val Val Thr Asp Gly Met Ala Ser Gly).

SEQ ID NO: 26. Amino acid sequence of amino acids 36-88 of *Pseudomonas aeruginosa* azurin (Pro Gly Asn Leu Pro Lys Asn Val Met Gly His Asn Trp Val Leu Ser Thr Ala Ala Asp Met Gln Gly Val Val Thr Asp Gly Met Ala Ser Gly Leu Asp Lys Asp Tyr Leu Lys Pro Asp Asp Ser Arg Val Ile Ala His Thr Lys Leu Ile Gly).

SEQ ID NO: 27. Amino acid sequence of amino acids 36 to 77 of *Pseudomonas aeruginosa* azurin (Pro Gly Asn Leu Pro Lys Asn Val Met Gly His Asn Trp Val Leu Ser Thr Ala Ala Asp Met Gln Gly Val Val Thr Asp Gly Met Ala Ser Gly Leu Asp Lys Asp Tyr Leu Lys Pro Asp Asp).

SEQ ID NO: 28. Amino acid sequence of amino acids 36 to 89 of *Pseudomonas aeruginosa* azurin (Pro Gly Asn Leu Pro Lys Asn Val Met Gly His Asn Trp Val Leu Ser Thr Ala Ala Asp Met Gln Gly Val Val Thr Asp Gly Met Ala Ser Gly Leu Asp Lys Asp Tyr Leu Lys Pro Asp Asp Ser Arg Val Ile Ala His Thr Lys Leu Ile Gly Ser).

SEQ ID NO: 29. Amino acid sequence of amino acids 36 to 128 of *Pseudomonas aeruginosa* azurin (Pro Gly Asn Leu Pro Lys Asn Val Met Gly His Asn Trp Val Leu Ser Thr Ala Ala Asp Met Gln Gly Val Val Thr Asp Gly Met Ala Ser Gly Leu Asp Lys Asp Tyr Leu Lys Pro Asp Asp Ser Arg Val Ile Ala His Thr Lys Leu Ile Gly Ser Gly Glu Lys Asp Ser Val Thr Phe Asp Val Ser Lys Leu Lys Glu Gly Glu Gln Tyr Met Phe Phe Cys Thr Phe Pro Gly His Ser Ala Leu Met Lys Gly Thr Leu Thr Leu Lys).

SEQ ID NO: 30. Amino acid sequence of amino acids 53 to 70 of *Pseudomonas aeruginosa* azurin (Ala Ala Asp Met Gln Gly Val Val Thr Asp Gly Met Ala Ser Gly Leu Asp Lys).

SEQ ID NO: 31. Amino acid sequence of amino acids 53 to 64 of *Pseudomonas aeruginosa* azurin (Ala Ala Asp Met Gln Gly Val Val Thr Asp Gly Met).

SEQ ID NO: 32. Amino acid sequence DGXXXXXDXXYXKXXD.

SEQ ID NO: 33. Amino acid sequence DGXXXXDXXYXKXXD.

BRIEF DESCRIPTION OF THE FIGURES

FIG. 1 depicts photographs of all of the glands evaluated for the efficacy of p28 and azurin.

DETAILED DESCRIPTION OF THE INVENTION

Definitions

Figure 1A:
FIG. 1A shows a representative photograph of alveolar lesions in a DMBA-treated gland and its comparison with a gland that was treated with DMBA along with a chemopreventive agent.
Figure 1A:

As used herein, the term "cell" includes either the singular or the plural of the term, unless specifically described as a "single cell."

As used herein, the terms "polypeptide," "peptide," and "protein" are used interchangeably to refer to a polymer of amino acid residues. The terms apply to amino acid polymers in which one or more amino acid residue is an artificial chemical analogue of a corresponding naturally occurring amino acid. The terms also apply to naturally occurring amino acid polymers. The terms "polypeptide," "peptide," and "protein" are also inclusive of modifications including, but not limited to, glycosylation, lipid attachment, sulfation, gamma-carboxylation of glutamic acid residues, hydroxylation and ADP-ribosylation. It will be appreciated that polypeptides are not always entirely linear. For instance, polypeptides may be branched as a result of ubiquitination and they may be circular (with or without branching), generally as a result of post-translation events, including natural processing event and events brought about by human manipulation which do not occur naturally. Circular, branched and branched circular polypeptides may be synthesized by non-translation natural process and by entirely synthetic methods as well.

As used herein, the term "pharmacologic activity" means the effect of a drug or other chemical on a biological system. The effect of chemical may be beneficial (therapeutic) or harmful (toxic). The pure chemicals or mixtures may be of natural origin (plant, animal, or mineral) or may be synthetic compounds.

As used herein, the term "premalignant" means precancerous, or before abnormal cells divide without control.

As used herein, the term "lesion" means an area of abnormal tissue.

As used herein, the term "pathological condition" includes anatomic and physiological deviations from the normal that constitute an impairment of the normal state of the living animal or one of its parts, that interrupts or modifies the performance of the bodily functions, and is a response to various factors (as malnutrition, industrial hazards, or climate), to specific infective agents (as worms, parasitic protozoa, bacteria, or viruses), to inherent defects of the organism (as genetic anomalies), or to combinations of these factors.

As used herein, the term "condition" includes anatomic and physiological deviations from the normal that constitute an impairment of the normal state of the living animal or one of its parts, that interrupts or modifies the performance of the bodily functions.

As used herein, the term "suffering from" includes presently exhibiting the symptoms of a pathological condition, having a pathological condition even without observable symptoms, in recovery from a pathological condition, or recovered from a pathological condition.

As used herein, the term "chemoprevention" is the use of drugs, vitamins, or other agents to try to reduce the risk of, or delay the development or recurrence of, cancer.

A used herein, the term "treatment" includes preventing, lowering, stopping, or reversing the progression or severity of the condition or symptoms associated with a condition being treated. As such, the term "treatment" includes medical, therapeutic, and/or prophylactic administration, as appropriate. Treatment may also include preventing or lessening the development of a condition, such as cancer.

As used herein, the term "inhibit cell growth" means the slowing or ceasing of cell division and/or cell expansion. This term also includes the inhibition of cell development or increases in cell death.

A "therapeutically effective amount" is an amount effective to prevent, lower, stop or reverse the development of, or to partially or totally alleviate the existing symptoms of a particular condition for which the subject being treated. Determination of a therapeutically effective amount is well within the capability of those skilled in the art.

The term "substantially pure," as used herein, when used to modify a protein or other cellular product of the invention, refers to, for example, a protein isolated from the growth medium or cellular contents, in a form substantially free of, or unadulterated by, other proteins and/or other compounds. The term "substantially pure" refers to a factor in an amount of at least about 75%, by dry weight, of isolated fraction, or at least "75% substantially pure." More specifically, the term "substantially pure" refers to a compound of at least about 85%, by dry weight, of isolated fraction, or at least "85% substantially pure." Most specifically, the term "substantially pure" refers to a compound of at least about 95%, by dry weight, of isolated fraction, or at least "95% substantially pure." The term "substantially pure" may also be used to modify a synthetically-made protein or compound of the invention, where, for example, the synthetic protein is isolated from the reagents and by-products of the synthesis reaction(s).

The term "pharmaceutical grade," as used herein, when referring to a peptide or compound of the invention, is a peptide or compound that is isolated substantially or essentially from components which normally accompany the material as it is found in its natural state, including synthesis reagents and by-products, and substantially or essentially isolated from components that would impair its use as a pharmaceutical. For example, a "pharmaceutical grade" peptide may be isolated from any carcinogen. In some instances, "pharmaceutical grade" may be modified by the intended method of administration, such as "intravenous pharmaceutical grade," in order to specify a peptide or compound that is substantially or essentially isolated from any substance that would render the composition unsuitable for intravenous administration to a patient. For example, an "intravenous pharmaceutical grade" peptide may be isolated from detergents, such as SDS, and anti-bacterial agents, such as azide.

The terms "isolated," "purified" or "biologically pure" refer to material which is substantially or essentially free from components which normally accompany the material as it is found in its native state. Thus, isolated peptides in accordance with the invention preferably do not contain materials normally associated with the peptides in their in situ environment. An "isolated" region of a polypeptide refers to a region that does not include the whole sequence of the polypeptide from which the region was derived. An "isolated" nucleic acid, protein, or respective fragment thereof has been substantially removed from its in vivo environment so that it may be manipulated by the skilled artisan, such as but not limited to, nucleotide sequencing, restriction digestion, site-directed mutagenesis, and subcloning into expression vectors for a nucleic acid fragment as well as obtaining the protein or protein fragment in substantially pure quantities.

The term "variant" as used herein with respect to a peptide, refers to amino acid sequence variants which may have amino acids replaced, deleted, or inserted as compared to the wild-type polypeptide. Variants may be truncations of the wild-type peptide. A "deletion" is the removal of one or more amino acids from within the polypeptide, which a "truncation" is the removal of one or more amino acids from one or both ends of the polypeptide. Thus, a variant peptide may be made by manipulation of genes encoding the polypeptide. A variant may be made by altering the basic composition or characteristics of the polypeptide, but not at least some of its pharmacologic activities. For example, a "variant" of azurin can be a mutated azurin that retains its ability to inhibit the development of premalignant mammalian cells. In some cases, a variant peptide is synthesized with non-natural amino acids, such as ε-(3,5-dinitrobenzoyl)-Lys residues. Ghadiri & Fernholz, J. Am. Chem. Soc., 112:9633-9635 (1990). In some embodiments, the variant has not more than 20 amino acids replaced, deleted or inserted compared to wild-type peptide or part thereof. In some embodiments, the variant has not more than 15 amino acids replaced, deleted or inserted compared to wild-type peptide or part thereof. In some embodiments, the variant has not more than 10 amino acids replaced, deleted or inserted compared to wild-type peptide or part thereof. In some embodiments, the variant has not more than 6 amino acids replaced, deleted or inserted compared to wild-type peptide or part thereof. In some embodiments, the variant has not more than 5 amino acids replaced, deleted or inserted compared to wild-type peptide or part thereof. In some embodiments, the variant has not more than 3 amino acids replaced, deleted or inserted compared to wild-type peptide or part thereof.

The term "amino acid," as used herein, means an amino acid moiety that comprises any naturally-occurring or non-naturally occurring or synthetic amino acid residue, i.e., any moiety comprising at least one carboxyl and at least one amino residue directly linked by one, two three or more carbon atoms, typically one (a) carbon atom.

The term "derivative" as used herein with respect to a peptide refers to a peptide that is derived from the subject peptide. A derivation includes chemical modifications of the peptide such that the peptide still retains some of its fundamental activities. For example, a "derivative" of azurin can, for example, be a chemically modified azurin that retains its ability to inhibit angiogenesis in mammalian cells. Chemical modifications of interest include, but are not limited to, amidation, acetylation, sulfation, polyethylene glycol (PEG) modification, phosphorylation or glycosylation of the peptide. In addition, a derivative peptide may be a fusion of a polypeptide or fragment thereof to a chemical compound, such as but not limited to, another peptide, drug molecule or other therapeutic or pharmaceutical agent or a detectable probe.

The term "percent (%) amino acid sequence identity" is defined as the percentage of amino acid residues in a polypeptide that are identical with amino acid residues in a candidate sequence when the two sequences are aligned. To determine % amino acid identity, sequences are aligned and if necessary, gaps are introduced to achieve the maximum % sequence identity; conservative substitutions are not considered as part of the sequence identity. Amino acid sequence alignment procedures to determine percent identity are well known to those of skill in the art. Often publicly available computer software such as BLAST, BLAST2, ALIGN2 or Megalign (DNASTAR) software is used to align peptide sequences. In a specific embodiment, Blastp (available from the National Center for Biotechnology Information, Bethesda Md.) is used using the default parameters of long complexity filter, expect 10, word size 3, existence 11 and extension 1.

When amino acid sequences are aligned, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) can be calculated as:

$$\% \text{ amino acid sequence identity} = X/Y*100$$

where
X is the number of amino acid residues scored as identical matches by the sequence alignment program's or algorithm's alignment of A and B and
Y is the total number of amino acid residues in B.

If the length of amino acid sequence A is not equal to the length of amino acid sequence B, the % amino acid sequence identity of A to B will not equal the % amino acid sequence identity of B to A. When comparing longer sequences to shorter sequences, the shorter sequence will be the "B" sequence. For example, when comparing truncated peptides to the corresponding wild-type polypeptide, the truncated peptide will be the "B" sequence.

General

The present invention provides compositions comprising cupredoxin, and variants, derivatives and structural equivalents of cupredoxins, and methods to prevent the development of cancer in mammals. The invention also provides to variants, derivatives and structural equivalents of cupredoxin that retain the ability to prevent the development of cancer or the re-occurrence of cancer in mammals. Most particularly, the invention provides compositions comprising *Pseudomonas aeruginosa* azurin, variants, derivatives and structural equivalents of azurin, and their use to treat patients, and particularly patients at a higher risk of developing cancer than the general population. Finally, the invention provides methods to study the development of cancer in mammalian cells, tissues and animals by contacting the cells with a cupredoxin, or variant, derivative or structural equivalent thereof, before or after inducing premalignant lesions, and observing the development of premalignant and/or malignant cells.

Previously, it was known that a redox protein elaborated by *Pseudomonas aerugisnosa*, the cupredoxin azurin, selectively enters J774 lung cancer cells but not normal cells, and induces apoptosis. Zaborina et al., Microbiology 146:2521-2530 (2000). Azurin can also selectively enter and kill human melanoma UISO-Mel-2 or human breast cancer MCF-7 cells. Yamada et al., PNAS 99:14098-14103 (2002); Punj et al., Oncogene 23:2367-2378 (2004). Azurin from *P. aeruginosa* preferentially enters J774 murine reticulum cell sarcoma cells, forms a complex with and stabilizes the tumor suppressor protein p53, enhances the intracellular concentration of p53, and induces apoptosis. Yamada et al., Infection and Immunity 70:7054-7062 (2002). Detailed studies of various domains of the azurin molecule showed that amino acids 50-77 (p28) (SEQ ID NO: 2) represented a protein transduction domain (PTD) critical for internalization and subsequent apoptotic activity. Yamada et al., Cell. Microbial. 7:1418-1431 (2005).

It is now known that azurin, and peptides derived from azurin, such as p28 and p18, have chemopreventive properties. It is now known that azurin, p28, prevent formation of premalignant preneoplastic lesions in mouse mammary gland organ culture. In a mouse mammary gland organ culture model, azurin at 50 μg/ml was found to inhibit the formation of alveolar lesions by 67%. Likewise, p28 at 25 μg/ml was found to inhibit the formation of alveolar lesions by 67%. See Example 1. Further, azurin at 50 μg/ml was found to inhibit the formation of ductal lesions by 79%, and p28 at 25 μg/ml inhibited the formation of ductal lesions by 71%. See Example 1. Confocal microscopy and FAC showed that azurin and p28 entered normal murine mammary epithelial cells (MM3MG) and mammary cancer cells (4T1). P28 also entered human umbilical vein endothelial cells (HUVEC) in a temperature, time and concentration dependent manner and inhibited capillary tube formation of HUVEC plated on Matrigel® in a dose dependent manner. Confocal microscopy and FAC also showed that p18 selectively entered human melanoma (Mel-2,7,29), breast (MCF-7), ovarian (SK-OV3), pancreatic (CAPAN-2), glioblastoma (LN-229), astrocytoma (CCF-STTG1), prostate (LN-CAP), and kidney (ACHN-CRL1611) cell lines. In addition, Imaging of p18 labeled with an infrared dye ($\lambda_{em}$ 800 nm) in athymic mice bearing xenografted melanoma tumors clearly demonstrated selective uptake in primary s.c. tumors and distant organ metastases without accumulating in normal organs and tissues. It is therefore now known that azurin and variants of azurin may be used to inhibit the formation of premalignant preneoplastic lesions, and thus the development of cancer, and specifically breast cancer, in mammalian patients.

Standard cancer treatment methods, including radiotherapy and chemotherapy, involve damaging the DNA of the cancer cell. The cellular response to normal DNA damage includes activation of DNA repair, cell cycle arrest and lethality (Hall, *Radiobiology for the Radiologist*, Harper and Row, 1988). For example, the induction of DNA double-strand breaks results in lethal chromosomal aberrations that include deletions, dicentrics, rings, and anaphase bridges (Hall, *Radiobiology for the Radiologist*, Harper and Row, 1994).

Because of the selective uptake of the peptides of the present invention by tumors and various cancer cells, it is now known that these peptides, including in one embodiment, p18 may have use as a non-viral vector for introducing materials into tumors and cancer cells. For example, the peptides of the present invention may be used to introduce DNA or RNA fragments into a cancer cell thereby providing a therapeutic DNA or RNA fragment treatment to a tumor or cancer cell.

The following describe non-limiting exemplary techniques and/or particular DNA or RNA fragments that can be introduced with the peptides of the present invention, and, in one embodiment, p18, which facilitate the entry of a linked molecule into a mammalian cancer cell. For example, the present invention can be used with gene therapy, RNAi approaches, hematopoietic gene transfer, homologous recombination, ribozyme technology, antisense technology, tumor immunotherapy and tumor suppressors, translational research, anti-gene therapy (antisense, siRNA & ribozymes), apoptosis, immunology and immunotherapy, DNA synthesis and repair.

Gene therapy involves the transfer of a foreign gene into a cancer cell, for example a tumor suppressor or inducer of apoptosis, under conditions suitable for expression of the gene. Once expressed, the gene product confers a beneficial effect on the tumor cell by either slowing its growth, inhibiting its metastatic potential, or killing it outright. Historically, the clinical effectiveness of cancer gene therapy has been limited by 1) lack of control of therapeutic gene expression within the tumor, and 2) selective targeting of the vector to the tumor. The compounds of the present invention address the selective targeting of tumor cells. Moreover, several strategies have been proposed for the control of gene expression. One strategy is transcriptional targeting in which the promoter regulating the therapeutic gene is activated by tumor-selective transcription factors. Examples include the use of the MUC-1 promoter in breast cancer and the CEA promoter in colon cancer (Kurihara et al., "Selectivity of a replication-component adenovirus for human breast carcinoma cells expressing the MUC1 antigen," *J. Clin. Invest.* 106(6): 763-771, 2000; Konishi et al., "Transcriptionally targeted in vivo gene therapy for carcinoembrionic antigen-producing adenocarcinoma," *J. Med. Sci.*, 48(3): 79-89, 1999).

Antisense techniques rely on the introduction of a nucleic acid molecule into a cell which typically is complementary to a mRNA expressed by the selected gene. The antisense molecule typically suppresses translation of the mRNA molecule and prevents the expression of the polypeptide encoded by the gene. Modifications of the antisense technique may prevent the transcription of the selected gene by the antisense molecule binding to the gene's DNA to form a triple helix. One particular antisense drug that can be used in accordance with the present invention is G3139 (also known as oblimersen; manufactured by Genta, Inc., Lexington, Mass.). Another particular antisense molecule that can be used is G4460 (also known as c-myb antisense manufactured by Genta, Berkeley Heights, N.J.).

RNA interference (RNAi) based molecules can also be attached to the peptides of the present invention. RNAi is generally mediated by double stranded RNA ("dsRNA"), short hairpin RNA ("shRNA") or other nucleic acid molecules with similar characteristics. These nucleic acid molecules are processed or cut into smaller pieces by cellular enzymes including Dicer and Drosha. The smaller fragments of the nucleic acid molecules can then be taken up by a protein complex (the RISC complex) that mediates degradation of mRNAs. The RISC complex will degrade mRNA that complementarily base pairs with the nucleic acid molecules it has taken up. In this manner, the mRNA is specifically destroyed, thus preventing encoded-for proteins from being made.

Ribozyme technologies rely on the introduction of a nucleic acid molecule into a cell which expresses a RNA molecule which binds to, and catalyses the selective cleavage of, a target RNA molecule. The target RNA molecule is typically a mRNA molecule, but it may be, for example, a retroviral RNA molecule.

Targeted gene deletion by homologous recombination, which requires two gene-inactivating events (one for each allele) is also a strategy that can be used with the present invention.

Particular therapies delivered in conjunction with the compounds of the present invention can also be directed against cancer-specific transcription complexes (CSTCs) that can control expression of proteins that are critical for cancer development. See, for example, United States Patent Application No. 2008/0027002 which is incorporated by reference herein for its teachings regarding cancer therapies directed against CSTCs.

Due to the high degree of structural similarity between cupredoxins, it is likely that other cupredoxins will inhibit the formation of premalignant lesions in mammals as well as azurin. Such cupredoxins may be found in, for example, bacteria or plants. Several cupredoxins are known to have pharmacokinetic activities similar to those of azurin from *Pseudomonas aeruginosa*. For example, rusticyanin from *Thiobacillus ferrooxidans* can also enter macrophages and induce apoptosis. Yamada et al., Cell Cycle 3:1182-1187 (2004); Yamada et al., Cell. Micro. 7:1418-1431 (2005). Plastocyanin from *Phormidium laminosum* and pseudoazurin form *Achromobacter cycloclastes* also are cytotoxic towards macrophages. U.S. Pat. Pub. No. 20060040269, published Feb. 23, 2006. It is therefore contemplated that other cupredoxins may be used in the compositions and methods of the invention. Further, variants, derivatives, and structural equivalents of cupredoxins that retain the ability to inhibit the formation of cancer in mammals may also be used in the compositions and methods of the invention. These variants and derivatives may include, but are not limited to, truncations of a cupredoxin, conservative substitutions of amino acids and proteins modifications such as PEGylation and all-hydrocarbon stabling of α-helices.

Compositions of the Invention

The invention provides for peptides that are variants, derivatives or structural equivalents of cupredoxin that inhibit the development of premalignant lesions in mammalian cells, tissues and animals. The invention further provides for peptides that are variants, derivatives or structural equivalents of cupredoxin that inhibit the development of cancer in mammalian cells, tissues and animals. In some embodiments, the peptide is isolated. In some embodiments, the peptide is substantially pure or pharmaceutical grade. In other embodiments, the peptide is in a composition that comprises, or consists essentially of, the peptide. In another specific embodiment, the peptide is non-antigenic and does not raise an immune response in a mammal, and more specifically a human. In some embodiments, the peptide is less that a full-length cupredoxin, and retains some of the pharmacologic activities of the cupredoxins. Specifically, in some embodiments, the peptide may retain the ability to inhibit the development of premalignant lesions in the mouse mammary gland organ culture.

The invention also provides compositions comprising at least one peptide that is a cupredoxin, or variant, derivative or structural equivalent of a cupredoxin, specifically in a pharmaceutical composition. In specific embodiments, the pharmaceutical composition is designed for a particular mode of administration, for example, but not limited to, oral, intraperitoneal, or intravenous. Such compositions may be hydrated in water, or may be dried (such as by lyophilization) for later hydration. Such compositions may be in solvents other than water, such as but not limited to, alcohol.

The invention also provides compositions comprising peptides that are variants, derivatives or structural equivalents of cupredoxin that selectively enter cancer cells and/or tumors in mammalian cells, tissues and animals. In some embodiments, the peptide is p18 having SEQ ID NO. 25. In some embodiments, the peptide is a variant, derivative or structural equivalent of p18. In some embodiments, the composition is p18 coupled to DNA or RNA. In some embodiments, the DNA or RNA is a gene or a portion of a gene. In some embodiments, the DNA or RNA has a therapeutic effect once delivered.

Because of the high structural homology between the cupredoxins, it is contemplated that cupredoxins will have the same chemopreventive properties as azurin and p28. In some embodiments, the cupredoxin is, but is not limited to, azurin, pseudoazurin, plastocyanin, rusticyanin, auracyanin, stellacyanin, cucumber basic protein or Laz. In particularly specific embodiments, the azurin is derived from *Pseudomonas aeruginosa, Alcaligenes faecalis, Achromobacter xylosoxidans* ssp. *denitrificans* I, *Bordetella bronchiseptica, Methylomonas* sp., *Neisseria meningitidis, Neisseria gonorrhea, Pseudomonas fluorescens, Pseudomonas chlororaphis, Xylella fastidiosa, Ulva pertussis* or *Vibrio parahaemolyticus*. In a very specific embodiment, the azurin is from *Pseudomonas aeruginosa*. In other specific embodiments, the cupredoxin comprises an amino acid sequence that is SEQ ID NO: 1, 3-19.

The invention provides peptides that are amino acid sequence variants which have amino acids replaced, deleted, or inserted as compared to the wild-type cupredoxin. Variants of the invention may be truncations of the wild-type cupredoxin. In some embodiments, the peptide of the invention comprises a region of a cupredoxin that is less that the full length wild-type polypeptide. In some embodiments, the peptide of the invention comprises more than about 10 residues, more than about 15 residues or more than about 20 residues of a truncated cupredoxin. In some embodiments, the peptide comprises not more than about 100 residues, not more than about 50 residues, not more than about 40 residues, not more than about 30 residues or not more than about 20 residues of a truncated cupredoxin. In some embodiments, a cupredoxin has to the peptide, and more specifically SEQ ID NOS: 1, 3-19 as to the peptide of the invention, at least about 70% amino acid sequence identity, at least about 80% amino acid sequence identity, at least about 90% amino acid sequence identity, at least about 95% amino acid sequence identity or at least about 99% amino acid sequence identity.

In specific embodiments, the variant of cupredoxin comprises *P. aeruginosa* azurin residues 50-77 (p28, SEQ ID NO: 2), azurin residues 50-67 (p18, SEQ ID NO: 25), or azurin residues 36-88 (SEQ ID NO: 26). In other embodiments, the variant of cupredoxin consists of *P. aeruginosa* azurin residues 50-77 (SEQ ID NO: 2), azurin residues 50-67 (SEQ ID NO: 25), or azurin residues 36-88 (SEQ ID NO: 26). In other specific embodiments, the variant consists of the equivalent residues of a cupredoxin other that azurin. It is also contemplated that other cupredoxin variants can be designed that have a similar pharmcologic activity to azurin residues 50-77 (SEQ ID NO: 2), or azurin residues 36-88 (SEQ ID NO: 26). To do this, the subject cupredoxin amino acid sequence will be aligned to the *Pseudomonas aeruginosa* azurin sequence using BLAST, BLAST2, ALIGN2 or Megalign (DNASTAR), the relevant residues located on the *P. aeruginosa* azurin amino acid sequence, and the equivalent residues found on the subject cupredoxin sequence, and the equivalent peptide thus designed.

In one embodiment of the invention, the cupredoxin variant contains at least amino acids 57 to 89 of auracyanin B of *Chloroflexus aurantiacus* (SEQ ID NO: 20). In another embodiment, the cupredoxin variant contains at least amino acids 50-67 of *Pseudomonas aeruginosa* azurin (SEQ ID NO 25). In another embodiment of the invention, the cupredoxin variant contains at least amino acids 51-77 of *Pseudomonas syringae* azurin (SEQ ID NO: 21). In another embodiment of the invention, the cupredoxin variant contains at least amino acids 89-115 of *Neisseria meningitidis* Laz (SEQ ID NO: 22). In another embodiment of the invention, the cupredoxin variant contains at least amino acids 52-78 of *Vibrio parahaemolyticus* azurin (SEQ ID NO: 23). In another embodiment of the invention, the cupredoxin variant contains at least amino acids 51-77 of *Bordetella bronchiseptica* azurin (SEQ ID NO: 24).

The variants may also include peptides made with synthetic amino acids not naturally occurring. For example, non-naturally occurring amino acids may be integrated into the variant peptide to extend or optimize the half-life of the composition in the bloodstream. Such variants include, but are not limited to, D,L-peptides (diastereomer), (for example Futaki et al., J. Biol. Chem. 276(8):5836-40 (2001); Papo et al., Cancer Res. 64(16):5779-86 (2004); Miller et al, Biochem. Pharmacol. 36(1):169-76, (1987); peptides containing unusual amino acids (for example Lee et al., J. Pept. Res. 63(2):69-84 (2004)), olefin-containing non-natural amino acid followed by hydrocarbon stapling (for example Schafineister et al., J. Am. Chem. Soc. 122:5891-5892 (2000); Walenski et al., Science 305:1466-1470 (2004)), and peptides comprising ε-(3,5-dinitrobenzoyl)-Lys residues.

In other embodiments, the peptide of the invention is a derivative of a cupredoxin. The derivatives of cupredoxin are chemical modifications of the peptide such that the peptide still retains some of its fundamental activities. For example, a "derivative" of azurin can be a chemically modified azurin that retains its ability to inhibit the development of premalignant lesions in mammalian cells, tissues or animals. Chemical modifications of interest include, but are not limited to, hydrocarbon stabling, amidation, acetylation, sulfation, polyethylene glycol (PEG) modification, phosphorylation and glycosylation of the peptide. In addition, a derivative peptide maybe a fusion of a cupredoxin, or variant, derivative or structural equivalent thereof to a chemical compound, such as but not limited to, another peptide, drug molecule or other therapeutic or pharmaceutical agent or a detectable probe. Derivatives of interest include chemical modifications by which the half-life in the bloodstream of the peptides and compositions of the invention can be extended or optimized, such as by several methods well known to those in the art, including but not limited to, circularized peptides (for example Monk et al., BioDrugs 19(4):261-78, (2005); DeFreest et al., J. Pept. Res. 63(5):409-19 (2004)), N- and C-terminal modifications (for example Labrie et al., Clin. Invest. Med. 13(5):275-8, (1990)), and olefin-containing non-natural amino acid followed by hydrocarbon stapling (for example Schafineister et al., J. Am. Chem. Soc. 122:5891-5892 (2000); Walenski et al., Science 305:1466-1470 (2004)).

In another embodiment, the peptide is a structural equivalent of a cupredoxin. Examples of studies that determine significant structural homology between cupredoxins and other proteins include Toth et al. (Developmental Cell 1:82-92 (2001)). Specifically, significant structural homology between a cupredoxin and the structural equivalent may be determined by using the VAST algorithm. Gibrat et al., Curr Opin Struct Biol 6:377-385 (1996); Madej et al., Proteins 23:356-3690 (1995). In specific embodiments, the VAST p value from a structural comparison of a cupredoxin to the structural equivalent may be less than about $10^{-3}$, less than about $10^{-5}$, or less than about $10^{-7}$. In other embodiments, significant structural homology between a cupredoxin and the structural equivalent may be determined by using the DALI algorithm. Holm & Sander, J. Mol. Biol. 233:123-138 (1993). In specific embodiments, the DALI Z score for a pairwise structural comparison is at least about 3.5, at least about 7.0, or at least about 10.0.

It is contemplated that the peptides of the composition of invention may be more than one of a variant, derivative and/or structural equivalent of a cupredoxin. For example, the peptides may be a truncation of azurin that has been PEGylated, thus making it both a variant and a derivative. In one embodiment, the peptides of the invention are synthesized with α,α-disubstituted non-natural amino acids containing olefin-bearing tethers, followed by an all-hydrocarbon "staple" by ruthenium catalyzed olefin metathesis. Scharmeister et al., J. Am. Chem. Soc. 122:5891-5892 (2000); Walensky et al., Science 305:1466-1470 (2004). Additionally, peptides that are structural equivalents of azurin may be fused to other peptides, thus making a peptide that is both a structural equivalent and a derivative. These examples are merely to illustrate and not to limit the invention. Variants, derivatives or structural equivalents of cupredoxin may or may not bind copper.

In some embodiments, the cupredoxin, or variant, derivative or structural equivalent thereof has some of the pharmacologic activities of the *P. aeruginosa* azurin, and specifically p28. In a specific embodiment, the cupredoxins and variants, derivatives and structural equivalents of cupredoxins that may inhibit prevent the development of premalignant lesions in mammalian cells, tissues or animals, and specifically but not limited to, mammary gland cells. The invention also provides for the cupredoxins and variants, derivatives and structural equivalents of cupredoxins that may have the ability to inhibit the development of mammalian premalignant lesions, and specifically but not limited to, melanoma, breast, pancreas, glioblastoma, astrocytoma, lung, colorectal, neck and head, bladder, prostate, skin and cervical cancer cells. Inhibition of the development of cancer cells is any decrease, or lessening of the rate of increase, of the development of premalignant lesions that is statistically significant as compared to control treatments.

Because it is now known that cupredoxins can inhibit the development of premalignant lesions and ultimately cancer in mammalian cells, tissues or animals, and specifically breast cells, and more specifically, mouse mammary gland cells, it is now possible to design variants and derivatives of cupredoxins that retain this chemopreventive activity. Such variants, derivatives and structural equivalents can be made by, for example, creating a "library" of various variants, derivatives and structural equivalents of cupredoxins and cupredoxin derived peptides and then testing each for chemopreventive activity, and specifically chemopreventive activity in the mouse mammary gland organ culture using one of many methods known in the art, such the exemplary method in Example 1. It is contemplated that the resulting variants, derivatives and structural equivalents of cupredoxins with chemopreventive activity may be used in the methods of the invention, in place of or in addition to azurin or p28.

In some specific embodiments, the variant, derivative or structural equivalent of cupredoxin may inhibit the development of 7,12-dimethylbenz (a) anthracene (DMBA) induced premalignant lesions in a mouse mammary gland organ culture (MMOC) to a degree that is statistically different from a non-treated control. A peptide can be tested for this activity by using the MMOC model system is described in Example 1, or as in Mehta et al. (J Natl Cancer Inst 93:1103-1106 (2001)) and Mehta et al. (Meth Cell Sci 19:19-24 (1997)). Other methods to determine whether cancer development is inhibited another are well known in the art and may be used as well.

In some specific embodiments, the variant, derivative or structural equivalent of cupredoxin inhibits the development of mammary alveolar lesions (MAL) in the a MMOC model to a degree that is statistically different from a non-treated control. In some specific embodiments, the variant, derivative or structural equivalent of cupredoxin inhibits the development of mammary ductal lesions (MDL) in the a MMOC model to a degree that is statistically different from a non-treated control. A peptide can be tested for these activities by using the MMOC model system induced to form premalignant lesions by DMBA, as described in Example 1. Evaluation of development of premalignant lesions in a MMOC model system may be determined by morphometic analysis, or histopathological analysis, as provided in Example 1.

In some specific embodiments, the variant, derivative or structural equivalent can selectively enter cancer cells and/or tumors in mammalian cells, tissues and animals. In some embodiments, the variant is a derivative or structural equivalent of p18. In some embodiments, the variant, derivative or structural equivalent can selectively enter cancer cells and/or tumors in mammalian cells, tissues and animals and deliver DNA or RNA. In some embodiments, the DNA or RNA is a gene or a portion of a gene. In some embodiments, the DNA or RNA has a therapeutic effect once delivered.

Cupredoxins

These small blue copper proteins (cupredoxins) are electron transfer proteins (10-20 kDa) that participate in bacterial electron transfer chains or are of unknown function. The copper ion is solely bound by the protein matrix. A special distorted trigonal planar arrangement to two histidine and one cysteine ligands around the copper gives rise to very peculiar electronic properties of the metal site and an intense blue color. A number of cupredoxins have been crystallographically characterized at medium to high resolution.

The cupredoxins in general have a low sequence homology but high structural homology. Gough & Clothia, Structure 12:917-925 (2004); De Rienzo et al., Protein Science 9:1439-1454 (2000). For example, the amino acid sequence of azurin is 31% identical to that of auracyanin B, 16.3% to that of rusticyanin, 20.3% to that of plastocyanin, and 17.3% to that of pseudoazurin. See, Table 1. However, the structural similarity of these proteins is more pronounced. The VAST p value for the comparison of the structure of azurin to auracyanin B is $10^{-7.4}$, azurin to rusticyanin is $10^{-5}$, azurin to plastocyanin is $10^{-5.6}$, and azurin to psuedoazurin is $10^{-4.1}$.

All of the cupredoxins possess an eight-stranded Greek key beta-barrel or beta-sandwich fold and have a highly conserved site architecture. De Rienzo et al., Protein Science 9:1439-1454 (2000). A prominent hydrophobic patch, due to the presence of many long chain aliphatic residues such as methionines and leucines, is present around the copper site in azurins, amicyanins, cyanobacterial plastocyanins, cucumber basic protein and to a lesser extent, pseudoazurin and eukaryotic plastocyanins Id. Hydrophobic patches are also found to a lesser extent in stellacyanin and rusticyanin copper sites, but have different features. Id.

TABLE 1

Sequence and structure alignment of azurin (1JZG) from *P. aeruginosa* to other proteins using VAST algorithm.

| PDB | Alignment length[1] | % aa identity | P-value[2] | Score[3] | RMSD[4] | Description |
| --- | --- | --- | --- | --- | --- | --- |
| 1AOZ A 2 | 82 | 18.3 | 10e-7 | 12.2 | 1.9 | Ascorbate oxidase |
| 1QHQ_A | 113 | 31 | 10e-7.4 | 12.1 | 1.9 | AuracyaninB |
| 1V54 B 1 | 79 | 20.3 | 10e-6.0 | 11.2 | 2.1 | Cytocrome c oxidase |
| 1GY2 A | 92 | 16.3 | 10e-5.0 | 11.1 | 1.8 | Rusticyanin |
| 3MSP A | 74 | 8.1 | 10e-6.7 | 10.9 | 2.5 | Motile Major Sperm Protein[5] |
| 1IUZ | 74 | 20.3 | 10e-5.6 | 10.3 | 2.3 | Plastocyanin |

TABLE 1-continued

Sequence and structure alignment of azurin (1JZG) from *P. aeruginosa* to other proteins using VAST algorithm.

| PDB | Alignment length[1] | % aa identity | P-value[2] | Score[3] | RMSD[4] | Description |
|---|---|---|---|---|---|---|
| 1KGY E | 90 | 5.6 | 10e−4.6 | 10.1 | 3.4 | Ephrinb2 |
| 1PMY | 75 | 17.3 | 10e−4.1 | 9.8 | 2.3 | Pseudoazurin |

[1]Aligned Length: The number of equivalent pairs of C-alpha atoms superimposed between the two structures, i.e. how many residues have been used to calculate the 3D superposition.
[2]P-VAL: The VAST p value is a measure of the significance of the comparison, expressed as a probability. For example, if the p value is 0.001, then the odds are 1000 to 1 against seeing a match of this quality by pure chance. The p value from VAST is adjusted for the effects of multiple comparisons using the assumption that there are 500 independent and unrelated types of domains in the MMDB database. The p value shown thus corresponds to the p value for the pairwise comparison of each domain pair, divided by 500.
[3]Score: The VAST structure-similarity score. This number is related to the number of secondary structure elements superimposed and the quality of that superposition. Higher VAST scores correlate with higher similarity.
[4]RMSD: The root mean square superposition residual in Angstroms. This number is calculated after optimal superposition of two structures, as the square root of the mean square distances between equivalent C-alpha atoms. Note that the RMSD value scales with the extent of the structural alignments and that this size must be taken into consideration when using RMSD as a descriptor of overall structural similarity.
[5]*C. elegans* major sperm protein proved to be an ephrin antagonist in ocyte maturation. Kuwabara, Genes and Development 17: 155-161 (2003).

Azurin

The azurins are copper containing proteins of 128 amino acid residues which belong to the family of cupredoxins involved in electron transfer in certain bacteria. The azurins include those from *P. aeruginosa* (PA) (SEQ ID NO: 1), *A. xylosoxidans*, and *A. denitrificans*. Murphy et al., J. Mol. Biol. 315:859-871 (2002). The amino acid sequence identity between the azurins varies between 60-90%, these proteins showed a strong structural homology. All azurins have a characteristic β-sandwich with Greek key motif and the single copper atom is always placed at the same region of the protein. In addition, azurins possess an essentially neutral hydrophobic patch surrounding the copper site. Id.

Plastocyanins

The plastocyanins are soluble proteins of cyanobacteria, algae and plants that contain one molecule of copper per molecule and are blue in their oxidized form. They occur in the chloroplast, where they function as electron carriers. Since the determination of the structure of poplar plastocyanin in 1978, the structure of algal (*Scenedesmus, Enteromorpha, Chlamydomonas*) and plant (French bean) plastocyanins has been determined either by crystallographic or NMR methods, and the poplar structure has been refined to 1.33 Å resolution. SEQ ID NO: 3 shows the amino acid sequence of plastocyanin from *Phormidium laminosum*, a thermophilic cyanobacterium. Another plastocyanin of interest is from *Ulva pertussis*.

Despite the sequence divergence among plastocyanins of algae and vascular plants (e.g., 62% sequence identity between the *Chlamydomonas* and poplar proteins), the three-dimensional structures are conserved (e.g., 0.76 Å rms deviation in the C alpha positions between the *Chlamydomonas* and *Poplar* proteins). Structural features include a distorted tetrahedral copper binding site at one end of an eight-stranded antiparallel beta-barrel, a pronounced negative patch, and a flat hydrophobic surface. The copper site is optimized for its electron transfer function, and the negative and hydrophobic patches are proposed to be involved in recognition of physiological reaction partners. Chemical modification, cross-linking, and site-directed mutagenesis experiments have confirmed the importance of the negative and hydrophobic patches in binding interactions with cytochrome f, and validated the model of two functionally significant electron transfer paths involving plastocyanin. One putative electron transfer path is relatively short (approximately 4 Å) and involves the solvent-exposed copper ligand His-87 in the hydrophobic patch, while the other is more lengthy (approximately 12-15 Å) and involves the nearly conserved residue Tyr-83 in the negative patch. Redinbo et al., J. Bioenerg. Biomembr. 26:49-66 (1994).

Rusticyanins

Rusticyanins are blue-copper containing single-chain polypeptides obtained from a *Thiobacillus* (now called *Acidithiobacillus*). The X-ray crystal structure of the oxidized form of the extremely stable and highly oxidizing cupredoxin rusticyanin from *Thiobacillus ferrooxidans* (SEQ ID NO: 4) has been determined by multiwavelength anomalous diffraction and refined to 1.9 Å resolution. The rusticyanins are composed of a core beta-sandwich fold composed of a six- and a seven-stranded b-sheet. Like other cupredoxins, the copper ion is coordinated by a cluster of four conserved residues (His 85, Cys138, His143, Met148) arranged in a distorted tetrahedron. Walter, R. L. et al., J. Mol. Biol. 263:730-51 (1996).

Pseudoazurins

The pseudoazurins are a family of blue-copper containing single-chain polypeptide. The amino acid sequence of pseudoazurin obtained from *Achromobacter cycloclastes* is shown in SEQ ID NO: 5. The X-ray structure analysis of pseudoazurin shows that it has a similar structure to the azurins although there is low sequence homology between these proteins. Two main differences exist between the overall structure of the pseudoazurins and azurins. There is a carboxy terminus extension in the pseudoazurins, relative to the azurins, consisting of two alpha-helices. In the mid-peptide region azurins contain an extended loop, shortened in the pseudoazurins, which forms a flap containing a short α-helix. The only major differences at the copper atom site are the conformation of the MET side-chain and the Met-S copper bond length, which is significantly shorter in pseudoazurin than in azurin.

Phytocyanins

The proteins identifiable as phytocyanins include, but are not limited to, cucumber basic protein, stellacyanin, mavicyanin, umecyanin, a cucumber peeling cupredoxin, a putative blue copper protein in pea pods, and a blue copper protein from *Arabidopsis thaliana*. In all except cucumber basic protein and the pea-pod protein, the axial methionine ligand normally found at blue copper sites is replaced by glutamine.

Auracyanin

Three small blue copper proteins designated auracyanin A, auracyanin B-1, and auracyanin B-2 have been isolated from the thermophilic green gliding photosynthetic bacterium *Chloroflexus aurantiacus*. The two B forms are glycoproteins and have almost identical properties to each other, but are distinct from the A form. The sodium dodecyl sulfate-polyacrylamide gel electrophoresis demonstrates apparent monomer molecular masses as 14 (A), 18 (B-2), and 22 (B-1) kDa.

The amino acid sequence of auracyanin A has been determined and showed auracyanin A to be a polypeptide of 139 residues. Van Dreissche et al., Protein Science 8:947-957 (1999). His58, Cys123, His128, and Met132 are spaced in a way to be expected if they are the evolutionary conserved metal ligands as in the known small copper proteins plastocyanin and azurin. Secondary structure prediction also indicates that auracyanin has a general beta-barrel structure similar to that of azurin from *Pseudomonas aeruginosa* and plastocyanin from poplar leaves. However, auracyanin appears to have sequence characteristics of both small copper protein sequence classes. The overall similarity with a consensus sequence of azurin is roughly the same as that with a consensus sequence of plastocyanin, namely 30.5%. The N-terminal sequence region 1-18 of auracyanin is remarkably rich in glycine and hydroxy amino acids. Id. See exemplary amino acid sequence SEQ ID NO: 15 for chain A of auracyanin from *Chloroflexus aurantiacus* (NCBI Protein Data Bank Accession No. AAM12874).

The auracyanin B molecule has a standard cupredoxin fold. The crystal structure of auracyanin B from *Chloroflexus aurantiacus* has been studied. Bond et al., J. Mol. Biol. 306:47-67 (2001). With the exception of an additional N-terminal strand, the molecule is very similar to that of the bacterial cupredoxin, azurin. As in other cupredoxins, one of the Cu ligands lies on strand 4 of the polypeptide, and the other three lie along a large loop between strands 7 and 8. The Cu site geometry is discussed with reference to the amino acid spacing between the latter three ligands. The crystallographically characterized Cu-binding domain of auracyanin B is probably tethered to the periplasmic side of the cytoplasmic membrane by an N-terminal tail that exhibits significant sequence identity with known tethers in several other membrane-associated electron-transfer proteins. The amino acid sequences of the B forms are presented in McManus et al. J. Biol. Chem. 267:6531-6540 (1992). See exemplary amino acid sequence SEQ ID NO: 16 for chain B of auracyanin from *Chloroflexus aurantiacus* (NCBI Protein Data Bank Accession No. 1QHQA).

Stellacyanin

Stellacyanins are a subclass of phytocyanins, a ubiquitous family of plant cupredoxins. An exemplary sequence of a stellacyanin is included herein as SEQ ID NO: 14. The crystal structure of umecyanin, a stellacyanin from horseradish root (Koch et al., J. Am. Chem. Soc. 127:158-166 (2005)) and cucumber stellacyanin (Hart et al., *Protein Science* 5:2175-2183 (1996)) is also known. The protein has an overall fold similar to the other phytocyanins. The ephrin B2 protein ectodomain tertiary structure bears a significant similarity to stellacyanin. Toth et al., Developmental Cell 1:83-92 (2001). An exemplary amino acid sequence of a stellacyanin is found in the National Center for Biotechnology Information Protein Data Bank as Accession No. 1JER, SEQ ID NO: 14.

Cucumber Basic Protein

An exemplary amino acid sequence from a cucumber basic protein is included herein as SEQ ID NO: 17. The crystal structure of the cucumber basic protein (CBP), a type 1 blue copper protein, has been refined at 1.8 Å resolution. The molecule resembles other blue copper proteins in having a Greek key beta-barrel structure, except that the barrel is open on one side and is better described as a "beta-sandwich" or "beta-taco". Guss et al., J. Mol. Biol. 262:686-705 (1996). The ephrinB2 protein ectodomian tertiary structure bears a high similarity (rms deviation 1.5 Å for the 50 α carbons) to the cucumber basic protein. Toth et al., Developmental Cell 1:83-92 (2001).

The Cu atom has the normal blue copper NNSS' co-ordination with bond lengths Cu—N(His39)=1.93 A, Cu—S(Cys79)=2.16 A, Cu—N(His84)=1.95 A, Cu—S(Met89)=2.61 A. A disulphide link, (Cys52)-S—S-(Cys85), appears to play an important role in stabilizing the molecular structure. The polypeptide fold is typical of a sub-family of blue copper proteins (phytocyanins) as well as a non-metalloprotein, ragweed allergen Ra3, with which CBP has a high degree of sequence identity. The proteins currently identifiable as phytocyanins are CBP, stellacyanin, mavicyanin, umecyanin, a cucumber peeling cupredoxin, a putative blue copper protein in pea pods, and a blue copper protein from *Arabidopsis thaliana*. In all except CBP and the pea-pod protein, the axial methionine ligand normally found at blue copper sites is replaced by glutamine. An exemplary sequence for cucumber basic protein is found in NCBI Protein Data Bank Accession No. 2CBP, SEQ ID NO: 17.

Methods of Use

The invention provides methods to prevent de novo malignancies in otherwise healthy patients comprising administering to the patient at least one peptide that is a cupredoxin, or variant, derivative or structural equivalent thereof, as described above. Chemopreventive therapies are based on the hypothesis that the interruption of processes involved in cancergenesis will prevent the development of cancer. The cupredoxin *Pseudomonas aeruginosa* azurin and the truncated azurin peptide p28 are now known to inhibit the development of premalignant lesions, either by inhibiting the initial formation of premalignant lesions, or killing or inhibiting the growth of premalignant lesions that are present. It therefore contemplated that a cupredoxin, or variant, derivative or structural equivalent thereof, as described above, with the ability to inhibit the development of premalignant lesions, may be used in chemopreventive therapies in otherwise healthy patients. Such otherwise healthy patients are, in some embodiments, patients at a higher risk to develop cancer than those in the general population. Cancers that may be prevented by treatment with the compositions of the invention include, but are not limited to, melanoma, breast, pancreas, glioblastoma, astrocytoma, lung, colorectal, neck and head, bladder, prostate, skin, and cervical cancer. In some embodiments, the patient may be human. In other embodiments, the patient is not human.

The invention further includes methods to study the development of cancer comprising contacting mammalian cells before or after induction with a carcinogen with a composition comprising cupredoxin, or a variant, derivative or structural equivalent thereof and observing the development of the cells. In some embodiments, the cells are mouse mammary gland cells, while in others they are other cells that may become malignant in mammals.

Patients at a higher at risk to develop cancer than the general population may be patients with high risk features, patients with premalignant lesions, and patients that have been cured of their initial cancer or definitively treated for their premalignant lesions. See generally Tsao et al., CA Cancer J Clin 54:150-180 (2004). High risk features may be behavioral, genetic, environmental or physiological factors of the patient. Behavioral factors that predispose a patient to various forms of cancer include, but are not limited to, smoking, diet, alcohol consumption, hormone replacement therapy, higher body mass index, nulliparity, betal nut use, frequent mouthwash use, exposure to human papillomavirus, childhood and chronic sun exposure, early age of first intercourse, multiple sexual partners, and oral contraceptive use. Genetic factors that predispose a patient to various forms of cancer include, but are not limited to, a family history of cancer, gene carrier status of BRCA1 and BRCA2, prior history of breast neoplasia, familial adenomatous polyposis (FAP), hereditary nonpolyposis colorectal cancer (HNPCC), red or blond hair and fair-skinned phenotype, xeroderma pigmentosum, and ethnicity. Environmental features that predispose a patient to various forms of cancer include, but are not limited to, exposure to radon, polycyclic aromatic hydrocarbons, nickel, chromate, arsenic, asbestos, chloromethyl ethers, benzo[a]pyrene, radiation, and aromatic amines from rubber or paint occupational exposure. Other miscellaneous factors that predispose a patient to various forms of cancer include, but are not limited to, chronic obstructive pulmonary disease with airflow obstruction, chronic bladder infections, schistosomiasis, older age, and immunocompromised status.

Additionally, patients at a higher risk of developing cancer may be determined by the use of various risk models that have been developed for certain kinds of cancer. For example, patients predisposed to breast cancer may be determined using the Gail risk model, orthe Claus model, among others. See Gail et al., J Natl Cancer Inst 81:1879-1886 (1989); Cuzick, Breast 12:405-411 (2003); Huang et al., Am J Epidemiol 151:703-714 (2000).

Patients with premalignant lesions are at a higher risk to develop cancer than the general population. The presence of premalignant lesions in or on a patient may be determined by many methods that are well known to those in the art. Intermediate markers or biomarkers that originate from premalignant lesions may be measured in a patient to determine if the patient harbors premalignant lesions. Chromosomal abnormalities occur in tumor cells and the adjacent histologicially normal tissues in the majority of cancer patients. Progression in chromosomal abnormalities parallels the phenotypic progression from premalignant lesion to invasive cancer. Thiberville et al., Cancer Res. 55:5133-5139 (1995). Therefore, chromosomal abnormalities associated with cancer may be used as intermediate markers to detect premalignant lesions in a patient. Common chromosomal abnormalities associated with cancer include, but are not limited to, allelic deletions or loss of heterozygosity (LOH) in tumor suppressor genes such as 3p (FHIT and others), 9p (9p21 for p16$^{INK4}$, p15$^{INK4B}$, and p19$^{ARF}$), 17p (17p13 for p53 gene and others) and 13q (13q14 for retinoblastoma gene Rb and others). Deletions in 3p and 9p are associated with smoking and the early stages of lung cancer. Mao et al., J. Natl. Cancer Inst. 89:857-862 (1997). Deletions affecting 3p, 5q, 8p, 17p and 18q are common change in epithelial cancers. See generally Tsao et al., CA Clin. Cancer J. Clin. 54:153 (2004). Other chromosomal mutations associated with cancer include those which activate oncogenes. Oncogenes whose presence may be used as intermediate markers include, but are not limited to, Ras, c-myc, epidemral growth factor, erb-B2 and cyclins E, D1 and B1. See generally id. at 154.

Other intermediate markers may be the products of genes up-regulated in premalignant cells and cancer cells. Genes that may be up-regulated in premalignant cells include, but are not limited to, cyclooxygenases COX-1 and COX-2, telomerase. Other biomarkers of cancer cells, and some premalignant cells, include, but are not limited to, p53, epidermal growth factor receptor (GFR), proliferating cell nuclear antigen (PCNA), RAS, COX-2, Ki-67, DNA aneuploidy, DNA polymerase-α, ER, Her2neu, E-cadherin, RARβ, hTERT, p16$^{INK4a}$, FHIT (3p14), Bcl-2, VEGF-R, HPV infection, LOH 9p21, LOH 17p, p-AKT, hnRNP A2/B1, RAF, Myc, c-KIT, cyclin D1, E and B1, IGF1, bcl-2, p16, LOH 3p21.3, LOH 3p25, LOH 9p21, LOH 17p13, LOH 13q, LOH 8p, hMSH2, APC, DCC, DPC4, JV18, BAX, PSA, GSTP1, NF-kB, AP1, D3S2, HPV infection, LOH 3p14, LOH 4q, LOH 5p, bladder tumor antigen (BTA), BTK TRAK (Alidex, Inc., Redmond Wash.), urinary tract matrix protein 22, fibrin degradation product, autodrine motility factor receptor, BCLA-4, cytokeratin 20, hyaluronic acid, CYFRA 21-1, BCA, beta-human chorionic gonadotropin, and tissue polypeptide antigen (TPA). See generally id. at 155-157.

Patients that have been cured of their initial cancers or have been definitively treated for their premalignant lesions are also at a higher risk to develop cancer than the general population. A second primary tumor refers to a new primary cancer in a person with a history of cancer. Second primary tumors are the leading cause of mortality in head and neck cancer. Id. at 150. A second primary tumor is distinct from a metastasis in that the former originates de novo while the later originates from an existing tumor. Patients that have been cured of cancer or premalignant lesions of the breast, head and neck, lung, and skin are at a particularly high risk to develop second primary tumors.

The compositions comprising a cupredoxin or variant, derivative or structural equivalent thereof can be administered to the patient by many routes and in many regimens that will be well known to those in the art. In specific embodiments, the cupredoxin, or variant, derivative or structural equivalent thereof is administered intravenously, intramuscularly, subcutaneously, topically, orally, or by inhalation. The compositions may be administered to the patient by any means that delivers the peptides to the site in the patient that is at risk of developing cancer. In specific embodiments, the cupredoxin or variant, derivative or structural equivalent thereof is administered intravenously.

In one embodiment, the methods may comprise co-administering to a patient one unit dose of a composition comprising a cupredoxin or a variant, derivative or structural equivalent of cupredoxin and one unit dose of a composition comprising another chemopreventive drug, in either order, administered at about the same time, or within about a given time following the administration of the other, for example, about one minute to about 60 minutes following the administration of the other drug, or about 1 hour to about 12 hours following the administration of the other drug. Chemopreventive drugs of interest include, but are not limited to, tamoxifen, aromatase inhibitors such as letrozole and anastrozole (Arimidex®), retinoids such as N-[4-hydroxyphenyl]retinamide (4-HPR, fenretinide), nonsteriodal antiinflammatory agents (NSAIDs) such as aspirin and sulindac, celecoxib (COX-2 inhibitor), defluoromethylornithing (DFMO), ursodeoxycholic acid, 3-hydroxy-3-methylglutaryl coenzyme A reductase inhibitors, EKI-785 (EGFR inhibitor), bevacizumab (antibody to VEGF-receptor), cetuximab (antibody to EGFR), retinol such as vitamin A, beta-carotene, 13-cis retinoic acid, isotretinoin and retinol palmitate, α-tocopherol, interferon, oncolytic adenovirus dl1520 (ONYX-015), gefitinib, etretinate, finasteride, indole-3-carbinol, resveratrol, chlorogenic acid, raloxifene, and oltipraz.

Compositions for Facilitating Selective Entry of Compounds into Cancer Cells and Tumors The present invention relates to methods and materials for delivering a cargo compound into a cell. Delivery of the cargo compound according to this invention is accomplished by the use of a suitable transport polypeptide. In one embodiment of the invention, the cargo compound is linked to the transport polypeptide. Suitable transport peptides include a cupredoxin, or a fragment of a cupredoxin containing a "cupredoxin entry domain". The term "cupredoxin entry domain" refers to a fragment of a cupredoxin that includes the amino sequence that is required for the entry of cupredoxin into a mammalian cancer cell. Cargo compounds delivered by the present invention include, but are not limited to, proteins, lipoproteins, polypeptides, peptides, polysaccharides, nucleic acids, including RNA, DNA and anti-sense nucleic acids, dyes, fluorescent and radioactive tags, microparticles or nanoparticles, toxins, inorganic and organic molecules, small molecules, and drugs (for example, chemopreventive drugs). In some embodiments, the drugs and toxins kill tumor cells.

In one embodiment of the invention, the cupredoxin is an azurin, such as azurin from *Pseudomonas aeruginosa* (SEQ ID NO: 1). In other embodiments of the invention, the cupredoxin is a plastocyanin, a rusticyanin, or a pseudoazurin, among others. In specific embodiments, the azurin is from *Pseudomonas aeruginosa, Pseudomonas syringa, Neisseria meningitides, Neisseria gonorrhoeae, Vibrio parahaemolyticus* or *Bordetella bronchiseptica*, among others.

In one embodiment, a cargo compound is delivered to kill or retard cell cycle progression in a cell, such as a cancer cell. Such a cancer cell can be, for example, an osteosarcoma cell, lung carcinoma cell, colon carcinoma cell, lymphoma cell, leukemia cell, soft tissue sarcoma cell or breast, liver, bladder or prostate carcinoma cell, among others. For example, the cargo compound can be a cell cycle control protein, such as p53; a cyclin-dependent kinase inhibitor, such as p16, p21 or p27; a suicide protein such as thymidine kinase or nitroreductase; a cytokine or other immunomodulatory protein such as interleukin 1, interleukin 2 or granulocyte-macrophage colony stimulating factor (GM-CSF); or a toxin, such as *Pseudomonas aeruginosa* exotoxin A, among others. In other embodiments, a biologically active fragment of one of the above classes of compounds is delivered. In another embodiment, the cargo compound is delivered in order to generate an image of the target tissue. For example, the target tissue can be a cancer and the cargo compound can be one commonly used to generate an image for detection by X-ray computed tomography (CT), Magnetic Resonance Imaging (MRI) and ultrasound. In these embodiments, the cargo compound is a gamma ray or positron emitting radioisotope, a magnetic resonance imaging contrast agent, an X-ray contrast agent, or an ultrasound contrast agent.

The invention further includes methods of selectively introducing DNA or RNA into a mammalian cancer cell. In such embodiments, the DNA or RNA is the cargo compound. In some embodiments, the method includes providing p18 coupled to DNA or RNA and introducing the compound into the body of a mammal. In some embodiments, the DNA or RNA is a gene or a fragment of a gene. In some embodiments, the DNA or RNA has a therapeutic effect once introduced into a mammalian cell.

Cupredoxin Entry Domain

The invention provides for a protein transduction domain that allows for the transport of linked cargo into mammalian cancer cells but not non-cancerous cells. It has been discovered that cupredoxin proteins comprise a protein transduction domain, the cupredoxin entry domain, which facilitates the entry of linked cargo into mammalian cancer cells. In some embodiments, the entire cupredoxin protein can be used to facilitate the transport linked cargo selectively into cancer cells. In other embodiments, a portion of a cupredoxin can be used to transport linked cargo into cancer cells. In some embodiments, the cupredoxin entry domain consists of a region of a cupredoxin that is less that the full length wild-type protein. In some embodiments, the cupredoxin entry domain consists more than about 10 residues, about 15 residues or about 20 residues of a cupredoxin. In some embodiments, the cupredoxin entry domain consists of not more than about 50 residues, about 40 residues or about 30 residues of a cupredoxin. In some embodiments, the cupredoxin entry domain has at least about 90% amino acid sequence identity, at least about 95% amino acid sequence identity or at least about 99% amino acid sequence identity to a cupredoxin.

In some embodiments, the cupredoxin entry domain is a azurin entry domain. In one embodiment of the present invention, azurin entry domain contains at least amino acids 50 to 77 of *Pseudomonas aeruginosa* azurin (SEQ ID NO: 2). In another embodiment of the invention, the cupredoxin entry domain contains at least amino acids 36 to 77 of *Pseudomonas aeruginosa* azurin (SEQ ID NO: 27). In another embodiment of the invention, the cupredoxin entry domain contains at least amino acids 36 to 89 of *Pseudomonas aeruginosa* azurin (SEQ ID NO: 28). In another embodiment of the invention, the cupredoxin entry domain contains at least amino acids 36 to 128 of *Pseudomonas aeruginosa* azurin (SEQ ID NO: 29). In yet another embodiment of the invention, the cupredoxin entry domain contains at least amino acids 50 to 67 of *Pseudomonas aeruginosa* azurin (SEQ ID NO: 25). In another embodiment of the invention, the cupredoxin entry domain contains at least amino acids 53 to 70 of *Pseudomonas aeruginosa* azurin (SEQ ID NO: 30). In yet another embodiment of the invention, the cupredoxin entry domain contains at least amino acids 53 to 64 of *Pseudomonas aeruginosa* azurin (SEQ ID NO: 31).

In another embodiment of the invention, the cupredoxin entry domain is an entry domain from a cupredoxin other than *P. aeruginosa* azurin. In different embodiments, the cupredoxin entry domain may be a fragment of plastocyanin from the cyanobacterium *Phormidium laminosum* (SEQ ID NO: 3), rusticyanin from *Thiobacillus ferrooxidans* (SEQ ID NO: 4); pseudoazurin from *Achromobacter cycloclastes* (SEQ ID NO: 5), azurin from *Pseudomonas syringae* (SEQ ID NO: 21), azurin from *Neisseria meningitidis* (SEQ ID NO: 10), azurin from *Vibrio parahaemolyticus* (SEQ ID NO: 8), or an auracyanin from *Chloroflexus aurantiacus* (SEQ ID NO: 15 and 16).

In another embodiment of the invention, the cupredoxin entry domain contains at least amino acids 57 to 89 of auracyanin B of *Chloroflexus aurantiacus* (SEQ ID NO: 20). In another embodiment of the invention, the cupredoxin entry domain contains at least amino acids 51-77 of *Pseudomonas syringae* azurin (SEQ ID NO: 21). In another embodiment of the invention, the cupredoxin entry domain contains at least amino acids 89-115 of *Neisseria meningitidis* Laz (SEQ ID NO: 22). In another embodiment of the invention, the cupredoxin entry domain contains at least amino acids 52-78 of *Vibrio parahaemolyticus* azurin (SEQ ID NO: 23). In another embodiment of the invention, the cupredoxin entry domain contains at least amino acids 51-77 of *Bordetella bronchiseptica* azurin (SEQ ID NO: 24).

Modification of a Cupredoxin Entry Domain

In another embodiment of the present invention, a cupredoxin entry domain is chemically modified or genetically altered to produce variants that retain the ability to transport a cargo compound into a cell. For example, Example 14 shows that *Pseudomonas aeruginosa* azurin having proline residues introduced at positions 54, 61 and 70 retains its ability to enter UISO-Mel-2 cells.

In another embodiment, the cupredoxin entry domain comprises a conserved amino acid sequence DGXXXXXDXXYXKXXD (SEQ ID NO: 32) or DGXXXXDXXYXKXXD (SEQ ID NO: 33) where D is aspartic acid, G is glycine, Y is tyrosine, K is lysine and X is any amino acid. See Example 17.

Variants of a cupredoxin entry domain may be synthesized by standard techniques. Derivatives are amino acid sequences formed from native compounds either directly or by modification or partial substitution. Analogs are amino acid sequences that have a structure similar, but not identical, to the native compound but differ from it in respect to certain components or side chains. Analogs may be synthesized or from a different evolutionary origin.

Variants may be full length or other than full length, if the derivative or analog contains a modified amino acid. Variants of a cupredoxin entry domain include, but are not limited to, molecules comprising regions that are substantially homologous to the cupredoxin entry domain by at least about 65%, 70%, 75%, 85%, 90%, 95%, 98%, or 99% identity over an amino acid sequence of identical size or when compared to an aligned sequence in which the alignment is performed by a homology algorithm.

In another embodiment, the variants of a cupredoxin entry domain have a significant structural similarity to *P. aeruginosa* azurin residues 50-77 (SEQ ID NO: 2). In other embodiments, the variants of a cupredoxin entry domain have a significant structural similarity to *P. aeruginosa* azurin residues 50-67 (SEQ ID NO: 25). Examples of studies that determine significant structural homology between cupredoxins and other proteins include Toth et al. (Developmental Cell 1:82-92 (2001)). Specifically, significant structural homology between a variant of the cupredoxin entry domain and *P. aeruginosa* azurin residues 50-77 (SEQ ID NO: 2) is determined by using the VAST algorithm (Gibrat et al., Curr Opin Struct Biol 6:377-385 (1996); Madej et al., Proteins 23:356-3690 (1995)). In specific embodiments, the VAST p value from a structural comparison of a variant of the cupredoxin entry domain and *P. aeruginosa* azurin residues 50-77 (SEQ ID NO: 2) is less than about $10^{-3}$, less than about $10^{-5}$, or less than about $10^{-7}$. In other embodiments, significant structural homology between a variant of the cupredoxin entry domain and *P. aeruginosa* azurin residues 50-77 (SEQ ID NO: 2) can be determined by using the DALI algorithm (Holm & Sander, J. Mol. Biol. 233:123-138 (1993)). In specific embodiments, the DALI Z score for a pairwise structural comparison is at least about 3.5, at least about 7.0, or at least about 10.0.

Modifications to the cupredoxin entry domain can be made using methods known in the art such as oligonucleotide-mediated (site-directed) mutagenesis, alanine scanning, and PCR mutagenesis. Site-directed mutagenesis (Carter, Biochem J. 237:1-7 (1986); Zoller and Smith, Methods Enzymol. 154:329-50 (1987)), cassette mutagenesis, restriction selection mutagenesis (Wells et al., Gene 34:315-23 (1985)) or other known techniques can be performed on the cloned DNA to produce a cupredoxin entry domain variant nucleic acid. In addition, nucleotides encoding entry domains with structural similarity to that of the cupredoxin entry domains may be synthesized by methods that are well known in the art. Further, protein molecules that are wild type or variant cupredoxin entry domains may be synthesized by methods that are well known in the art.

Nucleic Acids Coding for a the Cupredoxin Entry Domain and Complex of a Cupredoxin Entry Domain Linked to a Cargo Compound In another aspect, the present invention provides a nucleic acid molecule encoding a fusion protein comprising a cupredoxin entry domain linked to a cargo compound, where the cargo compound is a protein or peptide. The nucleic acid molecule according to the invention can be prepared by a combination of known techniques in the art. For instance, nucleic acid sequences for the cupredoxin entry domain and the cargo compound can individually be prepared by chemical synthesis or cloning. The nucleic acid sequences are then ligated in order with a ligase to give a nucleic acid molecule of interest.

Methods of Delivering a Cargo Compound Using a Cupredoxin Entry Domain

Many arginine-rich peptides are known to translocate through mammalian cell membranes and carry protein cargo compounds inside such cells. Suzuki, T., et al. J. Biol. Chem. 277:2437-43 (2002). For example, a short arginine-rich 11 amino acid (amino acids 47-57) segment of HIV Tat protein allows transport of cargo proteins into mammalian cells. Schwarze, S R., et al. Trends Cell Biol. 10:290-95 (2000). Synthetic entry domains that strengthen the alpha-helical content and optimize the placement of arginine residues have been shown to have enhanced potential as protein transduction domains. Ho, A., et al. Cancer Res. 61:474-77 (2001). In comparison, *P. aeruginosa* azurin has a single arginine residue. It is therefore believed, but not relied upon for the present invention, that its mode of entry is different from that of the Tat protein.

The present invention encompasses the use of those cupredoxin fragments that facilitate the entry of a cargo compound into a cell. Such fragments may be determined by any method that identifies those fragments required for entry into a cell. In one such method, a cupredoxin fragment is linked to a marker substance and a test performed to determine whether the cupredoxin fragment enters a cell. Such methods may be used to identify suitable fragments of the cupredoxins discussed above.

In various embodiments of the present invention, the cargo compound is attached to a cupredoxin or a fragment thereof, such as azurin from *P. aeruginosa* (SEQ ID NO: 1); plastocyanin from the cyanobacterium *Phormidium laminosum* (SEQ ID NO: 3); rusticyanin from *Thiobacillus ferrooxidans* (SEQ ID NO: 4); or pseudoazurin from *Achromobacter cycloclastes* (SEQ ID NO: 5), a fragment of an azurin from *Pseudomonas syringae* (SEQ ID NO: 21), azurin from *Neisseria meningitidis* (SEQ ID NO: 10), azurin from *Vibrio parahaemolyticus* (SEQ ID NO: 19), azurin from *Bordetella bronchiseptica* (SEQ ID NO: 8), auracyanin A and B from *Chloroflexus aurantiacus* (SEQ ID NO. 15 and 16), among other azurin and azurin-like proteins. In other embodiments, the cargo is linked to a cupredoxin entry domain such as p28 (SEQ ID NO: 2) or p18 (SEQ ID NO: 25).

In various embodiments of the present invention, a cupredoxin entry domain delivers a cargo compound into a cell in vitro, ex vivo or in vivo. For example, delivery may be achieved in vitro by adding a complex of a cupredoxin entry domain and a cargo compound to a cell culture, such as a pap smear. Alternatively, delivery may be achieved ex vivo by adding the complex to a sample removed from a patient, for example, blood, tissue, or bone marrow, and returning the treated sample to the patient. Delivery may also be achieved by administration of the complex directly to a patient. The methods of the present invention may be used for therapeutic, prophylactic, diagnostic or research purposes. Cargo compounds delivered by the present invention include, but are not limited to, proteins, lipoproteins, polypeptides, peptides, polysaccharides, nucleic acids, including anti-sense nucleic acids, dyes, microparticles or nanoparticles, toxins, organic and inorganic molecules, small molecules, and drugs.

In one embodiment, a detectable substance, for example, a fluorescent substance, such as green fluorescent protein; a luminescent substance; an enzyme, such as β-galactosidase; or a radiolabelled or biotinylated protein is delivered to confer a detectable phenotype to a cell. Similarly, microparticles or nanoparticles labeled with a detectable substance, for example, a fluorescent substance, can be delivered. One example of suitable nanoparticles is found in U.S. Pat. No. 6,383,500, issued May 7, 2002, which is hereby expressly incorporated by reference. Many such detectable substances are known to those skilled in the art.

In some embodiments, the cargo compound is a detectable substance that is suitable for X-ray computed tomography, magnetic resonance imaging, ultrasound imaging or radionuclide scintigraphy. In these embodiments, the cargo compound is administered to the patient for purposes of diagnosis. A contrast agent is administered as a cargo compound to enhance the image obtained by X-ray CT, MRI and ultrasound. The administration of a radionuclide cargo compound that is targeted to tumor tissue via the cupredoxin entry domain can be used for radionuclide scinitigraphy. In some embodiments, the cupredoxin entry domain may contain the radionucleotide with or without a cargo compound. In other embodiments, the cargo compound is a gamma ray or positron emitting radioisotope, a magnetic resonance imaging contract agent, an X-ray contrast agent, or an ultrasound contrast agent.

Ultrasound contrast agents suitable for use as cargo compounds include, but are not limited to, a microbubble of a biocompatible gas, a liquid carrier, and a surfactant microsphere, further comprising an optional linking moiety, $L_n$, between the targeting moieties and the microbubble. In this context, the term liquid carrier means aqueous solution and the term surfactant means any amphiphilic material which produces a reduction in interfacial tension in a solution. A list of suitable surfactants for forming surfactant microspheres is disclosed in EP0727225A2, herein expressly incorporated by reference. The term surfactant microsphere includes nanospheres, liposomes, vesicles and the like. The biocompatible gas can be air, or a fluorocarbon, such as a $C_3$-$C_5$ perfluoroalkane, which provides the difference in echogenicity and thus the contrast in ultrasound imaging. The gas is encapsulated or contained in the microsphere to which is attached the cupredoxin entry domain, optionally via a linking group. The attachment can be covalent, ionic or by van der Waals forces. Specific examples of such contrast agents include lipid encapsulated perfluorocarbons with a plurality of tumor neovasculature receptor binding peptides, polypeptides or peptidomimetics.

X-ray contrast agents suitable for use as cargo compounds include, but are not limited to, one or more X-ray absorbing or "heavy" atoms of atomic number 20 or greater, further comprising an optional linking moiety, $L_n$, between the cupredoxin entry domain and the X-ray absorbing atoms. The frequently used heavy atom in X-ray contrast agents is iodine. Recently, X-ray contrast agents comprised of metal chelates (e.g., U.S. Pat. No. 5,417,959) and polychelates comprised of a plurality of metal ions (e.g., U.S. Pat. No. 5,679,810) have been disclosed. More recently, multinuclear cluster complexes have been disclosed as X-ray contrast agents (e.g., U.S. Pat. No. 5,804,161, PCT WO91/14460, and PCT WO 92/17215).

MRI contrast agents suitable for use as cargo compounds include, but are not limited to, one or more paramagnetic metal ions, further comprising an optional linking moiety, $L_n$, between the cupredoxin entry domain and the paramagnetic metal ions. The paramagnetic metal ions are present in the form of metal complexes or metal oxide particles. U.S. Pat. Nos. 5,412,148, and 5,760,191, describe examples of chelators for paramagnetic metal ions for use in MRI contrast agents. U.S. Pat. No. 5,801,228, U.S. Pat. No. 5,567,411, and U.S. Pat. No. 5,281,704, describe examples of polychelants useful for complexing more than one paramagnetic metal ion for use in MRI contrast agents. U.S. Pat. No. 5,520,904, describes particulate compositions comprised of paramagnetic metal ions for use as MRI contrast agents.

In another embodiment, a cargo compound is delivered to kill or retard cell cycle progression in a cell, such as a cancer cell. Such a cancer cell can be, for example, an osteosarcoma cell, lung carcinoma cell, colon carcinoma cell, lymphoma cell, leukemia cell, soft tissue sarcoma cell or breast, liver, bladder or prostate carcinoma cell. For example, the cargo compound can be a cell cycle control protein, such as p53; a cyclin-dependent kinase inhibitor, such as p16, p21 or p27; a suicide protein such as thymidine kinase or nitroreductase; a cytokine or other immunomodulatory protein such as interleukin 1, interleukin 2 or granulocyte-macrophage colony stimulating factor (GM-CSF); or a toxin, such as *Pseudomonas aeruginosa* exotoxin A. In other embodiments, a biologically active fragment of one of the above classes of compounds is delivered.

In yet another embodiment, the cargo compound is a nucleic acid. In some embodiments the nucleic acid codes for one of the above classes of compounds. In yet another embodiment, the cargo compound is a drug used to treat cancer. Such drugs include, for example, 5-fluorouracil; Interferon α; Methotrexate; Tamoxifen; and Vincrinstine. The above examples are provided for illustration only, many other such compounds are known to those skilled in the art. In other embodiments, the nucleic acid is useful for gene therapy.

Cargo compounds suitable for treating cancer include, but not limited to, alkylating agents such as nitrogen mustards, alkyl sulfonates, nitrosoureas, ethylenimines, and triazenes; antimetabolites such as folate antagonists, purine analogues, and pyrimidine analogues; antibiotics such as anthracyclines, bleomycins, mitomycin, dactinomycin, and plicamycin; enzymes such as L-asparaginase; farnesyl-protein transferase inhibitors; 5.alpha.-reductase inhibitors; inhibitors of 17.beta.-hydroxysteroid dehydrogenase type 3; hormonal agents such as glucocorticoids, estrogens/antiestrogens, androgens/antiandrogens, progestins, and luteinizing hormone-releasing hormone antagonists, octreotide acetate; microtubule-disruptor agents, such as ecteinascidins or their analogs and derivatives; microtubule-stabilizing agents such as taxanes, for example, paclitaxel (Taxol™), docetaxel (Taxotere™), and their analogs, and epothilones, such as epothilones A-F and their analogs; plant-derived products, such as vinca alkaloids, epipodophyllotoxins, taxanes; and topiosomerase inhibitors; prenyl-protein transferase inhibitors; and miscellaneous agents such as hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators and monoclonal antibodies.

Representative examples of these classes of anti-cancer and cytotoxic agents include but are not limited to mechlorethamine hydrochloride, cyclophosphamide, chlorambucil, melphalan, ifosfamide, busulfan, carmustin, lomustine, semustine, streptozocin, thiotepa, dacarbazine, methotrexate, thioguanine, mercaptopurine, fludarabine, pentastatin, cladribin, cytarabine, fluorouracil, doxorubicin hydrochloride, daunorubicin, idarubicin, bleomycin sulfate, mitomycin C, actinomycin D, safracins, saframycins, quinocarcins, discodermolides, vincristine, vinblastine, vinorelbine tartrate, etoposide, etoposide phosphate, teniposide, paclitaxel, tamoxifen, estramustine, estramustine phosphate sodium, flutamide, buserelin, leuprolide, pteridines, diyneses, levamisole, aflacon, interferon, interleukins, aldesleukin, filgrastim, sargramostim, rituximab, BCG, tretinoin, irinotecan hydrochloride, betamethosone, gemcitabine hydrochloride, altretamine, and topoteca and any analogs or derivatives thereof.

Preferred members of these classes include, but are not limited to, paclitaxel, cisplatin, carboplatin, doxorubicin, caminomycin, daunorubicin, aminopterin, methotrexate, methopterin, mitomycin C, ecteinascidin 743, or pofiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine and leurosine.

Examples of anticancer and other cytotoxic agents useful as cargo compounds include the following: epothilone derivatives as found in German Patent No. 4138042.8; WO 97/19086, WO 98/22461, WO 98/25929, WO 98/38192, WO 99/01124, WO 99/02224, WO 99/02514, WO 99/03848, WO 99/07692, WO 99/27890, WO 99/28324, WO 99/43653, WO 99/54330, WO 99/54318, WO 99/54319, WO 99/65913, WO 99/67252, WO 99/67253 and WO 00/00485; cyclin dependent kinase inhibitors as found in WO 99/24416 (see also U.S. Pat. No. 6,040,321); and prenyl-protein transferase inhibitors as found in WO 97/30992 and WO 98/54966; and agents such as those described generically and specifically in U.S. Pat. No. 6,011,029 (the compounds of which U.S. patent can be employed together with any NHR modulators (including, but not limited to, those of present invention) such as AR modulators, ER modulators, with LHRH modulators, or with surgical castration, especially in the treatment of cancer).

The above other therapeutic agents, when employed as cargo compounds with the compounds of the present invention, may be used, for example, in those amounts indicated in the Physicians' Desk Reference (PDR) or as otherwise determined by one of ordinary skill in the art.

Pharmaceutical Compositions Containing a Cupredoxin Entry Domain

Pharmaceutical compositions containing a complex of a cupredoxin entry domain linked to a cargo compound can be manufactured in any conventional manner, e.g., by conventional mixing, dissolving, granulating, dragee-making, emulsifying, encapsulating, entrapping, or lyophilizing processes. The complex can be readily combined with a pharmaceutically acceptable carrier well-known in the art. Such carriers enable the preparation to be formulated as a tablet, pill, dragee, capsule, liquid, gel, syrup, slurry, suspension, and the like. Suitable excipients can also include, for example, fillers and cellulose preparations. Other excipients can include, for example, flavoring agents, coloring agents, detackifiers, thickeners, and other acceptable additives, adjuvants, or binders.

Such compositions can be used in, for example, the detection or imaging of a cell type or in the treatment of a condition related to cell death or in the prevention thereof. The compositions can be administered in an amount sufficient to prevent or treat a condition related to resistance to cell death. As used herein, the term "a condition related to resistance to cell death" refers to a disease, state, or ailment characterized by at least a tendency for prolonged cell life when compared with a healthy cell of like kind as determined by a reasonable, skilled physician or clinician. Typically, the host organism is a mammal, such as a human or animal.

Administration of Compositions Containing a Cupredoxin Entry Domain

Compositions containing a cupredoxin entry domain can be administered by any suitable route, for example, by oral, buccal, inhalation, sublingual, rectal, vaginal, transurethral, nasal, topical, percutaneous, i.e., transdermal or parenteral (including intravenous, intramuscular, subcutaneous and intracoronary administration). The compositions and pharmaceutical formulations thereof can be administered in any amount effective to achieve its intended purpose. When administered to treat a condition related to resistance to cell death, the composition is administered in a therapeutically effective amount. A "therapeutically effective amount" is an amount effective to prevent development of, or to alleviate the existing symptoms of, the subject being treated. Determination of a therapeutically effective amount is well within the capability of those skilled in the art.

The appropriate dosage will, of course, vary depending upon, for example, the compound containing the cupredoxin entry domain employed, the host, the mode of administration and the nature and severity of the conditions being treated or diagnosed. However, in one embodiment of the methods of the present invention, satisfactory treatment results in humans are indicated to be obtained at daily dosages from about 0.001 to about 20 mg/kg of body weight of the compound containing the cupredoxin entry domain. In one embodiment, an indicated daily dosage for treatment in humans may be in the range from about 0.7 mg to about 1400 mg of a compound containing the cupredoxin entry domain conveniently administered, for example, in daily doses, weekly doses, monthly doses, and/or continuous dosing. Daily doses can be in discrete dosages from 1 to 12 times per day. Alternatively, doses can be administered every other day, every third day, every fourth day, every fifth day, every sixth day, every week, and similarly in day increments up to 31 days. Dosing can be continuous, intermittent or a single dose, using any applicable dosing form, including tablet, patches, i.v. administration and the like. More specifically, the composition is administered in a therapeutically effective amount. In specific embodiments, the therapeutically effective amount is from about 0.01-20 mg/kg of body weight. In specific embodiments, the dose level is about 10 mg/kg/day, about 15 mg/kg/day, about 20 mg/kg/day, about 25 mg/kg/day, about 30 mg/kg/day, about 35 mg/kg/day, about 40 mg/kg/day, about 45 mg/kg/day or about 50 mg/kg/day.

The method of introducing compounds containing the cupredoxin entry domain to patients is, in some embodiments, co-administration with other drugs known to treat cancer. Such methods are well-known in the art. In a specific embodiment, the compounds containing the cupredoxin entry domain are part of an cocktail or co-dosing containing or with other drugs for treating cancer. Such drugs include, for example, those listed herein and specifically 5-fluorouracil; Interferon α; Methotrexate; Tamoxifen; and Vincrinstine. The above examples are provided for illustration only, many other such compounds are known to those skilled in the art.

Nucleic acid molecules encoding a cupredoxin entry domain or a fusion protein combining a either entry domain and a cargo compound can be inserted into vectors and used as gene therapy vectors. Gene therapy vectors can be delivered to a subject by, for example, intravenous injection, local administration (Nabel et al., U.S. Pat. No. 5,328,470 1994. USA), or by stereotactic injection (Chen et al., Proc Natl Acad Sci USA, vol. 91, pp 3054-57 (1994)). The pharmaceutical preparation of a gene therapy vector can include an acceptable diluent or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

In one aspect, the composition is delivered as DNA such that the complex is generated in situ. In one embodiment, the DNA is "naked," as described, for example, in Ulmer et al., *Science* 259:1745-49 (1993) and reviewed by Cohen, *Science* 259 1691-92 (1993). The uptake of naked DNA may be increased by coating the DNA onto a carrier, e.g. a biodegradable bead, which is efficiently transported into the cells. In such methods, the DNA may be present within any of a variety of delivery systems known to those of ordinary skill in the art, including nucleic acid expression systems, bacterial and viral expression systems. Techniques for incorporating DNA into such expression systems are well known to those of ordinary skill in the art. See, e.g., WO90/11092, WO93/24640, WO 93/17706, and U.S. Pat. No. 5,736,524.

Vectors, used to shuttle genetic material from organism to organism, can be divided into two general classes: Cloning vectors are replicating plasmid or phage with regions that are non-essential for propagation in an appropriate host cell and into which foreign DNA can be inserted; the foreign DNA is replicated and propagated as if it were a component of the vector. An expression vector (such as a plasmid, yeast, or animal virus genome) is used to introduce foreign genetic material into a host cell or tissue in order to transcribe and translate the foreign DNA, such as the DNA of the composition. In expression vectors, the introduced DNA is operably-linked to elements such as promoters that signal to the host cell to transcribe the inserted DNA. Some promoters are exceptionally useful, such as inducible promoters that control gene transcription in response to specific factors. Operably-linking a composition polynucleotide to an inducible promoter can control the expression of the wt-azurin entry domain composition polypeptide or fragments. Examples of classic inducible promoters include those that are responsive to α-interferon, heat shock, heavy metal ions, and steroids such as glucocorticoids (Kaufman, *Methods Enzymol.* 185: 487-511 (1990)) and tetracycline. Other desirable inducible promoters include those that are not endogenous to the cells in which the construct is being introduced, but, however, are responsive in those cells when the induction agent is exogenously supplied. In general, useful expression vectors are often plasmids. However, other forms of expression vectors, such as viral vectors (e.g., replication defective retroviruses, adenoviruses and adeno-associated viruses) are contemplated.

Vector choice is dictated by the organism or cells being used and the desired fate of the vector. In general, vectors comprise signal sequences, origins of replication, marker genes, enhancer elements, promoters, and transcription termination sequences.

Kits Comprising a Cupredoxin Entry Domain-Cargo Compound Complex

In another aspect, the invention provides kits containing one or more of the following in a package or container: (1) a reagent comprising a complex of a cupredoxin entry domain linked to a cargo compound; (2) a reagent containing a pharmaceutically acceptable adjuvant or excipient; (3) a vehicle for administration, such as a syringe; (4) instructions for administration. Embodiments in which two or more of components (1)-(4) are found in the same container are also contemplated.

Pharmaceutical Compositions Comprising Cupredoxin a Cupredoxin Entry Domain, a Cupredoxin Entry Domain—Cargo Compound Complex, or Variant, Derivative or Structural Equivalent Thereof Pharmaceutical compositions comprising cupredoxin or variant, derivative or structural equivalents thereof, can be manufactured in any conventional manner, e.g., by conventional mixing, dissolving, granulating, dragee-making, emulsifying, encapsulating, entrapping, or lyophilizing processes. The substantially pure or pharmaceutical grade cupredoxin or variants, derivatives and structural equivalents thereof can be readily combined with a pharmaceutically acceptable carrier well-known in the art. Such carriers enable the preparation to be formulated as a tablet, pill, dragee, capsule, liquid, gel, syrup, slurry, suspension, and the like. Suitable carriers or excipients can also include, for example, fillers and cellulose preparations. Other excipients can include, for example, flavoring agents, coloring agents, detackifiers, thickeners, and other acceptable additives, adjuvants, or binders. In some embodiments, the pharmaceutical preparation is substantially free of preservatives. In other embodiments, the pharmaceutical preparation may contain at least one preservative. General methodology on pharmaceutical dosage forms is found in Ansel et al., *Pharmaceutical Dosage Forms and Drug Delivery Systems* (Lippencott Williams & Wilkins, Baltimore Md. (1999)).

The composition comprising a cupredoxin or variant, derivative or structural equivalent thereof used in the invention may be administered in a variety of ways, including by injection (e.g., intradermal, subcutaneous, intramuscular, intraperitoneal and the like), by inhalation, by topical administration, by suppository, by using a transdermal patch or by mouth. General information on drug delivery systems can be found in Ansel et al., id. In some embodiments, the composition comprising a cupredoxin or variant, derivative or structural equivalent thereof can be formulated and used directly as injectibles, for subcutaneous and intravenous injection, among others. The injectable formulation, in particular, can advantageously be used to treat patients that are appropriate for chemopreventive therapy. The composition comprising a cupredoxin or variant, derivative or structural equivalent thereof can also be taken orally after mixing with protective agents such as polypropylene glycols or similar coating agents.

When administration is by injection, the cupredoxin or variant, derivative or structural equivalent thereof may be formulated in aqueous solutions, specifically in physiologically compatible buffers such as Hanks solution, Ringer's solution, or physiological saline buffer. The solution may contain formulatory agents such as suspending, stabilizing and/or dispersing agents. Alternatively, the cupredoxin or variant, derivative or structural equivalent thereof may be in powder form for constitution with a suitable vehicle, e.g., sterile pyrogen-free water, before use. In some embodiments, the pharmaceutical composition does not comprise an adjuvant or any other substance added to enhance the immune response stimulated by the peptide. In some embodiments, the pharmaceutical composition comprises a substance that inhibits an immune response to the peptide.

When administration is by intravenous fluids, the intravenous fluids for use administering the cupredoxin or variant, derivative or structural equivalent thereof may be composed of crystalloids or colloids. Crystalloids as used herein are aqueous solutions of mineral salts or other water-soluble molecules. Colloids as used herein contain larger insoluble molecules, such as gelatin. Intravenous fluids may be sterile.

Crystalloid fluids that may be used for intravenous administration include but are not limited to, normal saline (a solution of sodium chloride at 0.9% concentration), Ringer's lactate or Ringer's solution, and a solution of 5% dextrose in water sometimes called D5W, as described in Table 2.

TABLE 2

Composition of Common Crystalloid Solutions

| Solution | Other Name | [Na+] | [Cl−] | [Glucose] |
|---|---|---|---|---|
| D5W | 5% Dextrose | 0 | 0 | 252 |
| 2/3 & 1/3 | 3.3% Dextrose/ 0.3% saline | 51 | 51 | 168 |
| Half-normal saline | 0.45% NaCl | 77 | 77 | 0 |
| Normal saline | 0.9% NaCl | 154 | 154 | 0 |
| Ringer's lactate* | Ringer's solution | 130 | 109 | 0 |

*Ringer's lactate also has 28 mmol/L lactate, 4 mmol/L K+ and 3 mmol/L $Ca^{2+}$.

When administration is by inhalation, the cupredoxin or variant, derivative or structural equivalent thereof may be delivered in the form of an aerosol spray from pressurized packs or a nebulizer with the use of a suitable propellant, e.g., dichlorodifluoromethane, trichlorofluoromethane, carbon dioxide or other suitable gas. In the case of a pressurized aerosol, the dosage unit may be determined by providing a valve to deliver a metered amount. Capsules and cartridges of, e.g., gelatin, for use in an inhaler or insufflator may be formulated containing a powder mix of the proteins and a suitable powder base such as lactose or starch.

When administration is by topical administration, the cupredoxin or variant, derivative or structural equivalent thereof may be formulated as solutions, gels, ointments, creams, jellies, suspensions, and the like, as are well known in the art. In some embodiments, administration is by means of a transdermal patch. When administration is by suppository (e.g., rectal or vaginal), cupredoxin or variants and derivatives thereof compositions may also be formulated in compositions containing conventional suppository bases.

When administration is oral, a cupredoxin or variant, derivative or structural equivalent thereof can be readily formulated by combining the cupredoxin or variant, derivative or structural equivalent thereof with pharmaceutically acceptable carriers well known in the art. A solid carrier, such as mannitol, lactose, magnesium stearate, and the like may be employed; such carriers enable the cupredoxin and variants, derivatives or structural equivalent thereof to be formulated as tablets, pills, dragees, capsules, liquids, gels, syrups, slurries, suspensions and the like, for oral ingestion by a subject to be treated. For oral solid formulations such as, for example, powders, capsules and tablets, suitable excipients include fillers such as sugars, cellulose preparation, granulating agents, and binding agents.

Other convenient carriers, as well-known in the art, also include multivalent carriers, such as bacterial capsular polysaccharide, a dextran or a genetically engineered vector. In addition, sustained-release formulations that include a cupredoxin or variant, derivative or structural equivalent thereof allow for the release of cupredoxin or variant, derivative or structural equivalent thereof over extended periods of time, such that without the sustained release formulation, the cupredoxin or variant, derivative or structural equivalent thereof would be cleared from a subject's system, and/or degraded by, for example, proteases and simple hydrolysis before eliciting or enhancing a therapeutic effect.

The half-life in the bloodstream of the peptides of the invention can be extended or optimized by several methods well known to those in the art. The peptide variants of the invention may include, but are not limited to, various variants that may increase their stability, specific activity, longevity in the bloodstream, and/or decrease immunogenicity of the cupredoxin, while retaining the ability of the peptide to inhibit the development of premalignant lesions in mammalian cells, tissues and animals. Such variants include, but are not limited to, those which decrease the hydrolysis of the peptide, decrease the deamidation of the peptide, decrease the oxidation, decrease the immunogenicity, increase the structural stability of the peptide or increase the size of the peptide. Such peptides also include circularized peptides (see Monk et al., BioDrugs 19(4):261-78, (2005); DeFreest et al., J. Pept. Res. 63(5):409-19 (2004)), D,L-peptides (diastereomer), Futaki et al., J. Biol. Chem. February 23; 276(8):5836-40 (2001); Papo et al., Cancer Res. 64(16):5779-86 (2004); Miller et al., Biochem. Pharmacol. 36(1):169-76, (1987)); peptides containing unusual amino acids (see Lee et al., J. Pept. Res. 63(2):69-84 (2004)), N- and C-terminal modifications (see Labrie et al., Clin. Invest. Med. 13(5):275-8, (1990)), hydrocarbon stapling (see Schafineister et al., J. Am. Chem. Soc. 122:5891-5892 (2000); Walenski et al., Science 305:1466-1470 (2004)) and PEGylation.

In various embodiments, the pharmaceutical composition includes carriers and excipients (including but not limited to buffers, carbohydrates, mannitol, proteins, polypeptides or amino acids such as glycine, antioxidants, bacteriostats, chelating agents, suspending agents, thickening agents and/or preservatives), water, oils, saline solutions, aqueous dextrose and glycerol solutions, other pharmaceutically acceptable auxiliary substances as required to approximate physiological conditions, such as buffering agents, tonicity adjusting agents, wetting agents and the like. It will be recognized that, while any suitable carrier known to those of ordinary skill in the art may be employed to administer the compositions of this invention, the type of carrier will vary depending on the mode of administration. Compounds may also be encapsulated within liposomes using well-known technology. Biodegradable microspheres may also be employed as carriers for the pharmaceutical compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344 and 5,942,252.

The pharmaceutical compositions may be sterilized by conventional, well-known sterilization techniques, or may be sterile filtered. The resulting aqueous solutions may be packaged for use as is, or lyophilized, the lyophilized preparation being combined with a sterile solution prior to administration.

Administration of Cupredoxin or Variant, Derivative or Structural Equivalent Thereof The cupredoxin or variant, derivative or structural equivalent thereof can be administered formulated as pharmaceutical compositions and administered by any suitable route, for example, by oral, buccal, inhalation, sublingual, rectal, vaginal, transurethral, nasal, topical, percutaneous, i.e., transdermal or parenteral (including intravenous, intramuscular, subcutaneous and intracoronary) or vitreous administration. The pharmaceutical formulations thereof can be administered in any amount effective to achieve its intended purpose. More specifically, the composition is administered in a therapeutically effective amount. In specific embodiments, the therapeutically effective amount is generally from about 0.01-20 mg/day/kg of body weight.

The compounds comprising cupredoxin or variant, derivative or structural equivalent thereof are useful for the prevention of cancer, alone or in combination with other active agents and/or cargo compounds. The appropriate dosage will, of course, vary depending upon, for example, the compound of cupredoxin or variant, derivative or structural equivalent thereof employed, the host, the mode of administration and the nature and severity of the potential cancer. However, in general, satisfactory results in humans are indicated to be obtained at daily dosages from about 0.01-20 mg/kg of body weight. An indicated daily dosage in humans is in the range from about 0.7 mg to about 1400 mg of a compound of cupredoxin or variant, derivative or structural equivalent thereof conveniently administered, for example, in daily doses, weekly doses, monthly doses, and/or continuous dosing. Daily doses can be in discrete dosages from 1 to 12 times per day. Alternatively, doses can be administered every other day, every third day, every fourth day, every fifth day, every sixth day, every week, and similarly in day increments up to 31 days or over. Alternatively, dosing can be continuous using patches, i.v. administration and the like.

The exact formulation, route of administration, and dosage is determined by the attending physician in view of the patient's condition. Dosage amount and interval can be adjusted individually to provide plasma levels of the active cupredoxin or variant, derivative or structural equivalent thereof, with or without a cargo compound, which are sufficient to maintain therapeutic effect. Generally, the desired cupredoxin or variant, derivative or structural equivalent thereof is administered in an admixture with a pharmaceutical carrier selected with regard to the intended route of administration and standard pharmaceutical practice.

In one aspect, the cupredoxin or variant, derivative or structural equivalent thereof is delivered as DNA such that the polypeptide is generated in situ. In one embodiment, the DNA is "naked," as described, for example, in Ulmer et al., (Science 259:1745-1749 (1993)) and reviewed by Cohen (Science 259:1691-1692 (1993)). The uptake of naked DNA may be increased by coating the DNA onto a carrier, e.g., biodegradable beads, which are then efficiently transported into the cells. In such methods, the DNA may be present within any of a variety of delivery systems known to those of ordinary skill in the art, including nucleic acid expression systems, bacterial and viral expression systems. Techniques for incorporating DNA into such expression systems are well known to those of ordinary skill in the art. See, e.g., WO90/11092, WO93/24640, WO 93/17706, and U.S. Pat. No. 5,736,524.

Vectors, used to shuttle genetic material from organism to organism, can be divided into two general classes: Cloning vectors are replicating plasmid or phage with regions that are essential for propagation in an appropriate host cell and into which foreign DNA can be inserted; the foreign DNA is replicated and propagated as if it were a component of the vector. An expression vector (such as a plasmid, yeast, or animal virus genome) is used to introduce foreign genetic material into a host cell or tissue in order to transcribe and translate the foreign DNA, such as the DNA of a cupredoxin. In expression vectors, the introduced DNA is operably-linked to elements such as promoters that signal to the host cell to highly transcribe the inserted DNA. Some promoters are exceptionally useful, such as inducible promoters that control gene transcription in response to specific factors. Operably-linking a cupredoxin and variants and derivatives thereof polynucleotide to an inducible promoter can control the expression of the cupredoxin and variants and derivatives thereof in response to specific factors. Examples of classic inducible promoters include those that are responsive to $\alpha$-interferon, heat shock, heavy metal ions, and steroids such as glucocorticoids (Kaufman, Methods Enzymol. 185: 487-511 (1990)) and tetracycline. Other desirable inducible promoters include those that are not endogenous to the cells in which the construct is being introduced, but, are responsive in those cells when the induction agent is exogenously supplied. In general, useful expression vectors are often plasmids. However, other forms of expression vectors, such as viral vectors (e.g., replication defective retroviruses, adenoviruses and adeno-associated viruses) are contemplated. In addition, the peptides of the present invention, including in one embodiment, p18, may be used as a vector to selectively deliver therapeutic compounds into cancer cells or tumors.

Vector choice is dictated by the organism or cells being used and the desired fate of the vector. In general, vectors comprise signal sequences, origins of replication, marker genes, polylinker sites, enhancer elements, promoters, and transcription termination sequences.

Kits Comprising Cupredoxin, or Variant, Derivative or Structural Equivalent Thereof In one aspect, the invention provides regimens or kits comprising one or more of the following in a package or container: (1) a pharmacologically active composition comprising at least one cupredoxin or variant, derivative or structural equivalent thereof; (2) an additional chemopreventive drug, (3) apparatus to administer the biologically active composition to the patient, such as a syringe, nebulizer etc.

When a kit is supplied, the different components of the composition may be packaged in separate containers, if appropriate, and admixed immediately before use. Such packaging of the components separately may permit long-term storage without losing the active components' functions.

The reagents included in the kits can be supplied in containers of any sort such that the life of the different components are preserved and are not adsorbed or altered by the materials of the container. For example, sealed glass ampules may contain lyophilized cupredoxin and variants, derivatives and structural equivalents thereof, or buffers that have been packaged under a neutral, non-reacting gas, such as nitrogen. Ampules may consist of any suitable material, such as glass, organic polymers, such as polycarbonate, polystyrene, etc., ceramic, metal or any other material typically employed to hold similar reagents. Other examples of suitable containers include simple bottles that may be fabricated from similar substances as ampules, and envelopes, that may comprise foil-lined interiors, such as aluminum or an alloy. Other containers include test tubes, vials, flasks, bottles, syringes, or the like. Containers may have a sterile access port, such as a bottle having a stopper that can be pierced by a hypodermic injection needle. Other containers may have two compartments that are separated by a readily removable membrane that upon removal permits the components to be mixed. Removable membranes may be glass, plastic, rubber, etc.

Kits may also be supplied with instructional materials. Instructions may be printed on paper or other substrate, and/or may be supplied as an electronic-readable medium, such as a floppy disc, CD-ROM, DVD-ROM, Zip disc, videotape, audiotape, flash memory device etc. Detailed instructions may not be physically associated with the kit; instead, a user may be directed to an internet web site specified by the manufacturer or distributor of the kit, or supplied as electronic mail.

Modification of Cupredoxin, Cupredoxin Entry Domains and Variants, Derivatives and Structural Equivalents Thereof Cupredoxin or variant, derivative or structural equivalents thereof may be chemically modified or genetically altered to produce variants and derivatives as explained above. Such variants and derivatives may be synthesized by standard techniques. Cupredoxin entry domains may be similarly modified.

In addition to naturally-occurring allelic variants of cupredoxin, changes can be introduced by mutation into cupredoxin coding sequence that incur alterations in the amino acid sequences of the encoded cupredoxin that do not significantly alter the ability of cupredoxin to inhibit the development of premalignant lesions. A "non-essential" amino acid residue is a residue that can be altered from the wild-type sequences of the cupredoxin without altering pharmacologic activity, whereas an "essential" amino acid residue is required for such pharmacologic activity. For example, amino acid residues that are conserved among the cupredoxins are predicted to be particularly non-amenable to alteration, and thus "essential."

Amino acids for which conservative substitutions that do not change the pharmacologic activity of the polypeptide can be made are well known in the art. Useful conservative substitutions are shown in Table 3, "Preferred substitutions." Conservative substitutions whereby an amino acid of one class is replaced with another amino acid of the same type fall within the scope of the invention so long as the substitution does not materially alter the pharmacologic activity of the compound.

TABLE 3

| Preferred substitutions | | |
|---|---|---|
| Original residue | Exemplary substitutions | Preferred substitutions |
| Ala (A) | Val, Leu, Ile | Val |
| Arg (R) | Lys, Gln, Asn | Lys |
| Asn (N) | Gln, His, Lys, Arg | Gln |
| Asp (D) | Glu | Glu |
| Cys (C) | Ser | Ser |
| Gln (Q) | Asn | Asn |
| Glu (E) | Asp | Asp |

TABLE 3-continued

| Preferred substitutions | | |
|---|---|---|
| Original residue | Exemplary substitutions | Preferred substitutions |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala, Tyr | Leu |
| Pro (P) | Ala | Ala |
| Ser (S) | Thr | Thr |
| Thr (T) | Ser | Ser |
| Trp (W) | Tyr, Phe | Tyr |
| Tyr (Y) | Trp, Phe, Thr, Ser | Phe |
| Val (V) | Ile, Leu, Met, Phe, Ala, Norleucine | Leu |

Non-conservative substitutions that affect (1) the structure of the polypeptide backbone, such as a β-sheet or α-helical conformation, (2) the charge, (3) hydrophobicity, or (4) the bulk of the side chain of the target site can modify the pharmacologic activity. Residues are divided into groups based on common side-chain properties as denoted in Table 4. Non-conservative substitutions entail exchanging a member of one of these classes for another class. Substitutions may be introduced into conservative substitution sites or more specifically into non-conserved sites.

TABLE 4

| Amino acid classes | |
|---|---|
| Class | Amino acids |
| hydrophobic | Norleucine, Met, Ala, Val, Leu, Ile |
| neutral hydrophilic | Cys, Ser, Thr |
| acidic | Asp, Glu |
| basic | Asn, Gln, His, Lys, Arg |
| disrupt chain conformation | Gly, Pro |
| aromatic | Trp, Tyr, Phe |

The variant polypeptides can be made using methods known in the art such as oligonucleotide-mediated (site-directed) mutagenesis, alanine scanning, and PCR mutagenesis. Site-directed mutagenesis (Carter, Biochem J. 237:1-7 (1986); Zoller and Smith, Methods Enzymol. 154:329-350 (1987)), cassette mutagenesis, restriction selection mutagenesis (Wells et al., Gene 34:315-323 (1985)) or other known techniques can be performed on the cloned DNA to produce the cupredoxin variant DNA.

Known mutations of cupredoxins can also be used to create variant cupredoxin to be used in the methods of the invention. For example, the C112D and M44KM64E mutants of azurin are known to have cytotoxic and growth arresting activity that is different from the native azurin, and such altered activity can be useful in the treatment methods of the present invention.

A more complete understanding of the present invention can be obtained by reference to the following specific Examples. The Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations. Modifications and variations of the invention as hereinbefore set forth can be made without departing from the spirit and scope thereof.

EXAMPLES

Example 1. Effect of Peptide P-28 on DMBA-Induced Mammary Lesions in the MMOC Model The mouse mammary gland organ culture (MMOC) model allows evaluating efficacy of potentially chemopreventive agents against development of mammary alveolar lesions (MAL) or mammary ductal lesions (MDL) in response to DMBA. DMBA under appropriate incubation conditions form either MAL or MDL based on the hormonal milieu in the medium. Hawthorne et al., Pharmaceutical Biology 40: 70-74 (2002); Mehta et al., J. Natl. Cancer Inst. 93: 1103-1106 (2001). Estrogen and progesterone-treated glands in culture develop ductal lesions whereas aldosterone and hydrocortisone-treated glands form estrogen and progesterone-independent alveolar lesions. Mammary glands not exposed to a carcinogen or chemopreventive agent, undergo structural regression in the absence of growth-promoting hormones, whereas treatment with DMBA for the 24-hr period between days 3 and 4 prevents the regression of structures caused by deprivation of hormones. It is assumed that this is because the glands have lost normal hormonal responsiveness and now have altered their course of development. Generating mammary adenocarcinoma by transplanting transformed cells into syngeneic mice has proved the premalignant preneoplastic nature of these unrepressed areas.

The thoracic pair of mammary glands was excised aseptically from each Balb/c mouse, and the glands were divided into several groups. The effects of p28 were evaluated at 4 different dilutions in the medium. Carcinogen treated glands without the test agent served as a measure to determine percent incidence in the absence of a chemopreventive agent. An additional control was included to serve as a positive control for chemoprevention. Azurin was included in the medium at 50 µg/ml concentration. For alveolar lesions (MAL) stained glands were evaluated for the incidence of lesions (glands containing any lesions as compared to total number of glands in a given treatment group). For the ductal lesions (MDL) similar protocol was adapted, however, as indicated below in the methods section the hormonal combination is different for alveolar and ductal lesions. The glands were fixed in formalin and then processed for histopathology. The sections are stained with eosin and hematoxelene and evaluated under microscope. Here the multiplicity of ductal lesions between the control and the treatment groups are compared.

Organ Culture Procedure.

The experimental animals used for the studies were young, virgin BALB/c female mice 3 to 4 weeks of age obtained from Charles River, Wilmington, Mass. The mice were treated daily by subcutaneous injections with 1 µg estradiol-17β+1 mg progesterone for 9 days. This treatment is a prerequisite inasmuch as animals not pretreated with steroids fail to respond to hormones in vitro. The entire culture procedure is described in detail. Jang et al., Science 275:218-220 (1997); Mehta, Eu. J. Cancer 36:1275-1282 (2000); Mehta et al., J. Natl. Cancer Inst. 89:212-219 (1997); Mehta et al., J. Natl. Cancer Inst. 93:1103-1106 (2001).

Briefly, the animals were killed by cervical dislocation, and the thoracic pair of mammary glands were dissected out on silk rafts and incubated for 10 days in serum free Waymouth MB752/1 medium (5-glands/5 ml/dish). The medium was supplemented with glutamine, antibiotics (penicillin and streptomycin 100 units/ml medium) and growth-promoting hormones, 5 µg insulin (I), 5 µg prolactin (P), 1 µg aldosterone (A) and 1 µg hydrocortisone (H) per ml of medium for the protocol to induce mammary alveolar lesions (MAL). For induction of ductal lesions (MDL), the medium contained 5 µg/ml, 5 µg/ml P, 0.001 µg/ml estradiol 17β and 1 µg/ml progesterone (Pg). Mehta et al., J. Natl. Cancer Inst. 93:1103-1106 (2001). The carcinogen, DMBA (2 µg/ml) was added to the medium between days 3 and 4. For the present study, DMBA was dissolved in DMSO at a final concentration of 4 mg/ml, and 50 µg I was added to 100 ml medium resulting in 2 µg/ml final concentrations. The control dishes contained DMSO as vehicle.

On day 4, DMBA is removed from the medium by rinsing the glands in fresh medium and transferring them to new dishes containing fresh medium without DMBA. After 10 days of incubation, the glands were maintained for another 14 days in the medium containing only I (5 µg/ml). During the entire culture period, the glands were maintained at 37° C. under 95% $O_2$ and 5% $CO_2$ environment. The chemopreventive agent was included in the medium during the first ten days of growth-promoting phase. The test peptide p28 was evaluated at 4 concentrations ranging from 12.5 µg/ml to 100 µg/ml. Azurin was evaluated at 50 µg/ml in the medium. The peptide was dissolved in sterile water and filtered prior to use. The medium was changed three times per week (Monday, Wednesday and Friday). At the end of the exposure, the glands were fixed in formalin.

Results were analyzed by Chi-square analysis and Fisher's Exact Test.

Morphometic Analysis of MAL.

For examination of MAL, the glands were stained in alum carmine, and evaluated for the presence of the lesions. The glands were scored for the presence or absence of mammary lesions, severity of lesions per gland, and toxicity of the agent. The glands stored in xylene were evaluated for the presence or absence, incidence, and severity of mammary lesions for each gland under a dissecting microscope. Mammary glands were scored as positive or negative for mammary lesions, and the percent incidence was determined as a ratio of glands exhibiting lesions and the total number of glands in that group. Dilation of ducts or disintegration of mammary structure because of treatment with chemopreventive agent was considered a toxic effect. The data were subjected to statistical analysis for the incidence to determine the effectiveness of the potential chemopreventive agents.

FIG. 1A shows a representative photograph of alveolar lesions in a DMBA treated gland and its comparison with a gland that was treated with DMBA along with a chemopreventive agent. The effects of p28 on the development of alveolar lesion are shown in FIGS. 1B-1F and summarized in FIG. 2. The peptide p28 inhibited MAL formation by 67% at 25 µg/ml concentration. Increasing concentration further up to 100 µg/ml did not enhance the efficacy of the peptide. The comparison of the peptide with azurin indicated that p28 was as effective as azurin for MAL development. Azurin at 50 µg/ml concentration resulted in a 67% inhibition. Statistical analyses indicated that the effect of p28 was statistically significant compared to DMBA control at concentrations greater than 12.5 µg/ml ($p<0.01$, Fisher's Exact Test; Chi Square analysis).

Histopathological Evaluation of MDL.

For MDL, the glands were processed for histopathological evaluations. The glands were sectioned longitudinally into 5-micron sections and stained with eosin hematoxeline. The longitudinal section of each gland was divided into several fields and each field was evaluated for ductal lesions. Mehta et al., J. Natl. Cancer Inst. 93:1103-1106 (2001). Briefly, the entire gland is evaluated under the scope; smaller glands will have fewer total fields as compared to larger glands. Thus, each gland will have variable number of fields. Often the number of sections through the ducts also varies greatly from gland to gland. This results in the variable number from group to group. Fields containing ductal hyperplasia or atypia were determined and were compared with total number of field evaluated for each gland. No discrimination is made between the hyperplasia or atypia and severely occluded glands. Any field containing any of these histological patterns was considered positive for the lesion. The treatment groups were compared with the controls for the severity and percent inhibition was calculated.

Figure 3:
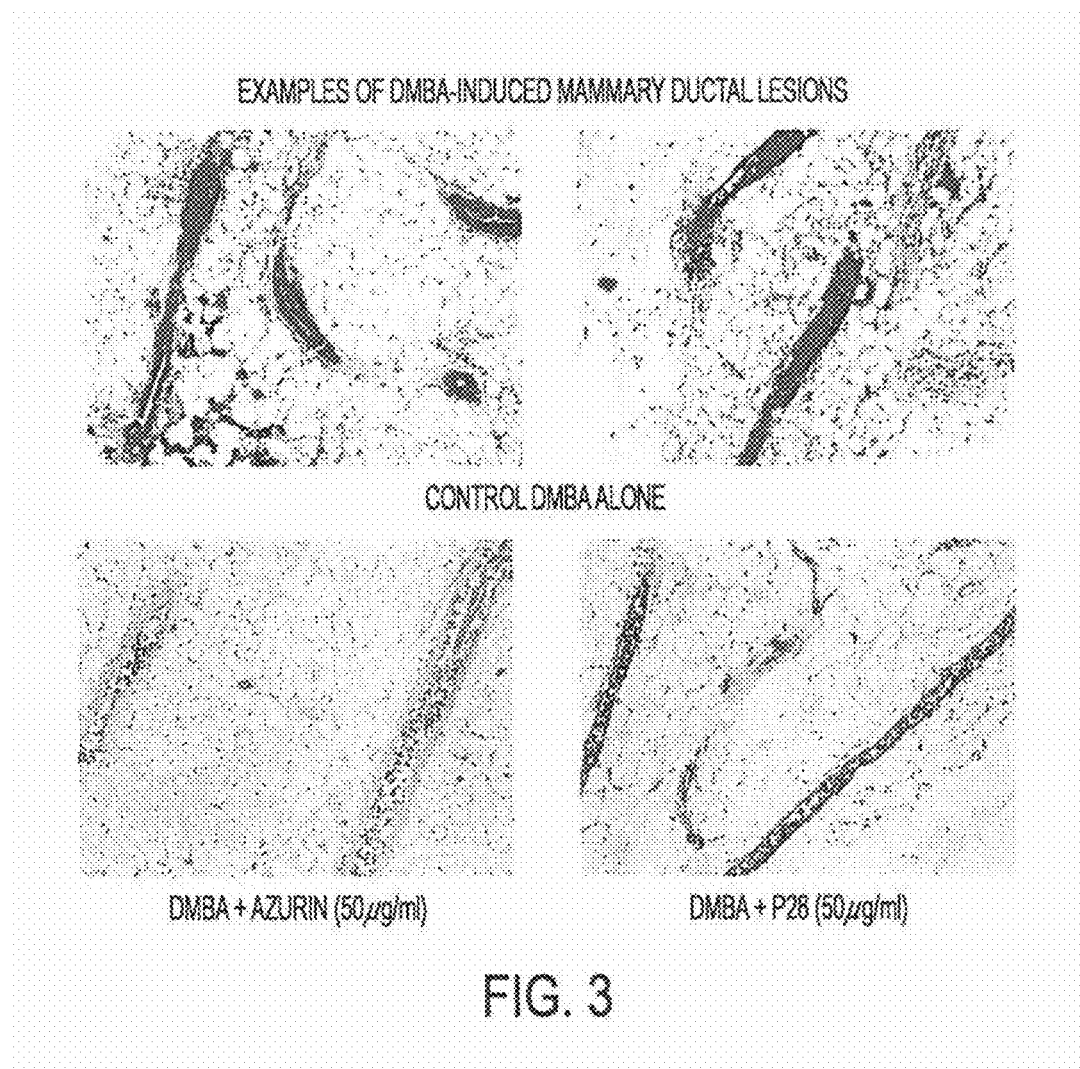
FIG. 3 depicts photographs of representative sections of ductal lesions and effect of p28.
Figure 4:
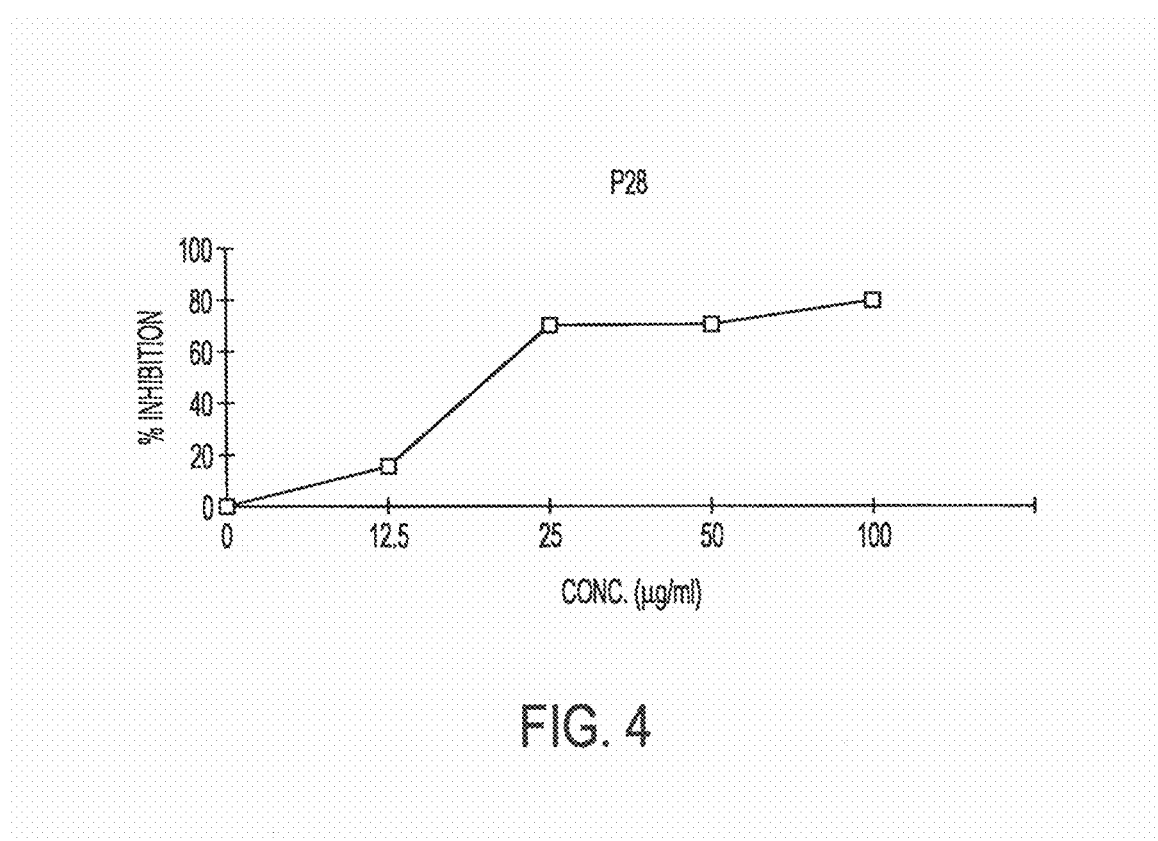
FIG. 4 depicts a graph showing the efficacy of p28 against DMBA-induced ductal lesions FIG. 5. Diagram showing the localization of the α-helix in wt-azurin as well as in the wt-azurin 50-77 protein transduction domain. Replacement of three amino acids in the azurin 50-77 domain by proline residues is indicated.

FIG. 3 shows a representative ductal lesion. DMBA induces ductal lesions varying from hyperplasia, atypia to complete occlusion of the ducts. A ratio of ductal lesions/total number of ductal sections was determined. Again, 12.5 µg/ml concentration of p28 suppressed only 15% of the MDL formation. However, at 25 µg/ml there was a significant inhibition of the lesions comparable to that observed with 50 µg/ml azurin. The efficacy of p28 at concentrations greater than 12.5 µg/ml was statistically significant (p<0.01, Fishers Exact Test). These results are summarized in FIG. 4. Often effects of chemopreventive agents can be differentiated between the MAL and MDL. For example tamoxifen inhibited the development of MDL but not MAL. It is interesting to note that azurin and p28 inhibited both estrogen and progesterone-dependent ductal lesions as well as independent alveolar lesions.

This example indicates that both p28 and azurin can prevent the development of precancerous lesions in breast tissue. Thus, p28 and azurin may be used as chemopreventive agents in mammalian patients.

Example 2. Selective Penetration of Cancer Cells by Cupredoxins and Derivative Peptides as Potential Vectors for Gene Delivery We demonstrated that azurin a member of the cupredoxin family of proteins, isolated from *Pseudomonas aeruginosa* enters cancer cells and induces a p53-mediated apoptosis in vitro and in vivo. The selectivity of penetration of cationic and anionic cupredoxins and derived peptides as potential vectors for gene delivery was evaluated. The following cupredoxins were tested: azurin (14 kDa, pI 5.7), rusticyanin (17 kDa, pI 8.0), and plastocyanin (11 kDa, pI 5.4). The results indicated that azurin had the most selective penetration.

25 amino acid (a.a.) fragments of azurin (azu) were synthesized and evaluated for their penetration into a variety of cancer and histologicaly matched normal cells. Confocal microscopic and flow cytometric (FACS) analysis demonstrated that an 18 amino acid (1.7 kDa, azu 50-67) fragment (p18) labeled with Alexafluor 568 (800 Da) selectively penetrated human melanoma (Mel-2,7,29), breast (MCF-7), ovarian (SK-OV3), pancreatic (CAPAN-2), glioblastoma (LN-229), astrocytoma (CCF-STTG1), prostate (LN-CAP), and kidney (ACHN-CRL1611) cell lines, but not their respective controls. LDH release and hemolysis assays showed that p18 did not disrupt cancer cell membrane structure during penetration or produce hemolysis of human erthrocytes, suggesting that p18 penetrates human cancer cells without disrupting membrane structure. Pretreatment of Mel-2 cells with specific inhibitors of cell internalization (cytochalasin D; inhibition of actin polymerization, taxol; inhibition of microtubule depolymerization, chlorpromazine; inhibition of clathrin-mediated endocytosis, sodium azide; metabolic inhibition, or staurosporine; cell cycle inhibition) had a negligible effect on the penetration of p18. However, incubation of Mel-2 cells with nystatin (caveolae formation inhibitor) and brefeldin A (golgi apparatus disruptor) significantly inhibited the penetration of p18, suggesting that endocytic processes may, in part, be involved in the penetration of p18. Imaging of p18 labeled with an infrared dye ($\lambda_{em}$ 800 nm) in athymic mice bearing xenografted melanoma tumors clearly demonstrated selective uptake in primary s.c. tumors and distant organ metastases without accumulating in normal organs and tissues. As such, the peptides of the present invention, including in one embodiment, p18 appear to have significant utilization as a non-viral vector for gene (or any DNA/RNA fragment) therapy.

Example 3—Plasmid Constructions

Figure 5:
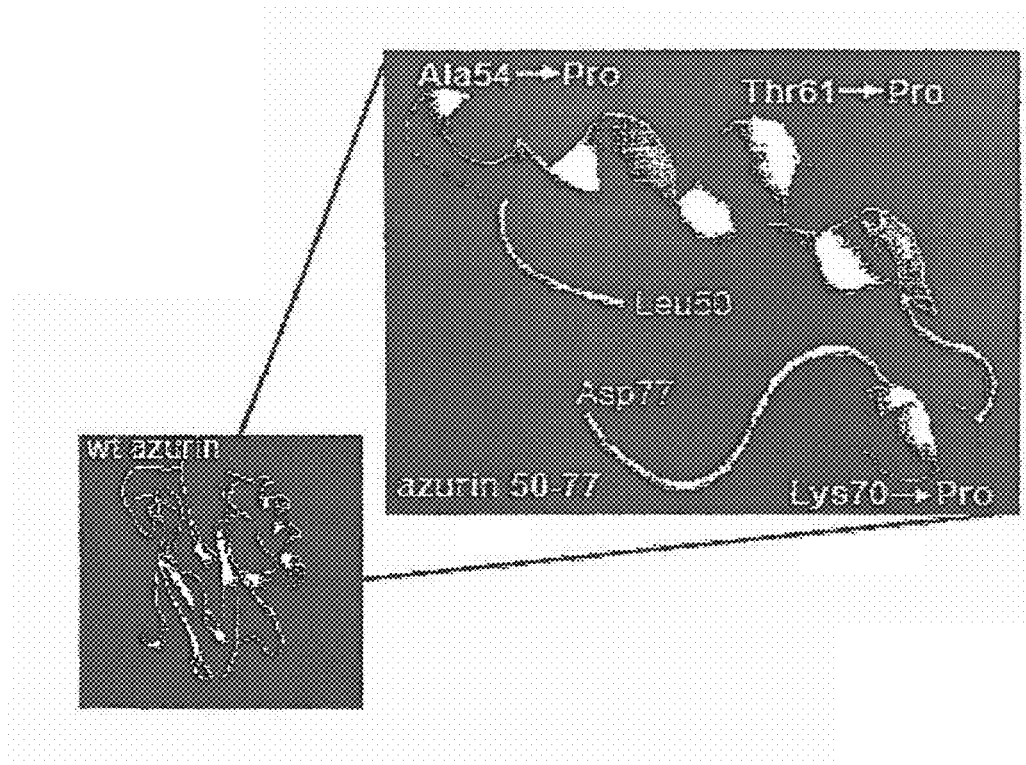

Plasmids expressing fusion glutathione S-transferase (GST)-truncated wt-azurin (azu) derivatives were constructed by a polymerase chain reaction using proofreading DNA polymerase. FIG. 5 shows a schematic representation of various truncated wt-azurin constructs. For pGST-azu 36-128 (SEQ ID NO: 34), an amplified PCR fragment was introduced into the BamH1 and EcoR1 sites of the commercial GST expression vector pGEXSX (Amersham Biosciences, Piscataway, N.J. 08855). The fragment was amplified with pUC19-azu as a template and primers, 5'-CGGGATCC CCG GCA ACC TGC CGA AGA ACG TCA TGG GC-3' (SEQ ID NO: 35) and 5'-CGGAATTC GCA TCA CTT CAG GGT CAG GG-3' (SEQ ID NO: 36), where the additionally introduced BamHI and EcoRI sites are underlined respectively. Carboxyl-terminus truncation of azu gene was cumulatively performed by introducing a stop codon using QuickChange site-direct mutagenesis kit (Stratagene, La Jolla, Calif. 92037).

For pGST-azu 36-50 (SEQ ID NO: 37), pGST-azu 36-77 (SEQ ID NO: 38) and pGST-azu 36-89 (SEQ ID NO: 39), stop codons were introduced into Ser51, Ser78, and Gly90, respectively. The plasmid carrying pGST-azu 36-128 was used as template DNA. Three sets of oligonucleotides for site-direct mutagenesis are shown as follows. For pGST-azu 36-50: 5'-GGC CAC AAC TGG GTA CTG TGA ACC GCC GCC GAC ATG CAG-3' (SEQ ID NO: 40), and 5'-CTG CAT GTC GGC GGC GGT TCA CAG TAC CCA GTT GTG GCC-3' (SEQ ID NO: 41). For pGST-azu 36-77: 5'-CCT GAA GCC CGA CGA CTG ACG TGT CAT CGC CCA CAC C-3' (SEQ ID NO: 42) and 5'-GGT GTG GGC GAT GAC ACG TCA GTC GTC GGG CTT CAG G-3' (SEQ ID NO: 43). For pGST-azu 36-89: 5'-CCA AGC TGA TCG GCT CGT GAG AGAAGG ACT CGG TGA CC-3' (SEQ ID NO: 44), and 5'-GGT CAC CGA GTC CTT CTC TCA CGA GCC GAT CAG CTT GG-3 (SEQ ID NO: 45). The plasmids pGST-azu 50-77 and pGST-azu 67-77 were generated by PCR using pGST-azu 36-77 as a template DNA.

Amplified PCR fragments, azu 50-77 and azu 67-77, were obtained using forward primers 5'-CGGGATCC TGA GCA CCG CCG CCG ACA TGC AGG G-3' (SEQ ID NO: 46) and 5'-CGGGATCC CCG GCC TGG ACA AGG ATT ACC TGA AGC CCG-3 (SEQ ID NO: 47), where the additionally introduced BamHI site is indicated by underlining. The reverse primer, 5'-CG<u>GAATTC</u> GCA TCA CTT CAG GGT CAG GG-3' (SEQ ID NO: 48), was utilized in both cases.

The plasmid carrying gst-azu 50-77 was used for generating pGST-azu 50-66 by introduction of a stop codon in Gly67 using oligonucleotides as follows: 5'-GAC GGC ATG GCT TCC TGA CTG GAC AAG GAT TAC C-3' (SEQ ID NO: 49), and 5'-GGT AAT CCT TGT CCA GTC AGG AAG CCA TGC CGTC-3' (SEQ ID NO: 50). The green fluorescent protein gene (gfp) encoding the green fluorescent protein was also amplified by PCR. Forward and reverse primers used were 5'-CGGGATCC CCA TGG TGA GCA AGGGCG-3' (SEQ ID NO: 51) and 5'-CGGAATTC CTT GTA CAG CTC GTC CAT GCC G-3' (SEQ ID NO: 52) containing BamHI and EcoRI sites at the 5' end of each oligonucleotides. The resultant PCR fragment was ligated into the pGEXSX vector for creating pGST-GFP. For the preparation of plasmid DNA carrying gst-gfp-azu 50-77, the azu 50-77 gene was amplified by PCR with pGST-azu 50-77 as a template and primers 5'-CCG<u>CTCGAG</u> CCT GAG CAC CGC CGC CATGCA GGG-3' (SEQ ID NO: 53) and 5'-TTTTCCTTTTGC<u>GGCCGC</u> TCA GTC GTC GGG CTT CAG GTA ATC C-3' (SEQ ID NO: 54), where the introduced Xho I and Not I sites are underlined respectively. Purified azu 50-77 fragment was introduced into pGST-GFP at Xho I and Not I unique restriction enzyme sites Example 4—Purification of Proteins Wt-azurin and M44KM64E mutant azurin were prepared and purified as described by Yamada, T. et al. Proc. Natl. Acad. Sci. USA, vol. 101, pp. 4770-75 (2004), and in copending U.S. patent application Ser. No. 10/720,603, the contents of which are incorporated by this reference. Briefly, the wt-azurin gene was amplified by PCR according to the method described by Kukimoto et al., FEBS Lett, vol. 394, pp 87-90 (1996). PCR was performed using genomic DNA from *P. aeruginosa* strain PAO1 as a template DNA.

The amplified DNA fragment of 545 bp, digested with HindIII and PstI, was inserted into the corresponding sites of pUC19 so that the azurin gene was placed down-stream of the lac promoter to yield an expression plasmid pUC19-azuA. *E. coli* JM109 was used as a host strain for expression of the azurin gene. The recombinant *E. coli* strain was cultivated in 2YT medium containing 50 µg ml ampicillin, 0.1 mM IPTG; and 0.5 mM $CuSO_4$ for 16 h at 37° C. to produce azurin.

For preparation of the M44KM64E mutant azurin, site-directed mutagenesis of the azurin gene was performed using a QuickChange site-directed mutagenesis kit (Stratagene, La Jolla, Calif.). Mutations were confirmed by DNA sequencing.

Plasmid DNA, pET9a carrying the rus gene encoding the cupredoxin rusticyanin from *Acidithiobadilus ferrooxidans*, was obtained from Dr. Kazuhiko Sasaki, Central Research Institute of Electric Power Industry, Chiba, Japan.

Rusticyanin was isolated from *E. coli* BL21 (DE3) harboring the rus gene using the method of Sasaki, K., et al. Biosci. Biotechnol. Biochem., vol. 67, pp. 1039-47 (2003) with some modifications. Briefly, acetic acid buffer (pH 4.0) and CM-Sepharose (Sigma Chemicals, St. Louis, Mo. 63178) were used instead of beta-alanin buffer (pH 4.0) and TSK-gel CM-650 column (Tosoh Bioscience, LLC, Montgomeryville, Pa. 18936). Two other purified cupredoxins, plastocyanin from *Phormidium laminosum* and pseudoazurin from *Achromobacter cycloclastes* were obtained from Dr. Beatrix G. Schlarb-Ridley, University of Cambridge, UK and Dr. Christopher Dennison, University of Newcastle Upon Tyne, UK, respectively.

All recombinant GST-fusion derivatives were purified as follows: *E. coli* BL21 cells were used as the host strain. After induction with 0.4 mM IPTG at early log phase of growth in L broth, GST-fusion proteins were purified from cell extracts by using Glutathione Sepharose 4B affinity chromatography and Sephadex 75 gel-filtration column with PBS (Amersham Biosciences, Piscataway, N.J. 08855). Purified proteins, wt azurin and GST-derivatives or other cupredoxins, labeled with ALEXA FLUOR® (Molecular Probes, Inc., Eugene, Oreg. 97402) were isolated according to manufacturer's instructions. Unbound free fluorescent chemical was removed by gel-filtration column.

Example 5—Cell Cultures

J774 and UISO-Mel-2 cells (available from Frederick Cancer Research and Development Center, Frederick, Md. U.S.A.) were cultured as described in Yamada, T. et al. Infect. Immun. vol. 70, pp. 7054-62 (2002); Goto, M., et al. Mol. Microbiol. vol. 47, pp. 549-59 (2003); and Yamada, T., et al. Proc. Natl. Acad. Sci. USA vol. 99, pp. 14098-103 (2002), the contents of which are incorporated by reference. Human normal fibroblast cells (stock culture collection of the Department of Surgical Oncology, University of Illinois at Chicago (UIC), Chicago) were cultured in MEM with Eagle's salt containing 2 mM L-glutamine, 0.1 mM MEM essential amino acids and supplemented with 10% heat inactivated fetal bovine serum, 100 Units/ml penicillin and 100 µg/ml streptomycin. MCF-7 and MOF-10F cells were cultured as described in Punj et al. *Oncogene* 23:2367-78 (2004).

Example 6—Co-Culture of J774, UISO-Mel-2 and Fibroblast Cells and Confocal Microscopy J774, UISO-Mel-2, and fibroblast cells were cultured on individual cover slips. After overnight incubation, the cells were washed with fresh media and all three cell lines were placed on a culture dish containing 200 µg/ml of wt-azurin conjugated with ALEXA FLUOR® 568. The cells were then incubated for 0.5 or 3.5 h at 37° C. under 5% $CO_2$.

For preparation of microscope samples, cells were cultured on cover-slips overnight at 37° C. Cultured cells were placed at 37° C. or 4° C. for 2 h before protein treatment. Pre-warmed 37° C. fresh media or ice-cold 4° C. fresh media were mixed with red-fluorescent (labeled with ALEXA FLUOR® 568) cupredoxins or GST-fusion derivatives, and incubated with the cells. The cells were washed with PBS, and fixed with methanol at −20° C. for 5 min. After washing with PBS twice and the addition of mounting media containing 1.5 µg/ml 4',6-diamidino-2-phenylindole (DAPI) for staining nuclei (VECTASHILD, Vector, Burlingame, Calif.), images were taken by a confocal microscope.

Example 7. Entry of Cupredoxins into J774 Cells

Wt-azurin, its mutant variant M44KM64E, plastocyanin, pseudoazurin and rusticyanin were incubated with J774 cells as in Example 6 and the cells examined using confocal microscopy. In these experiments, the cupredoxins were conjugated with ALEXA FLUOR® 568 to fluoresce red and incubated with the J774 cells for 1 hr at 37° C. at a concentration of 200 µg/ml, and in a separate experiment wild type azurin and rusticyanin were incubated with J774 cells for 1 hr at 37° C. at a concentration of about 6 to 7 µM. The nucleus was stained blue with DAPI. A control without the proteins was maintained. In all cases, the cupredoxins were seen to enter into the cytosol of J774 cells. In similar experiments, auracyanin A and B enter preferentially to MCF7 cancer cells and not non-cancerous control cells.

Example 8. Entry of Wt-Azurin and Rusticyanin into Various Cell Types

Wt-azurin exhibits a reduced cytotoxic activity towards MCF-10F cells as contrasted with the MCF-7 cells. Punj et al. *Oncogene* 23:2367-2378 (2004). J774, peritoneal macrophages, mast cells, human breast cancer MCF-7 and human normal epithelial MCF-10F cells (stock culture collection of the Department of Surgical Oncology, University of Illinois at Chicago (UIC), Chicago) were treated and examined as in Example 5 and tested to determine if wt-azurin could enter such cells.

Wt-azurin was internalized in J774 cells during 45 mm incubation. However, it was internalized very inefficiently in peritoneal macrophages or mast cells. Even after 6 hr incubation, such cells showed only limited entry. Similarly, while wt-azurin entered the breast cancer MCF-7 cells efficiently, it showed an extremely reduced rate of entry in the normal mammary MCF-10F cells.

Alexa Fluor®-conjugated azurin entered efficiently in UISOMel-2 and MCF-7 cancer cells but not in the normal mammary MCF 10A1 cells. Alexa Fluor®-conjugated rusticyanin, however, not only entered the cytosol of UISO-Mel-2 and MCF-7 cancer cells, but also in the normal MCF 10A1 cells. Unlike in the cancer cells where rusticyanin was evenly distributed in the cytosol, in MCF10A1 cells, much of the rusticyanin was sequestered in the perinuclear space surrounding the nucleus.

Example 9. Wt Azurin-Mediated Cytotoxicity and Growth Inhibition

To further assess the specificity of entry of wt-azurin in various cells, we determined the entry of Alexa fluor-conjugated wt-azurin in J774, UISO-Mel-2 and normal fibroblast cells during incubation at 37° C. for 30 min and 3.5 hr. Wt-azurin was seen to enter rapidly in J774 and UISO-Mel-2 cells in 30 mm; very little wt-azurin was seen in the cytosol of fibroblasts during this period. After 3.5 hr of incubation, only small amounts of wt-azurin were found in the fibroblasts.

Figure 1B:
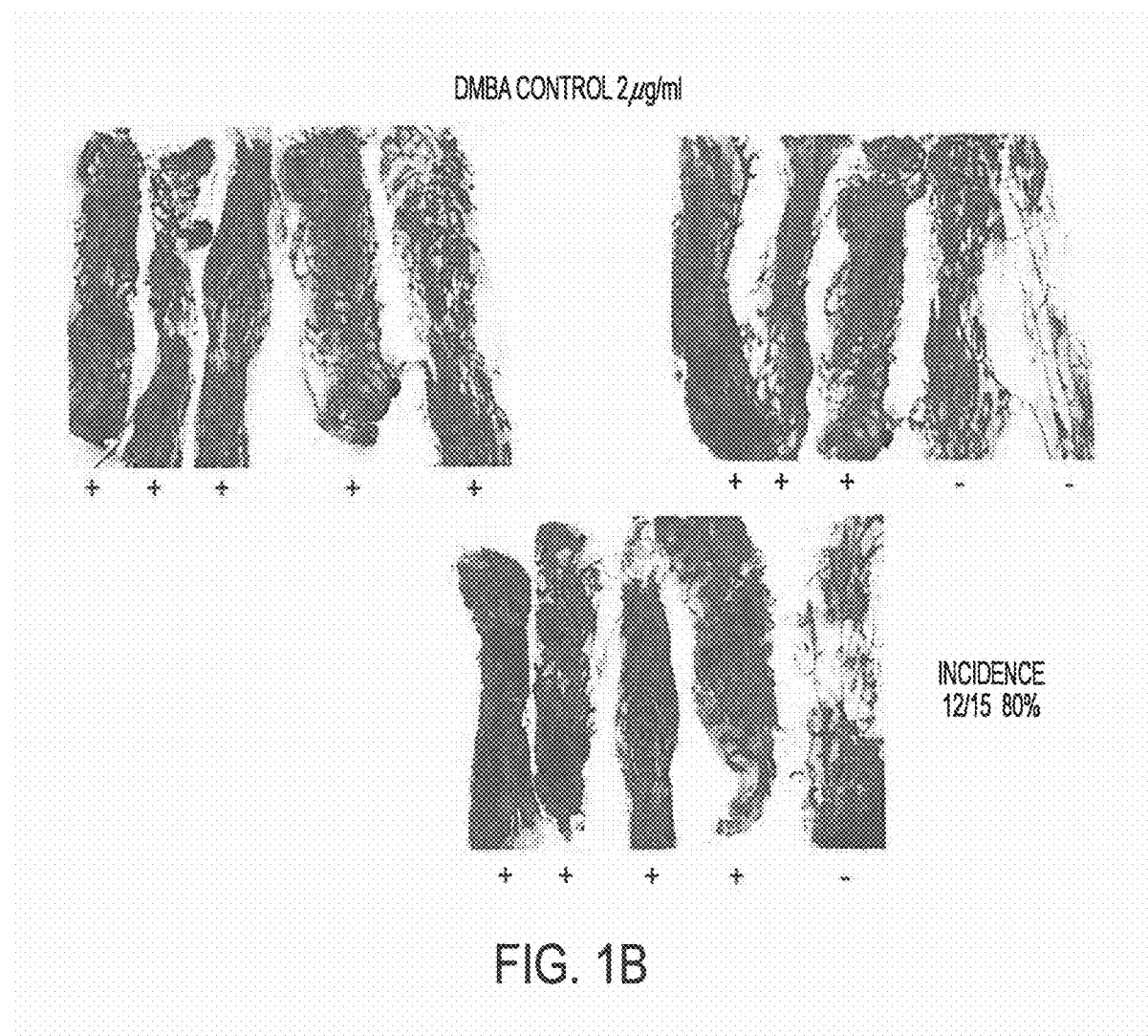
FIGS. 1B-1G show representative photographs of the effects of p28 on the development of alveolar lesions.
Figure 1C:
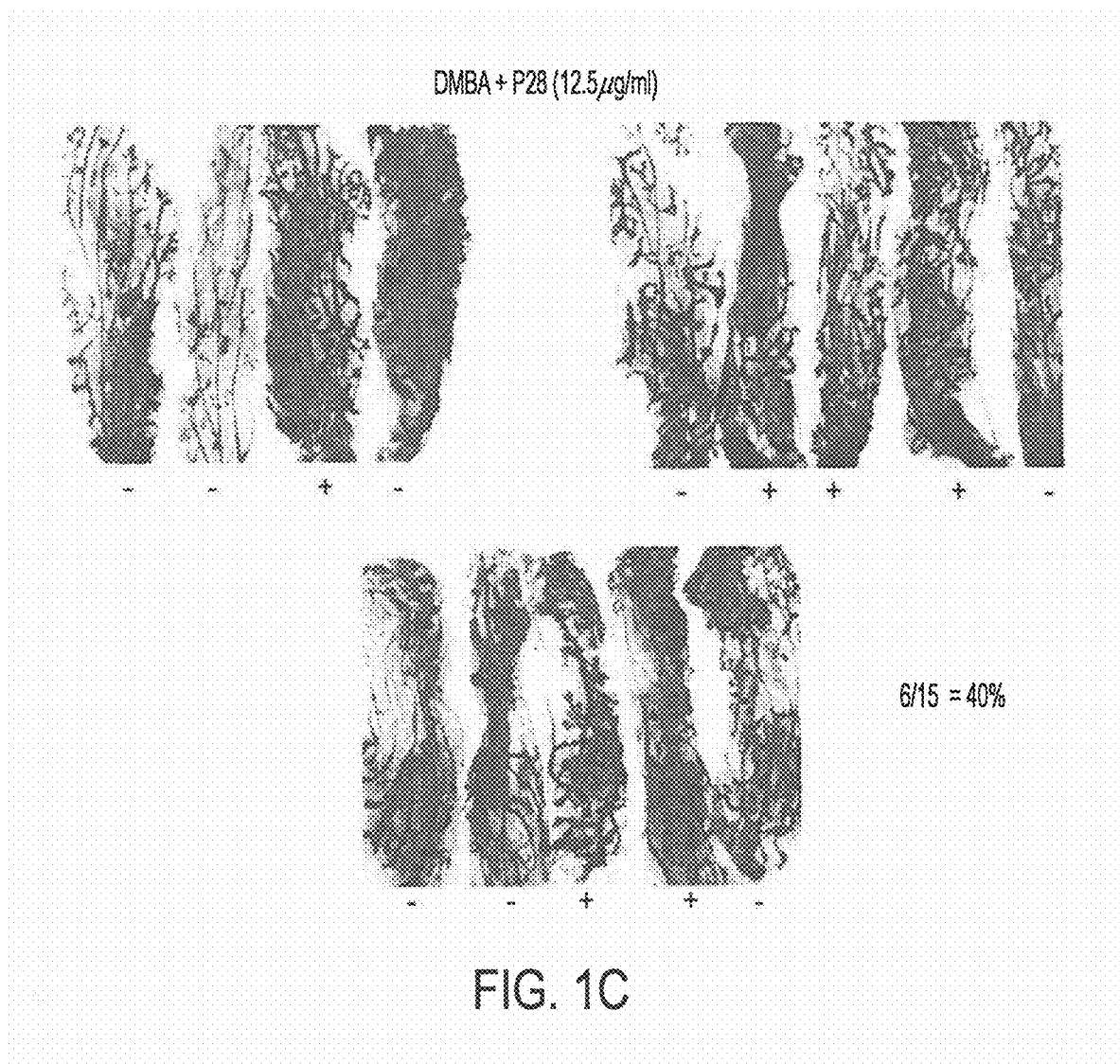
Figure 1D:
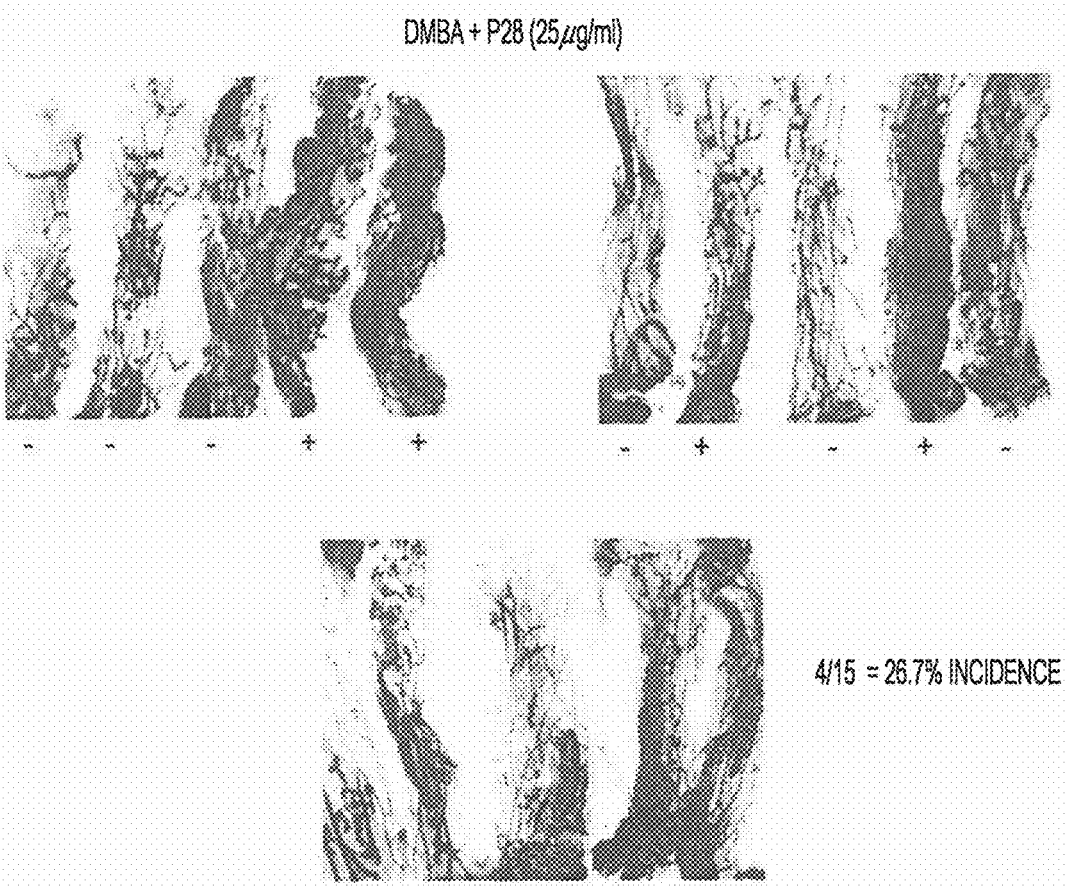
Figure 1E:
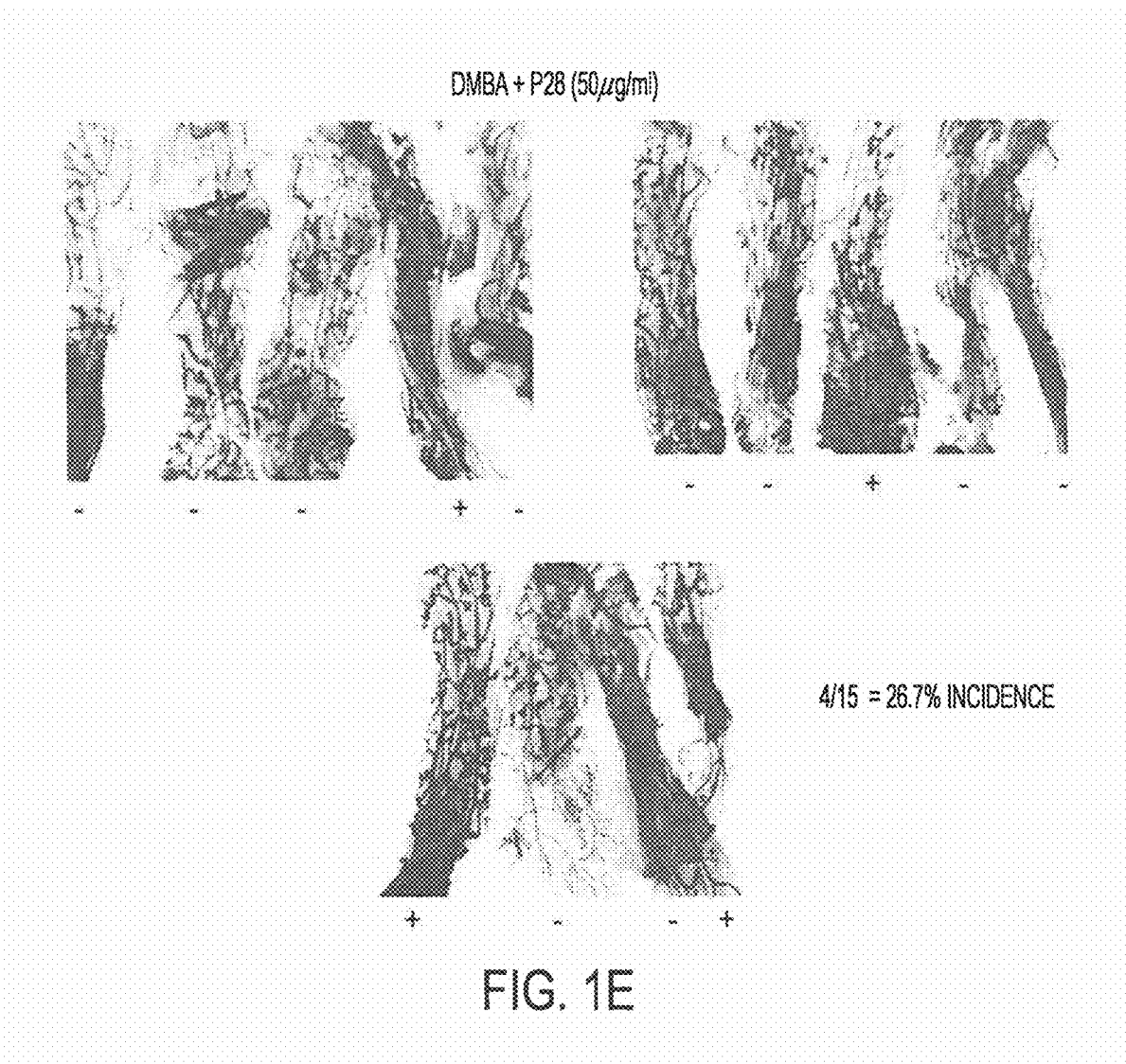
Figure 1F:
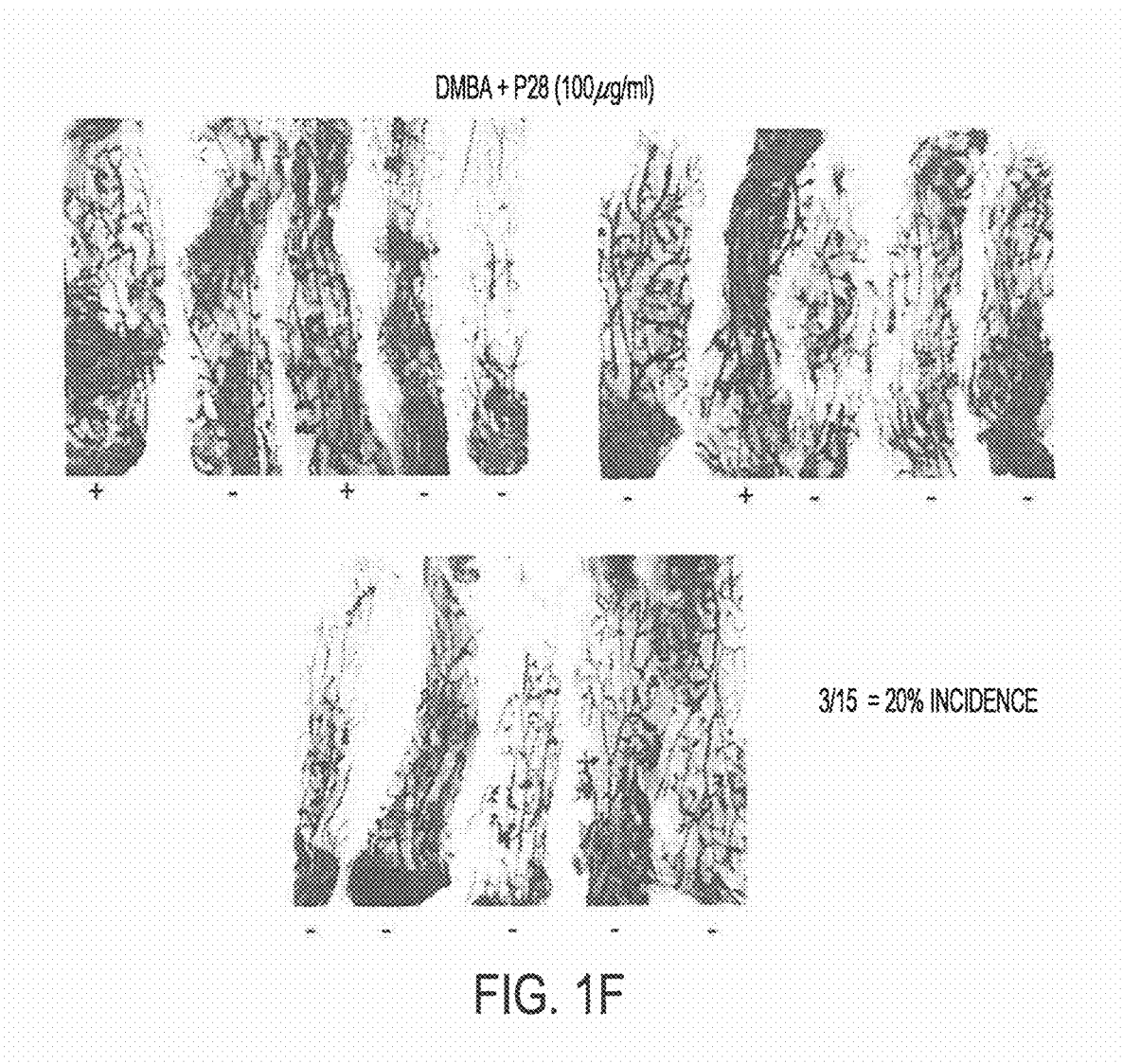
Figure 1G:
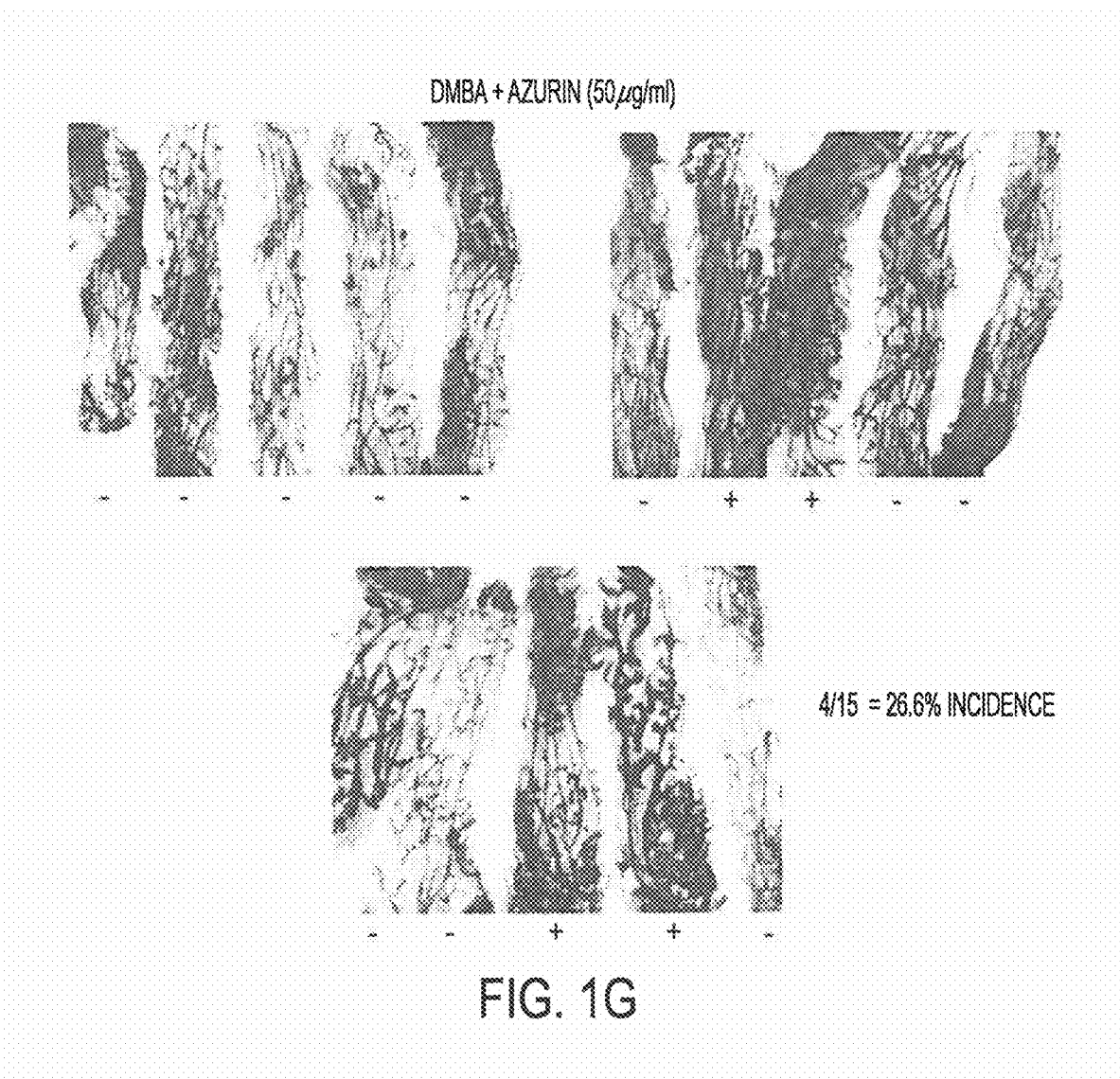
Figure 2:
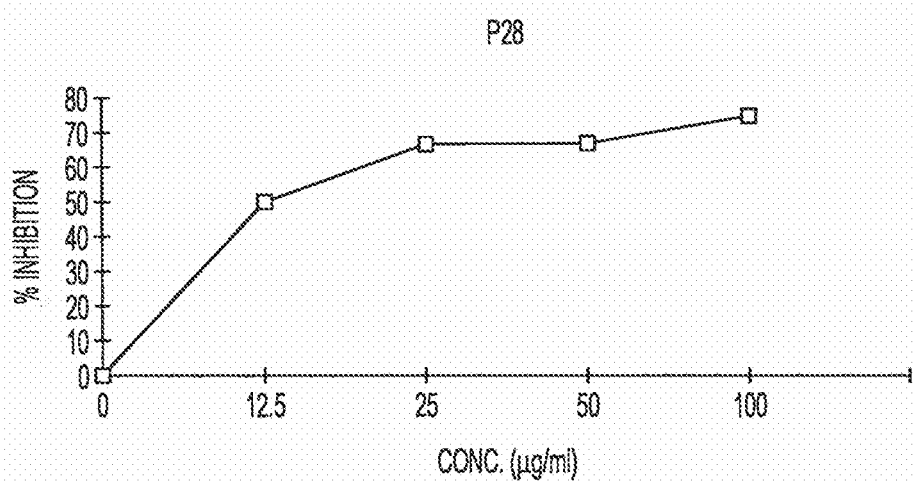
FIG. 2 depicts a graph showing the efficacy of p28 against DMBA-induced mammary alveolar lesions.

A 3(4,5 dimethylthiazol-2-yl-2,5 tetrazolium bromide) (MTT) assay was performed for the measurement of the cytotoxicity of wt-azurin as described by Yamada, T., et al. *Infect. Immun.* 70:7054-62 (2002), Goto, M., et al. *Mol. Microbiol.* 47:549-59 (2003), and in co-pending U.S. patent application Ser. No. 10/720,603, filed Nov. 24, 2003, the contents of which are incorporated by reference. FIG. 1(b) shows that significant wt-azurin-mediated cytotoxicity was observed only with J774 and UISO-Mel-2 cells during 24 hr incubation.

M44KM64E mutant azurin showed very little apoptosis-inducing activity in J774 cells but at 1 mg/ml concentration significantly inhibited (about 95%) cell cycle progression at the $G_1$ to S phase. Cell cycle progression was analyzed by flow cytometry, as described by Hiraoka, Y. et al., *Proc. Natl. Acad. Sci. USA, vol.* 101:6427-32 (2004) and Yamada, T. et al. *Proc. Natl. Acad. Sci. USA* 101:4770-75 (2004), the contents of which are incorporated by reference. FIG. 1(a) shows that when the fibroblasts were treated with 500 µg/ml or 1 mg/ml of M44KM64E mutant azurin, the extent of inhibition of cell cycle progression was about 20%.

Example 10. Microinjection of Wt-Azurin into Fibroblast and MCF-10F Cells

Wt-azurin was microinjected into fibroblast and MCF-10F cells as using the method described by Punj, V., et al., *Oncogene* 23:2367-78 (2004). Cells were examined for induction of apoptosis, leading to nuclear DNA condensation and fragmentation. Significant nuclear DNA (labeled blue with DAPI) condensation and fragmentation were observed in microinjected single cells after 5 hr incubation with wt-azurin, but not during a 30 min. incubation with azurin.

Example 11. Internalization of Wt-Azurin Fusion Derivatives at 37° C.

A series of GST fusions of wt-azurin truncated at both the N- and the C-terminal were prepared and purified as in Example 1 (FIGS. 2(a) and 2(b)). Using ALEXA FLUOR® 568 conjugated wt-azurin, GST and GST-azu fusion derivatives, internalization in J774 cells at 37° C. during 1 hr incubation was examined using the method described in Example 5. The nucleus was stained blue with DAPI.

While wt-azurin was internalized, GST remained at the periphery of the cells and was not internalized. GST-azu 36-128 and GST-azu 36-89 were internalized, as was GST-azu 36-77. Further truncations, however, demonstrated that while GST-azu 50-77 was internalized, GST-azu 36-50 was highly inefficient and appeared to form clumps on the surface.

Example 12. Internalization of Azurin Fusion Derivatives at 4° C.

Internalization of wt-azurin and the GST-azu fusion derivatives in J774 cells incubated at 4° C. was examined. At 4° C., internalization of wt-azurin inside J774 cells during 1 hr incubation was severely impaired. Similar impairment was also seen with GST-azu 36-128 and GST-azu 36-89. The shorter GST-azu 36-77, GST-azu 50-77, GST-azu 50-66 and GST-azu 67-77 demonstrated severe impairment of internalization at 4° C.

Figures 6A, 6B, 6C:
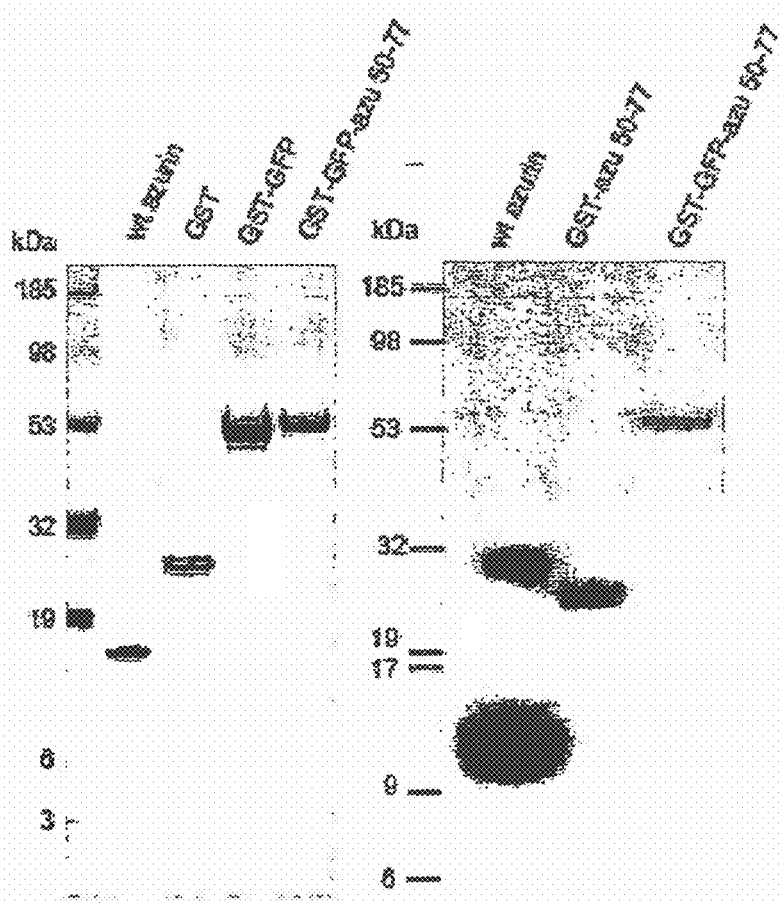
FIGS. 6 (A), (B) and (C). (A) Diagram showing construction of a GST-GFP-azu 50-77 fusion protein. The gfp gene was introduced at the 3'-end of the gst gene (for GST-GFP) and the azu 50-77 fragment was then ligated at the 3'-end of the gfp gene in frame to produce the GST-GFP-azu 50-77 fusion protein. GST-GFP-azu 50-77 was purified as a single fusion protein from the cell lysates. Purified proteins were run on SDS-PAGE and detected by Coomassie Blue staining (6(B)) and also by Western blotting using anti-azurin antibody (6(C)).

Example 13. Energy-Dependent Internalization of the GST-GFP-azu 50-77 Fusion Protein in J774 and Melanoma UISO-Mel-2 Cells GST was fused with GFP to make a GST-GFP fusion derivative. Additionally, azu 50-77 was fused to the GST-GFP ($M_r$ 53 kDa) fusion protein (FIG. 6(a)). The mobility of the purified GST, GST-GFP and GST-GFP-azu 50-77 fusion derivatives was examined on SDS-PAGE (FIG. 6(b)). Detection was by Coomassie Blue staining and Western blotting using anti-azurin antibody (FIG. 6(c))

Figures 7A, 7B, 7C:
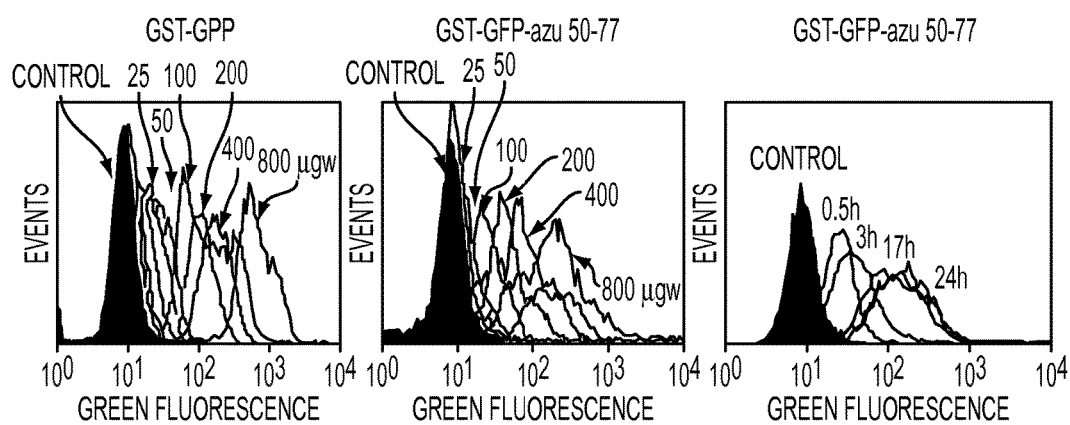
FIGS. 7 (A), (B) and (C). Diagrams showing a kinetic study for the internalization of GST-Green Fluorescent Protein (GFP) and GST-GFP-azurin fusion proteins. Green fluorescence was assayed in J774 cells treated with various concentrations of GST-GFP (10(a)) or GST-GFP-azu 50-77 (10(b)) at 37° C. for 1 hr. Ten thousand cells were analyzed by flow cytometry. (c) Time-dependence of internalization of GST-GFP-azu 50-77. J774 cells were incubated with 200 μg/ml GST-GFP-azu 50-77 for indicated times at 37° C. and analyzed by flow cytometry.

Flow cytometric determination of J774 cells treated with varying concentrations of GST-GFP showed that this protein does bind to J774 cells. Flow cytometric separation of J774 cells treated with increasing concentrations of GST-GFP-azu 50-77 fusion protein demonstrated significantly reduced fluorescence than GST-GFP alone (FIG. 7). It is to be noted that internalization of GFP in mammalian cells is known to lead to loss of fluorescence. This reduction of fluorescence is also apparent when J774 cells are treated with 200 µg/ml of GST-GFP-azu 50-77 fusion protein and incubated for increasing periods of time at 37° C.

To determine if there is any difference in the binding and internalization profile of GST-GFP and GST-GFP-azu 50-77, both J774 and UISO-Mel-2 cells were incubated with GST-GFP and GST-GFP-azu 50-77 at 37° C. and at 4° C. The green fluorescence was localized using confocal microscopy. In J774 cells, GST-GFP fusion protein bound to the surface and was not internalized both at 37° C. and at 4° C. In contrast, GST-GFP-azu 50-77 was found to be internalized at 37° C., but not at 4° C. In UISO-Mel-2 cells, the GST-GFP fusion protein was retained on the surface both at 37° C. and at 4° C. In contrast, similar to J774 cells, GST-GFP-azu 50-77 fusion protein was seen to be internalized at 37° C. but not at 4° C.

Example 14. Wt-Azurin Entry into Mammalian Cells by a Cell Membrane Penetration and an Endocytic Mechanism If wt-azurin entry is solely dependent on receptor-mediated endocytosis, it could be blocked by protonophore carbonyl cyanide m-chlorophrnylhydrazone (CCCP), a mitochondrial uncoupler of energy generation, or preincubalion with unlabeled azurin or other cupredoxins that block the receptors. J774 and UISO-Mel-2 cells were incubated with the cupredoxins at 10 fold excess concentration for 2 hr at 4° C., the cells washed thoroughly to remove the cupredoxins, and incubated with ALEXA FLUOR® 568-conjugated azurin for 1 hr at 37° C. There was as much internalized azurin as in cells not treated with the cupredoxins. The effects of cytochalasin D (available from Sigma-Aldrich, St. Louis, Mo. 63195), a known inhibitor of receptor-mediated endocytosis that disrupts the cellular microfilament network, and Brefeldin A (available from Sigma-Aldrich, St. Louis, Mo. 63195), which is known to disrupt the Golgi apparatus and inhibit classical vesicle-mediated secretion, were also tested. CCCP at 20 pM concentration significantly reduced the uptake of azurin in UISO-Mel-2 cells as did 0.25 to 0.5 pM cytochalasin D. Brefeldin A, on the other hand, had no significant effect.

Example 15. Entry of a GST-PEDIII-azu 50-77 Fusion Derivative into UISO-Mel-2 Cells A GST-fusion of *Pseudomonas aeruginosa* exotoxin A domain III (PEDIII) was constructed as described by Hwang, J. et al., *Cell* 48:129-36 (1987); Reiter, Y. and Pastan, I., *Trends Biotechnol.* 16:513-20 (1998). This GST-PEDIII fusion derivative contained amino acids 381-613 of the exotoxin A. PEDIII is known to harbor ADP-ribosyl transferase activity and inhibits cellular protein synthesis in eukaryotic cells by inhibiting eukaryotic elongation factor 2.

Figure 8A:
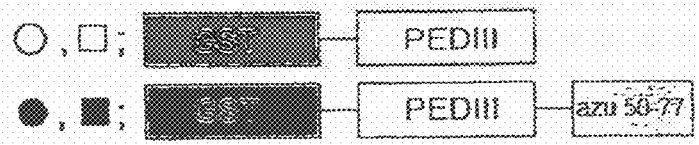
FIGS. 8 (A), (B) and (C). (A) Diagram showing the exotoxin A domain III (amino acids 405-613), as well as part of domain lb (amino acids 381-404), fused to GST (GST-PEDIII) as earlier described for the GST-GFP fusion. The azu 50-77 fragment was then ligated to the carboxyl end of GST-PEDIII (GST-PEDIII-azu 50-77), using PCR. (B) The fusion proteins were purified by glutathione Sepharose 4B column gel filtration column chromatography and run on SDS-PAGE for size determination. (C) Diagram showing action of GST-PEDIII-azu 50-77 fusion protein in UISO-Mel-2 cancer cells and in normal fibroblast (FBT) cells, as determined by PEDIII-mediated cytotoxicity. Various concentrations, as indicated, of GST-PEDIII and GST-PEDIII-azu 50-77 were incubated with UISO-Mel-2 and FBT cells for 24 h, after which the cell viability was determined by MTT assay.
Figure 8B:
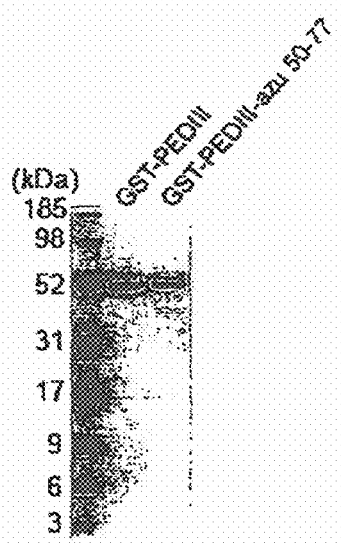
Figure 8C:
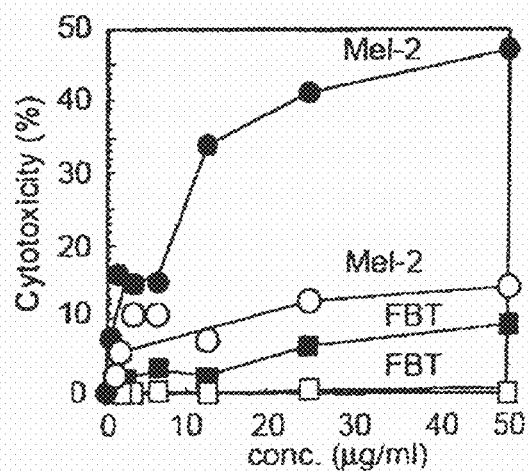

Using PCR as described for the GST-GFP-azu 50-77, the azu 50-77 sequence was introduced to the carboxyl end of the GST-PEDIII fusion protein (FIG. 8(*a*)). These two fusion proteins (GSTPEDIII and GST-PEDIII-azu 50-77) were purified by glutathione-sepharose 4B column chromatography as 52 and 54 kDa proteins (FIG. 8(*b*)). UISO-Mel-2 and normal fibroblast (FBT) cells were then incubated for 24 h at 37° C. with various concentrations of these proteins and the extent of cell death measured by MTT assay as described in Example 9.

While GST-PEDIII demonstrated only low cytotoxicity, the GST-PEDIII-azu 50-77 fusion protein had high cytotoxicity because of efficient entry to UISO-Mel-2 cells (FIG. 8(*c*)). In contrast, the fusion proteins demonstrated a low level of cytotoxicity towards the fibroblast cells.

Example 16. Destabilization of the α-Helix in Wt-Azurin has No Substantial Effect on its Internalization in UISO-Mel-2 Cells To examine if the α-helix plays a role in azurin entry, three helix-destabilizing proline residues were introduced in positions 54, 61 and 70 of wt-azurin (FIG. 6) and examined the entry of the full length A54PT61PK70P mutant azurin into UISO-Mel-2 cells. Single and double mutations in these positions were also constructed and tested for entry. The A54PT61PK70P mutant azurin was prepared by site-directed mutagenesis of the azurin gene using the QuickChange site-directed mutagenesis kit (Stratagene, La Jolla, Calif.).

The mutants were incubated at 200 μg/ml with UISO-Mel-2 cells for 1 hr at 37° C., after which the fluorescence was localized by confocal microscopy. In all cases, the ALEXA FLUOR® 568-conjugated mutant azurins entered UISO-Mel-2 cells. Similarly, when the GST-GFP-azu 50-77 fusion protein, as well as its triple A54PT61PK70P azu mutant variant, were examined for entry in UISO-Mel-2 cells, no significant difference was observed.

Example 17. Entry of a GST-PEDIII-Rusticyanin Fusion Derivative into UISO-Mel-2 Cells A GST-fusion of *Pseudomonas aeruginosa* exotoxin A domain III (PEDIII) and was constructed as in Example 15. Using PCR as described for the GST-GFP-azu 50-77, full-length rusticyanin sequence was introduced to the carboxyl end of the GST-PEDIII fusion protein. The fusion protein was purified by glutathione-sepharose 4B column chromatography. UISO-Mel-2 and FBT cells were then incubated for 24 h at 37° C. with various concentrations of the fusion protein and the extent of cell death measured by MTT assays as described in Example 7.

Figure 9:
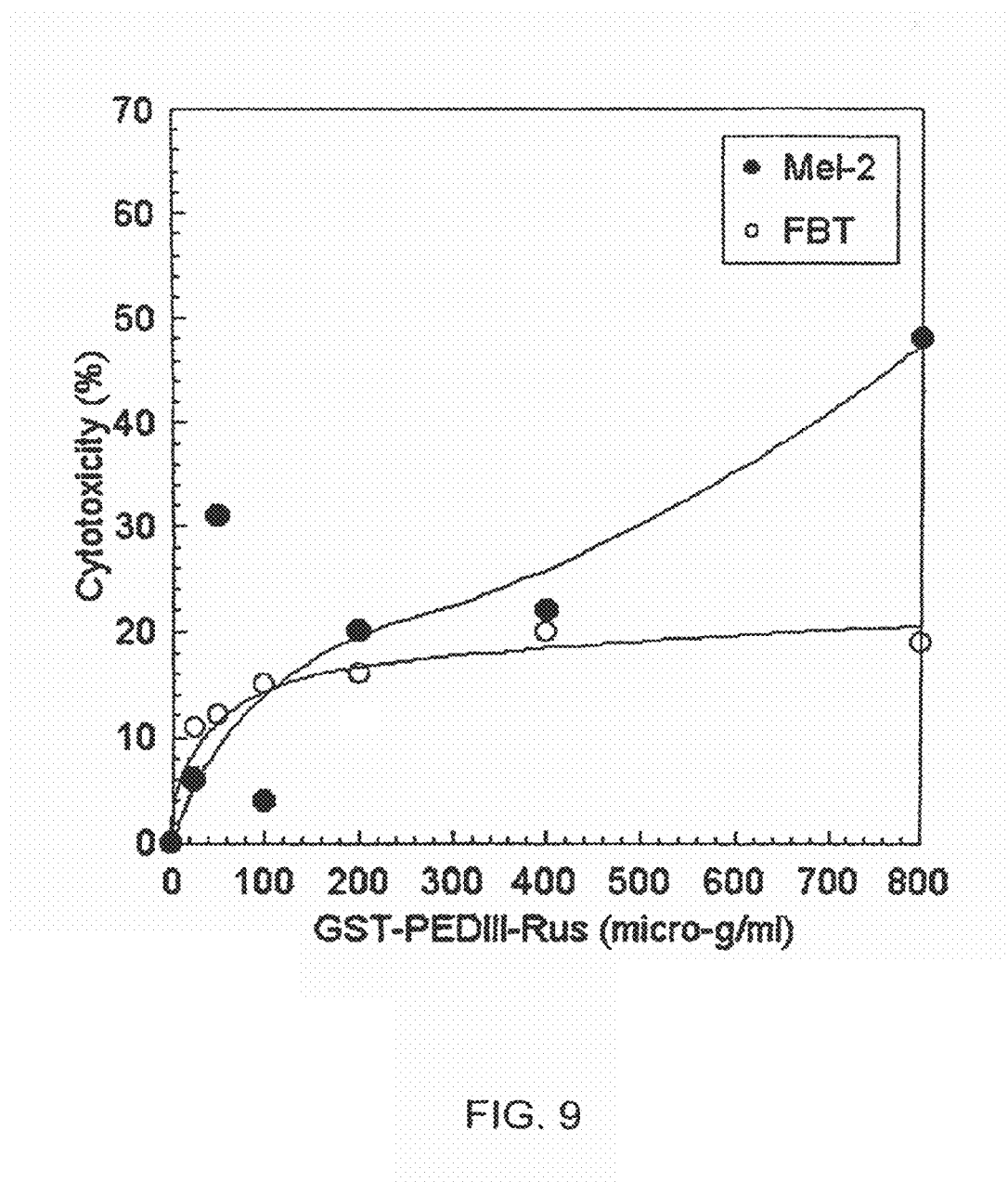
FIG. 9. Diagram PEDIII-mediated cytotoxicity of GST-PEDIII-rusticyanin fusion protein against UISO-Mel-2 cancer cells and FBT cells. Various concentrations, as indicated, of GST-PEDIII and GST-PEDIII-azu 50-77 were incubated with UISO-Mel-2 and FBT cells for 24 h, after which the cell viability was determined by MTT assay.

The GST-PEDIII-rusticyanin fusion protein exhibited high cytotoxicity against UISO-Mel-2 cells (FIG. 9). In contrast, the fusion protein demonstrated only a low level of cytotoxicity towards the FBT cells.

---

What is claimed is:

1. A complex comprising: an isolated peptide consisting of SEQ ID NO: 25 coupled to a cargo compound and wherein the isolated peptide can selectively enter mammalian cancer cells.

2. The complex of claim 1 wherein the cargo compound retards or kills mammalian cancer cells.

3. The complex of claim 2 wherein the cargo compound is a cytotoxic drug.

4. The complex of claim 1 wherein the cargo compound is selected from the group consisting of a protein, lipoprotein, polypeptide, peptide, polysaccharide, nucleic acid, dye, microparticle, nanoparticle, toxin and drug.

5. The complex of claim 1 wherein the cargo compound is selected from the group consisting of a protein and a polypeptide and wherein the peptide is linked to the cargo compound to form a fusion protein.

6. The complex of claim 1 wherein the cargo compound is a toxin.

7. The complex of claim 1 wherein the cargo compound is a detectable substance.

8. A pharmaceutical composition comprising the complex of claim 1 and a pharmaceutically acceptable carrier.

9. A kit comprising a reagent comprising the complex of claim 1.

10. The kit of claim 9, further comprising a reagent comprising a pharmaceutically-acceptable adjuvant or excipient.

11. The kit of claim 9, further comprising a vehicle for administration of the reagent.

* * * * *